(12) United States Patent
Taylor et al.

(10) Patent No.: US 9,848,889 B2
(45) Date of Patent: Dec. 26, 2017

(54) APPARATUS AND METHODS FOR BONE ACCESS AND CAVITY PREPARATION

(71) Applicant: Conventus Orthopaedics, Inc., Maple Grove, MN (US)

(72) Inventors: Kyle Taylor, Brooklyn Park, MN (US); Stefan J. Hertel, Austin, TX (US); Alex A. Peterson, Maple Grove, MN (US); Michael P. Brenzel, St. Paul, MN (US); Steve D. Kruse, St. Michael, MN (US); Todd A. Krinke, Buffalo, MN (US); Paul Hindrichs, Plymouth, MN (US)

(73) Assignee: Conventus Orthopaedics, Inc., Maple Grove, MN (US)

( * ) Notice: Subject to any disclaimer, the term of this patent is extended or adjusted under 35 U.S.C. 154(b) by 0 days.

(21) Appl. No.: 14/929,757

(22) Filed: Nov. 2, 2015

(65) Prior Publication Data

US 2016/0066926 A1    Mar. 10, 2016

Related U.S. Application Data

(63) Continuation of application No. 14/594,482, filed on Jan. 12, 2015, which is a continuation of application
(Continued)

(51) Int. Cl.
*A61B 17/16* (2006.01)
*A61B 17/17* (2006.01)

(52) U.S. Cl.
CPC ........ *A61B 17/1604* (2013.01); *A61B 17/164* (2013.01); *A61B 17/1617* (2013.01);
(Continued)

(58) Field of Classification Search
CPC .............. A61B 17/164; A61B 17/1604; A61B 17/1668; A61B 17/1686; A61B 17/1688
See application file for complete search history.

(56) References Cited

U.S. PATENT DOCUMENTS

| 1,362,513 A | 12/1919 | Skinner |
| 1,344,327 A | 6/1920 | Wilson |

(Continued)

FOREIGN PATENT DOCUMENTS

| CA | 2007210 A1 | 11/1990 |
| CA | 2452508 A1 | 1/2003 |

(Continued)

OTHER PUBLICATIONS

US 7,063,700, 06/2006, Michelson (withdrawn)
(Continued)

*Primary Examiner* — Nicholas Woodall
(74) *Attorney, Agent, or Firm* — Weiss & Arons LLP

(57) ABSTRACT

Apparatus and methods for preparing the interior of a bone for therapy. The therapy may include therapy for a bone fracture. The apparatus and methods may involve orienting a surgical instrument for proper deployment in the interior of the bone. An instrument guide may be positioned and retained against translation along, and rotation about one or more of three substantially orthogonal axes. Apparatus placed exterior to the bone may register the guide to a region inside the bone that is designated for preparation or treatment. One or more broaching members may be used to prepare the region for treatment. A broaching member may be expandable inside the bone. A broaching member may be flexible such that it broaches bone having a relatively lower density and it leaves bone having a relatively higher density substantially intact.

13 Claims, 43 Drawing Sheets

Related U.S. Application Data

No. 13/009,657, filed on Jan. 19, 2011, now Pat. No. 8,961,518.

(60) Provisional application No. 61/296,722, filed on Jan. 20, 2010, provisional application No. 61/389,507, filed on Oct. 4, 2010.

(52) U.S. Cl.
CPC ...... *A61B 17/1637* (2013.01); *A61B 17/1703* (2013.01); *A61B 17/1725* (2013.01); *A61B 17/1782* (2016.11)

(56) References Cited

U.S. PATENT DOCUMENTS

| | | |
|---|---|---|
| 1,493,240 A | 5/1924 | Bohn |
| 1,685,380 A | 9/1928 | Shultz |
| 2,137,710 A | 12/1937 | Anderson |
| 2,485,531 A | 1/1948 | Dzus et al. |
| 2,493,598 A | 1/1950 | Rozek |
| 2,537,070 A | 1/1951 | Longfellow |
| 2,580,821 A | 1/1952 | Nicola |
| 2,730,101 A * | 1/1956 | Hoffman .......... A61B 17/32002 606/108 |
| 2,780,223 A | 2/1957 | Haggland |
| 2,898,963 A | 8/1959 | Courtot |
| 3,143,915 A | 8/1964 | Tendler |
| 3,143,916 A | 8/1964 | Rice |
| 3,146,892 A | 9/1964 | White |
| 3,181,533 A | 5/1965 | Heath |
| 3,495,586 A | 2/1970 | Regenbogen |
| 3,517,128 A | 6/1970 | Hines |
| 3,593,342 A | 7/1971 | Niebauer et al. |
| 3,602,218 A | 8/1971 | Riordan |
| 3,623,164 A | 11/1971 | Bokros |
| 3,640,280 A | 2/1972 | Slanker et al. |
| 3,702,611 A | 11/1972 | Fishbein |
| 3,710,789 A | 1/1973 | Ersek |
| 3,744,488 A | 7/1973 | Cox |
| 3,745,590 A | 7/1973 | Stubstad |
| 3,759,257 A | 9/1973 | Fischer et al. |
| 3,760,802 A | 9/1973 | Fischer et al. |
| 3,779,239 A | 12/1973 | Fischer et al. |
| 3,805,775 A | 4/1974 | Fischer et al. |
| 3,828,790 A | 8/1974 | Curtiss et al. |
| 3,835,859 A | 9/1974 | Roberts et al. |
| 3,886,600 A | 6/1975 | Kahn et al. |
| 3,909,853 A | 10/1975 | Lennox |
| 3,917,249 A | 11/1975 | Constantine |
| 3,946,445 A | 3/1976 | Bentley et al. |
| 3,970,075 A | 7/1976 | Sindelar et al. |
| 3,986,504 A | 10/1976 | Avila |
| 3,992,726 A | 11/1976 | Freeman et al. |
| 4,036,107 A | 7/1977 | Constantine |
| 4,091,806 A | 5/1978 | Aginsky |
| 4,124,026 A | 11/1978 | Berner et al. |
| 4,156,296 A | 5/1979 | Johnson et al. |
| 4,180,871 A | 1/1980 | Hamas |
| 4,190,044 A | 2/1980 | Wood |
| 4,193,139 A | 3/1980 | Walker |
| 4,194,250 A | 3/1980 | Walker |
| 4,203,444 A | 5/1980 | Bonnell et al. |
| 4,204,531 A | 5/1980 | Aginsky |
| 4,213,208 A | 7/1980 | Marne |
| 4,227,518 A | 10/1980 | Aginsky |
| 4,229,840 A | 10/1980 | Gristina |
| 4,231,121 A | 11/1980 | Lewis |
| 4,262,665 A | 4/1981 | Roalstad et al. |
| 4,273,128 A | 6/1981 | Lary |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,349,922 A | 9/1982 | Agee |
| 4,352,212 A | 10/1982 | Greene et al. |
| 4,430,991 A | 2/1984 | Darnell |
| 4,438,762 A | 3/1984 | Kyle |
| 4,453,539 A | 6/1984 | Raftopoulos et al. |
| 4,473,070 A | 9/1984 | Matthews et al. |
| 4,485,816 A | 12/1984 | Krumme |
| 4,502,554 A | 3/1985 | Jones |
| 4,519,100 A | 5/1985 | Wills et al. |
| 4,522,200 A | 6/1985 | Stednitz |
| 4,530,114 A | 7/1985 | Tepic |
| 4,548,199 A | 10/1985 | Agee |
| 4,572,186 A | 2/1986 | Gould et al. |
| 4,573,448 A | 3/1986 | Kambin |
| 4,585,000 A | 4/1986 | Hershenson |
| 4,590,930 A | 5/1986 | Kurth et al. |
| 4,601,290 A | 7/1986 | Effron et al. |
| 4,608,965 A * | 9/1986 | Anspach, Jr. ...... A61B 17/0281 600/101 |
| 4,611,594 A | 9/1986 | Grayhack et al. |
| 4,619,122 A | 10/1986 | Simpson |
| 4,627,434 A | 12/1986 | Murray |
| 4,634,445 A | 1/1987 | Helal |
| 4,643,177 A | 2/1987 | Sheppard et al. |
| 4,644,951 A | 2/1987 | Bays |
| 4,646,738 A | 3/1987 | Trott |
| 4,655,203 A | 4/1987 | Tormala et al. |
| 4,660,557 A | 4/1987 | Collis |
| 4,662,371 A | 5/1987 | Whipple et al. |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,721,103 A | 1/1988 | Freedland |
| 4,730,608 A | 3/1988 | Schlein |
| 4,731,087 A | 3/1988 | Sculco et al. |
| 4,751,922 A | 6/1988 | DiPietropolo |
| 4,772,261 A | 9/1988 | Von Hoff et al. |
| 4,777,942 A | 10/1988 | Frey et al. |
| 4,782,833 A | 11/1988 | Einhorn et al. |
| 4,790,302 A | 12/1988 | Colwill et al. |
| 4,809,793 A | 3/1989 | Hailey |
| 4,820,305 A | 4/1989 | Harms et al. |
| 4,875,474 A | 10/1989 | Border |
| 4,886,062 A | 12/1989 | Wiktor |
| 4,914,818 A | 4/1990 | Hall et al. |
| 4,921,478 A | 5/1990 | Solano et al. |
| 4,941,466 A | 7/1990 | Romano |
| 4,946,459 A | 8/1990 | Bradshaw et al. |
| 4,954,126 A | 9/1990 | Wallsten |
| 4,955,916 A | 9/1990 | Carignan et al. |
| 4,969,888 A | 11/1990 | Scholten et al. |
| 4,973,257 A | 11/1990 | Lhotak |
| 4,978,349 A | 12/1990 | Frigg |
| 4,998,539 A | 3/1991 | Delsanti |
| 5,002,546 A | 3/1991 | Romano |
| 5,015,255 A | 5/1991 | Kuslich |
| 5,030,201 A | 7/1991 | Palestrant |
| 5,035,714 A | 7/1991 | Willert et al. |
| 5,053,036 A | 10/1991 | Perren et al. |
| 5,057,103 A | 10/1991 | Davis |
| 5,059,193 A | 10/1991 | Kuslich |
| 5,059,206 A | 10/1991 | Winters |
| 5,062,845 A | 11/1991 | Kuslich et al. |
| 5,066,296 A | 11/1991 | Chapman et al. |
| 5,067,957 A | 11/1991 | Jervis |
| 5,071,407 A | 12/1991 | Termin et al. |
| 5,084,050 A | 1/1992 | Draenert |
| 5,100,423 A | 3/1992 | Fearnot |
| 5,102,413 A | 4/1992 | Poddar |
| 5,108,404 A | 4/1992 | Scholten et al. |
| 5,108,435 A | 4/1992 | Gustavson et al. |
| 5,112,333 A | 5/1992 | Fixel |
| 5,113,846 A | 5/1992 | Hiltebrandt et al. |
| 5,116,335 A | 5/1992 | Hannon et al. |
| 5,122,134 A | 6/1992 | Borzone et al. |
| 5,129,906 A | 7/1992 | Ross et al. |
| 5,135,527 A | 8/1992 | Ender |
| 5,139,497 A | 8/1992 | Tilghman et al. |
| 5,151,103 A | 9/1992 | Tepic et al. |

(56) References Cited

U.S. PATENT DOCUMENTS

| | | |
|---|---|---|
| 5,169,402 A | 12/1992 | Elloy |
| 5,171,284 A | 12/1992 | Branemark |
| 5,174,374 A | 12/1992 | Hailey |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,201,741 A | 4/1993 | Dulebohn |
| 5,203,773 A | 4/1993 | Green |
| 5,221,261 A | 6/1993 | Termin et al. |
| 5,236,431 A | 8/1993 | Gogolewski et al. |
| 5,242,017 A | 9/1993 | Hailey |
| 5,242,461 A | 9/1993 | Kortenbach et al. |
| 5,250,048 A | 10/1993 | Gundolf |
| 5,263,955 A | 11/1993 | Baumgart et al. |
| 5,269,785 A | 12/1993 | Bonutti |
| 5,275,602 A | 1/1994 | Shimizu et al. |
| 5,275,608 A | 1/1994 | Forman et al. |
| 5,281,225 A | 1/1994 | Vicenzi |
| 5,281,226 A | 1/1994 | Davydov et al. |
| 5,286,249 A | 2/1994 | Thibodaux |
| 5,307,790 A | 5/1994 | Byrne |
| 5,314,486 A | 5/1994 | Zang et al. |
| 5,326,205 A | 7/1994 | Anspach et al. |
| 5,334,184 A | 8/1994 | Bimman |
| 5,358,405 A | 10/1994 | Imai |
| 5,376,097 A | 12/1994 | Phillips |
| 5,376,100 A | 12/1994 | Lefebvre |
| 5,378,239 A | 1/1995 | Termin et al. |
| 5,380,328 A | 1/1995 | Morgan |
| 5,397,320 A | 3/1995 | Essig et al. |
| 5,415,660 A | 5/1995 | Campbell et al. |
| 5,423,823 A | 6/1995 | Schmieding |
| 5,431,671 A | 7/1995 | Nallakrishnan |
| 5,437,665 A | 8/1995 | Munro |
| 5,437,674 A | 8/1995 | Worcel et al. |
| 5,439,464 A | 8/1995 | Shapiro |
| 5,445,639 A | 8/1995 | Kuslich et al. |
| 5,454,365 A | 10/1995 | Bonutti |
| 5,458,599 A | 10/1995 | Adobbati |
| 5,458,648 A | 10/1995 | Berman et al. |
| 5,462,547 A | 10/1995 | Weigum |
| 5,467,763 A | 11/1995 | McMahon et al. |
| D365,634 S | 12/1995 | Morgan |
| 5,474,557 A | 12/1995 | Mai |
| 5,480,447 A | 1/1996 | Skiba |
| 5,496,277 A | 3/1996 | Termin et al. |
| 5,496,330 A | 3/1996 | Bates et al. |
| 5,499,981 A | 3/1996 | Kordis |
| 5,501,695 A | 3/1996 | Anspach et al. |
| 5,505,734 A | 4/1996 | Caniggia et al. |
| 5,509,919 A | 4/1996 | Young |
| 5,512,037 A | 4/1996 | Russell et al. |
| 5,527,316 A | 6/1996 | Stone et al. |
| 5,531,792 A | 7/1996 | Huene |
| 5,536,267 A | 7/1996 | Edwards et al. |
| 5,540,693 A | 7/1996 | Fisher |
| 5,545,162 A | 8/1996 | Huebner |
| 5,554,163 A | 9/1996 | Shturman |
| 5,556,408 A | 9/1996 | Farhat |
| 5,571,098 A | 11/1996 | Domankevitz et al. |
| 5,571,189 A | 11/1996 | Kuslich |
| 5,578,035 A | 11/1996 | Lin |
| 5,582,577 A | 12/1996 | Lund et al. |
| 5,582,618 A | 12/1996 | Chin et al. |
| 5,586,983 A | 12/1996 | Sanders et al. |
| 5,586,985 A | 12/1996 | Putnam et al. |
| 5,586,990 A | 12/1996 | Hahnen et al. |
| 5,591,169 A | 1/1997 | Benoist |
| 5,591,170 A | 1/1997 | Spievack et al. |
| 5,597,378 A | 1/1997 | Jervis |
| 5,602,935 A | 2/1997 | Yoshida et al. |
| 5,620,414 A | 4/1997 | Campbell |
| 5,620,445 A | 4/1997 | Brosnahan et al. |
| 5,624,440 A | 4/1997 | Huebner |
| 5,624,447 A | 4/1997 | Myers |
| 5,626,580 A | 5/1997 | Brosnahan |
| 5,628,747 A | 5/1997 | Richelsoph |
| 5,645,589 A | 7/1997 | Li |
| 5,658,280 A | 8/1997 | Issa |
| 5,658,283 A | 8/1997 | Huebner |
| 5,660,188 A | 8/1997 | Groiso |
| 5,662,649 A | 9/1997 | Huebner |
| 5,667,509 A | 9/1997 | Westin |
| 5,676,545 A | 10/1997 | Jones |
| 5,676,699 A | 10/1997 | Gogolewski et al. |
| 5,681,310 A | 10/1997 | Yuan et al. |
| 5,683,389 A | 11/1997 | Orsak |
| 5,685,826 A | 11/1997 | Bonutti |
| 5,693,011 A | 12/1997 | Onik |
| 5,697,981 A | 12/1997 | Ison et al. |
| 5,707,374 A | 1/1998 | Schmidt |
| 5,709,697 A | 1/1998 | Ratcliff et al. |
| 5,718,704 A | 2/1998 | Medoff |
| 5,725,541 A | 3/1998 | Anspach, III et al. |
| 5,728,047 A | 3/1998 | Edoga |
| 5,728,098 A | 3/1998 | Sherman et al. |
| 5,730,704 A | 3/1998 | Avitall |
| 5,741,266 A | 4/1998 | Moran et al. |
| 5,741,282 A | 4/1998 | Anspach et al. |
| 5,758,713 A | 6/1998 | Fallet |
| 5,779,703 A | 7/1998 | Benoist |
| 5,792,106 A | 8/1998 | Mische |
| 5,810,721 A | 9/1998 | Mueller et al. |
| 5,814,044 A | 9/1998 | Hooven |
| 5,817,098 A | 10/1998 | Albrektsson et al. |
| 5,824,095 A | 10/1998 | Di Maio, Jr. et al. |
| 5,827,289 A | 10/1998 | Reiley et al. |
| 5,827,312 A | 10/1998 | Brown et al. |
| D403,069 S | 12/1998 | Drewry et al. |
| 5,853,054 A | 12/1998 | McGarian et al. |
| 5,876,399 A | 3/1999 | Chia et al. |
| 5,879,352 A | 3/1999 | Filoso et al. |
| 5,879,355 A | 3/1999 | Ullmark |
| 5,885,258 A | 3/1999 | Sachdeva et al. |
| 5,885,282 A | 3/1999 | Szabo |
| 5,888,196 A | 3/1999 | Bonutti |
| 5,891,147 A | 4/1999 | Moskovitz et al. |
| 5,893,850 A | 4/1999 | Cachia |
| 5,897,556 A | 4/1999 | Drewry et al. |
| 5,908,423 A | 6/1999 | Kashuba et al. |
| 5,915,036 A | 6/1999 | Grunkin et al. |
| 5,919,195 A | 7/1999 | Wilson et al. |
| 5,925,039 A | 7/1999 | Landingham |
| 5,928,239 A | 7/1999 | Mirza |
| 5,935,127 A | 8/1999 | Border |
| 5,938,699 A | 8/1999 | Campbell |
| 5,941,878 A | 8/1999 | Medoff |
| 5,951,467 A | 9/1999 | Picha et al. |
| 5,951,556 A | 9/1999 | Faccioli et al. |
| 5,957,884 A | 9/1999 | Hooven |
| 5,964,698 A | 10/1999 | Fowler |
| 5,976,134 A | 11/1999 | Huebner |
| 5,980,525 A | 11/1999 | Bryant et al. |
| 5,984,932 A | 11/1999 | Yoon |
| 5,984,937 A | 11/1999 | Morse et al. |
| 5,997,538 A | 12/1999 | Asnis et al. |
| 6,001,099 A | 12/1999 | Huebner |
| 6,015,406 A | 1/2000 | Goble et al. |
| 6,019,762 A | 2/2000 | Cole |
| 6,019,947 A | 2/2000 | Kucherov |
| 6,030,406 A * | 2/2000 | Davis ............... A61B 17/00008 604/104 |
| 6,033,412 A | 3/2000 | Losken et al. |
| 6,045,564 A | 4/2000 | Walen |
| 6,048,309 A | 4/2000 | Flom et al. |
| 6,053,922 A | 4/2000 | Krause et al. |
| 6,056,750 A | 5/2000 | Lob |
| 6,068,642 A | 5/2000 | Johnson et al. |
| 6,068,648 A | 5/2000 | Cole et al. |
| 6,074,392 A | 6/2000 | Durham |

(56) References Cited

U.S. PATENT DOCUMENTS

| | | |
|---|---|---|
| 6,093,162 A | 7/2000 | Fairleigh et al. |
| 6,096,040 A | 8/2000 | Esser |
| 6,113,603 A | 9/2000 | Medoff |
| 6,120,472 A | 9/2000 | Singer |
| 6,120,504 A | 9/2000 | Brumback et al. |
| 6,123,704 A | 9/2000 | Hajianpour |
| 6,126,662 A | 10/2000 | Carmichael et al. |
| 6,127,597 A | 10/2000 | Beyar et al. |
| 6,129,762 A | 10/2000 | Li |
| 6,142,935 A | 11/2000 | Flom et al. |
| 6,143,012 A | 11/2000 | Gausepohl |
| 6,149,651 A | 11/2000 | Drewry et al. |
| 6,149,689 A | 11/2000 | Grundei |
| 6,156,069 A | 12/2000 | Amstutz |
| 6,162,223 A | 12/2000 | Orsak et al. |
| 6,162,224 A | 12/2000 | Huebner |
| 6,171,309 B1 | 1/2001 | Huebner |
| 6,174,312 B1 | 1/2001 | Laminger |
| 6,197,027 B1 | 3/2001 | Hajianpour |
| 6,200,330 B1 | 3/2001 | Benderev et al. |
| 6,216,573 B1 | 4/2001 | Moutafis et al. |
| 6,221,074 B1 | 4/2001 | Cole et al. |
| 6,221,102 B1 | 4/2001 | Baker et al. |
| 6,224,600 B1 | 5/2001 | Protogirou |
| 6,224,604 B1 | 5/2001 | Suddaby |
| 6,231,576 B1 | 5/2001 | Frigg et al. |
| 6,235,043 B1 | 5/2001 | Reiley et al. |
| 6,238,417 B1 | 5/2001 | Cole |
| 6,241,734 B1 | 6/2001 | Scribner et al. |
| 6,248,110 B1 | 6/2001 | Reiley et al. |
| 6,258,096 B1 | 7/2001 | Seki |
| 6,261,289 B1 | 7/2001 | Levy |
| 6,280,474 B1 | 8/2001 | Cassidy et al. |
| 6,296,639 B1 | 10/2001 | Truckai et al. |
| 6,299,642 B1 | 10/2001 | Chan |
| 6,302,915 B1 | 10/2001 | Cooney et al. |
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,331,166 B1 | 12/2001 | Burbank et al. |
| 6,332,885 B1 | 12/2001 | Martella |
| 6,332,886 B1 | 12/2001 | Green et al. |
| 6,337,142 B2 | 1/2002 | Harder et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,440,138 B1 | 8/2002 | Reiley et al. |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,475,789 B1 | 11/2002 | Cech et al. |
| 6,488,685 B1 | 12/2002 | Manderson |
| 6,491,694 B1 | 12/2002 | Orsak |
| 6,511,481 B2 | 1/2003 | von Hoffmann et al. |
| 6,517,541 B1 | 2/2003 | Sesic |
| 6,527,775 B1 | 3/2003 | Warburton |
| 6,533,788 B1 | 3/2003 | Orbay |
| 6,540,770 B1 | 4/2003 | Tornier et al. |
| 6,544,267 B1 | 4/2003 | Cole et al. |
| 6,551,321 B1 | 4/2003 | Burkinshaw et al. |
| 6,554,833 B2 | 4/2003 | Levy et al. |
| 6,575,878 B1 | 6/2003 | Choy |
| 6,575,973 B1 | 6/2003 | Shekalim |
| 6,575,978 B2 | 6/2003 | Peterson et al. |
| 6,582,467 B1 | 6/2003 | Teitelbaum et al. |
| 6,585,736 B2 | 7/2003 | Hajianpour |
| 6,585,770 B1 | 7/2003 | White et al. |
| 6,610,839 B1 | 8/2003 | Morin et al. |
| 6,613,052 B1 | 9/2003 | Kinnett |
| 6,613,054 B2 | 9/2003 | Scribner et al. |
| 6,617,110 B1 | 9/2003 | Cech et al. |
| 6,632,224 B2 | 10/2003 | Cachia et al. |
| 6,641,616 B1 | 11/2003 | Grundei |
| 6,645,210 B2 | 11/2003 | Manderson |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 * | 1/2004 | Foley .................. A61B 17/025 |
| | | 600/201 |
| 6,679,886 B2 | 1/2004 | Weikel et al. |
| 6,682,565 B1 | 1/2004 | Krishnan |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Krause et al. |
| 6,712,073 B2 | 3/2004 | Manderson |
| 6,712,858 B1 | 3/2004 | Grungei et al. |
| 6,719,761 B1 | 4/2004 | Reiley et al. |
| 6,719,793 B2 | 4/2004 | McGee et al. |
| 6,740,090 B1 | 5/2004 | Cragg et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 | 8/2004 | Frei et al. |
| 6,783,530 B1 | 8/2004 | Levy et al. |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,911,046 B2 | 6/2005 | Schulter |
| 6,913,605 B2 | 7/2005 | Fletcher et al. |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B1 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,953,313 B2 | 10/2005 | Tylosky |
| 6,975,894 B2 | 12/2005 | Wehrli et al. |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B1 | 4/2006 | Masson et al. |
| 7,025,789 B2 | 4/2006 | Chow et al. |
| 7,041,104 B1 | 5/2006 | Cole et al. |
| 7,041,138 B2 | 5/2006 | Lange |

(56) References Cited

U.S. PATENT DOCUMENTS

| | | |
|---|---|---|
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 | 10/2006 | Wood |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |
| 7,179,024 B2 | 2/2007 | Greenhalgh |
| 7,189,237 B2 | 3/2007 | Huebner |
| 7,189,240 B1 | 3/2007 | Dekel |
| 7,195,589 B1 | 3/2007 | Masson et al. |
| 7,195,633 B2 | 3/2007 | Medoff et al. |
| 7,214,227 B2 | 5/2007 | Colleran et al. |
| 7,220,282 B2 | 5/2007 | Kuslich et al. |
| 7,229,441 B2 | 6/2007 | Trieu et al. |
| 7,235,079 B2 | 6/2007 | Jensen et al. |
| 7,237,556 B2 | 7/2007 | Smothers et al. |
| 7,255,712 B1 | 8/2007 | Steinberg |
| 7,258,692 B2 | 8/2007 | Thelen et al. |
| 7,264,622 B2 | 9/2007 | Michelson |
| 7,267,678 B2 | 9/2007 | Medoff |
| 7,282,053 B2 | 10/2007 | Orbay |
| 7,294,130 B2 | 11/2007 | Orbay |
| 7,300,449 B2 | 11/2007 | Mische et al. |
| 7,306,603 B2 | 12/2007 | Boehm et al. |
| 7,306,683 B2 | 12/2007 | Cheung et al. |
| 7,311,711 B2 | 12/2007 | Cole |
| D560,128 S | 1/2008 | Diederich et al. |
| 7,322,938 B2 | 1/2008 | Burbank et al. |
| 7,326,249 B2 | 2/2008 | Lange |
| 7,329,228 B2 | 2/2008 | Burbank et al. |
| 7,341,601 B2 | 3/2008 | Eisermann et al. |
| 7,344,539 B2 | 3/2008 | Serhan et al. |
| 7,354,453 B2 | 4/2008 | McAfee |
| 7,422,360 B2 | 9/2008 | Kozyuk |
| 7,465,318 B2 | 12/2008 | Sennett et al. |
| 7,476,226 B2 | 1/2009 | Weikel et al. |
| 7,481,815 B2 | 1/2009 | Fernandez |
| 7,485,119 B2 | 2/2009 | Thelen et al. |
| 7,488,320 B2 | 2/2009 | Middleton |
| 7,488,329 B2 | 2/2009 | Thelen et al. |
| D589,147 S | 3/2009 | Colleran et al. |
| 7,500,977 B2 | 3/2009 | Assell et al. |
| 7,507,241 B2 | 3/2009 | Levy et al. |
| 7,520,879 B2 | 4/2009 | Justis et al. |
| 7,527,632 B2 | 5/2009 | Houghton et al. |
| 7,563,263 B2 | 7/2009 | Orbay et al. |
| 7,569,061 B2 | 8/2009 | Colleran |
| 7,578,824 B2 | 8/2009 | Justin et al. |
| 7,588,575 B2 | 9/2009 | Colleran et al. |
| 7,588,577 B2 | 9/2009 | Fencl et al. |
| 7,588,588 B2 | 9/2009 | Spitler et al. |
| 7,601,152 B2 | 10/2009 | Levy et al. |
| 7,611,515 B2 | 11/2009 | Wolford et al. |
| 7,621,950 B1 | 11/2009 | Globerman et al. |
| 7,632,277 B2 | 12/2009 | Woll et al. |
| 7,632,310 B2 | 12/2009 | Clifford et al. |
| 7,666,226 B2 | 2/2010 | Schaller |
| 7,670,339 B2 | 3/2010 | Levy et al. |
| 7,670,374 B2 | 3/2010 | Schaller |
| 7,670,375 B2 | 3/2010 | Schaller |
| 7,682,364 B2 | 3/2010 | Reiley et al. |
| 7,695,471 B2 | 4/2010 | Cheung et al. |
| 7,695,502 B2 | 4/2010 | Orbay et al. |
| 7,704,251 B2 | 4/2010 | Huebner et al. |
| 7,708,742 B2 | 5/2010 | Scribner et al. |
| 7,713,271 B2 | 5/2010 | Warburton et al. |
| 7,717,472 B2 | 5/2010 | Johnson |
| 7,722,612 B2 | 5/2010 | Sala et al. |
| 7,722,626 B2 | 5/2010 | Middleman et al. |
| 7,727,264 B2 | 6/2010 | Orbay et al. |
| 7,731,720 B2 | 6/2010 | Sand et al. |
| 7,749,232 B2 | 7/2010 | Salerni |
| 7,758,500 B2 | 7/2010 | Boyd et al. |
| 7,785,368 B2 | 8/2010 | Schaller |
| 7,806,929 B2 | 10/2010 | Brown |
| 7,811,291 B2 | 10/2010 | Liu et al. |
| 7,828,802 B2 | 11/2010 | Levy et al. |
| 7,837,612 B2 | 11/2010 | Gill et al. |
| 7,842,041 B2 | 11/2010 | Liu et al. |
| 7,846,162 B2 | 12/2010 | Nelson et al. |
| 7,879,038 B2 | 2/2011 | Reiley et al. |
| 7,879,103 B2 | 2/2011 | Gertzman et al. |
| 7,905,909 B2 | 3/2011 | Orbay et al. |
| 7,909,825 B2 | 3/2011 | Saravia et al. |
| 7,909,827 B2 | 3/2011 | Reiley et al. |
| 7,909,873 B2 | 3/2011 | Tan-Malecki et al. |
| 7,914,533 B2 | 3/2011 | Nelson et al. |
| 7,931,689 B2 | 4/2011 | Hochschuler et al. |
| 7,942,875 B2 | 5/2011 | Nelson et al. |
| 7,959,634 B2 | 6/2011 | Sennett |
| 7,959,638 B2 | 6/2011 | Osorio et al. |
| 7,959,683 B2 | 6/2011 | Semler et al. |
| 7,967,827 B2 | 6/2011 | Osorio et al. |
| 7,967,865 B2 | 6/2011 | Schaller |
| 7,972,340 B2 | 7/2011 | Sand et al. |
| 7,988,735 B2 | 8/2011 | Yurek et al. |
| 8,007,498 B2 | 8/2011 | Mische |
| RE42,757 E | 9/2011 | Kuslich et al. |
| 8,021,365 B2 | 9/2011 | Phan |
| 8,021,366 B2 | 9/2011 | Phan |
| 8,043,334 B2 | 10/2011 | Fisher et al. |
| 8,057,544 B2 | 11/2011 | Schaller |
| 8,105,236 B2 | 1/2012 | Malandain et al. |
| 8,109,933 B2 | 2/2012 | Truckai et al. |
| 8,114,084 B2 | 2/2012 | Betts |
| 8,118,952 B2 | 2/2012 | Gall et al. |
| 8,128,627 B2 | 3/2012 | Justin et al. |
| 8,152,737 B2 | 4/2012 | Burbank et al. |
| 8,157,804 B2 | 4/2012 | Betts |
| 8,226,719 B2 | 7/2012 | Melsheimer et al. |
| 8,241,335 B2 | 8/2012 | Truckai et al. |
| 8,287,538 B2 | 10/2012 | Brenzel et al. |
| 8,287,539 B2 | 10/2012 | Nelson et al. |
| 8,287,541 B2 | 10/2012 | Nelson et al. |
| 8,317,791 B2 | 11/2012 | Phan |
| 8,353,911 B2 | 1/2013 | Goldin et al. |
| 8,366,773 B2 | 2/2013 | Schaller et al. |
| 8,409,211 B2 | 4/2013 | Baroud |
| 8,430,879 B2 | 4/2013 | Stoneburner et al. |
| 8,439,917 B2 | 5/2013 | Saravia et al. |
| 8,485,798 B2 | 7/2013 | Sheth et al. |
| 8,491,591 B2 | 7/2013 | Fürderer |
| 8,496,394 B2 | 7/2013 | Schneider |
| 8,496,657 B2 | 7/2013 | Bonutti et al. |
| 8,496,658 B2 | 7/2013 | Stoneburner et al. |
| 8,512,398 B2 | 8/2013 | Alkhatib |
| 8,568,413 B2 | 10/2013 | Mazur et al. |
| 8,579,537 B2 | 11/2013 | VanLandingham et al. |
| 8,597,276 B2 | 12/2013 | Vongphakdy et al. |
| 8,906,022 B2 | 12/2014 | Krinke et al. |
| 8,951,251 B2 * | 2/2015 | Willard ............... A61B 18/1492 606/41 |
| 8,961,518 B2 | 2/2015 | Taylor et al. |
| 9,155,574 B2 | 10/2015 | Saravia et al. |
| 2001/0018588 A1 | 8/2001 | Harder et al. |
| 2001/0034526 A1 | 10/2001 | Kuslich et al. |
| 2001/0053912 A1 | 12/2001 | Frigg |
| 2002/0013600 A1 | 1/2002 | Scribner et al. |
| 2002/0015517 A1 | 2/2002 | Hwang et al. |

(56) References Cited

U.S. PATENT DOCUMENTS

| | | |
|---|---|---|
| 2002/0029081 A1 | 3/2002 | Scarborough et al. |
| 2002/0032444 A1 | 3/2002 | Mische |
| 2002/0055742 A1 | 5/2002 | Lieberman |
| 2002/0055785 A1 | 5/2002 | Harris |
| 2002/0065530 A1 | 5/2002 | Mische |
| 2002/0068974 A1 | 6/2002 | Kuslich et al. |
| 2002/0111629 A1 | 8/2002 | Phillips |
| 2002/0111690 A1 | 8/2002 | Hyde |
| 2002/0120269 A1 | 8/2002 | Lange |
| 2002/0120270 A1 | 8/2002 | Trieu et al. |
| 2002/0123750 A1 | 9/2002 | Eisermann et al. |
| 2002/0133153 A1 | 9/2002 | Hyde |
| 2002/0133156 A1 | 9/2002 | Cole |
| 2002/0133172 A1 | 9/2002 | Lambrecht et al. |
| 2002/0133175 A1 | 9/2002 | Carson |
| 2002/0138149 A1 | 9/2002 | Hyde |
| 2002/0143329 A1 | 10/2002 | Serhan et al. |
| 2002/0143333 A1 | 10/2002 | von Hoffmann et al. |
| 2002/0143334 A1 | 10/2002 | Hoffmann et al. |
| 2002/0143335 A1 | 10/2002 | von Hoffmann et al. |
| 2002/0147451 A1 | 10/2002 | Mcgee |
| 2002/0147455 A1 | 10/2002 | Carson |
| 2002/0165461 A1 | 11/2002 | Hayzelden et al. |
| 2002/0171208 A1 | 11/2002 | Lechot et al. |
| 2002/0173813 A1 | 11/2002 | Peterson et al. |
| 2002/0183758 A1 | 12/2002 | Middleton et al. |
| 2002/0191823 A1 | 12/2002 | Wehrli et al. |
| 2003/0040805 A1 | 2/2003 | Minamikawa |
| 2003/0055373 A1 | 3/2003 | Sramek et al. |
| 2003/0055425 A1 | 3/2003 | Hajianpour |
| 2003/0069582 A1 | 4/2003 | Culbert |
| 2003/0069645 A1 | 4/2003 | Ball et al. |
| 2003/0074075 A1 | 4/2003 | Thomas, Jr. et al. |
| 2003/0083660 A1 | 5/2003 | Orbay |
| 2003/0083662 A1 | 5/2003 | Middleton |
| 2003/0093076 A1 | 5/2003 | Venturini et al. |
| 2003/0097132 A1 | 5/2003 | Padget et al. |
| 2003/0097133 A1 | 5/2003 | Green et al. |
| 2003/0105461 A1 | 6/2003 | Putnam |
| 2003/0109932 A1 | 6/2003 | Keynan |
| 2003/0120273 A1 | 6/2003 | Cole |
| 2003/0130660 A1 | 7/2003 | Levy et al. |
| 2003/0153918 A1 | 8/2003 | Putnam et al. |
| 2003/0187449 A1 | 10/2003 | McCleary et al. |
| 2003/0216738 A1 | 11/2003 | Azar |
| 2003/0220641 A1 | 11/2003 | Thelen et al. |
| 2003/0220644 A1 | 11/2003 | Thelen et al. |
| 2003/0220646 A1 | 11/2003 | Thelen et al. |
| 2003/0220698 A1 | 11/2003 | Mears et al. |
| 2003/0225407 A1 | 12/2003 | Estrada |
| 2004/0024410 A1 | 2/2004 | Olson, Jr. et al. |
| 2004/0039384 A1 | 2/2004 | Boehm et al. |
| 2004/0044413 A1 | 3/2004 | Schulter |
| 2004/0049192 A1 | 3/2004 | Shimizu |
| 2004/0078082 A1 | 4/2004 | Lange |
| 2004/0087956 A1 | 5/2004 | Weikel et al. |
| 2004/0092946 A1 | 5/2004 | Bagga et al. |
| 2004/0102777 A1 | 5/2004 | Huebner |
| 2004/0102778 A1 | 5/2004 | Huebner et al. |
| 2004/0102788 A1 | 5/2004 | Huebner et al. |
| 2004/0106925 A1 | 6/2004 | Culbert |
| 2004/0138665 A1 | 7/2004 | Padget et al. |
| 2004/0143264 A1 | 7/2004 | McAfee |
| 2004/0153080 A1 | 8/2004 | Dong et al. |
| 2004/0153114 A1 | 8/2004 | Reiley et al. |
| 2004/0153115 A1 | 8/2004 | Reiley et al. |
| 2004/0167528 A1 | 8/2004 | Schantz |
| 2004/0167625 A1 | 8/2004 | Beyar et al. |
| 2004/0181221 A1 | 9/2004 | Huebner et al. |
| 2004/0193163 A1 | 9/2004 | Orbay |
| 2004/0193164 A1 | 9/2004 | Orbay |
| 2004/0193165 A1 | 9/2004 | Orbay |
| 2004/0193251 A1 | 9/2004 | Rudnick et al. |
| 2004/0193267 A1 | 9/2004 | Jones et al. |
| 2004/0208717 A1 | 10/2004 | Greenhalgh |
| 2004/0214311 A1 | 10/2004 | Levy |
| 2004/0220678 A1 | 11/2004 | Chow et al. |
| 2004/0230193 A1 | 11/2004 | Cheung et al. |
| 2004/0236327 A1 | 11/2004 | Paul et al. |
| 2004/0236328 A1 | 11/2004 | Paul et al. |
| 2004/0236339 A1 | 11/2004 | Pepper |
| 2004/0249375 A1 | 12/2004 | Agee et al. |
| 2004/0260289 A1 | 12/2004 | Padget et al. |
| 2004/0260297 A1 | 12/2004 | Padget et al. |
| 2004/0267269 A1 | 12/2004 | Middleton et al. |
| 2005/0010231 A1 | 1/2005 | Myers |
| 2005/0015129 A1 | 1/2005 | Mische |
| 2005/0015154 A1 | 1/2005 | Lindsey et al. |
| 2005/0033366 A1 | 2/2005 | Cole et al. |
| 2005/0043733 A1 | 2/2005 | Eisermann et al. |
| 2005/0065522 A1 | 3/2005 | Orbay |
| 2005/0065523 A1 | 3/2005 | Orbay |
| 2005/0065524 A1 | 3/2005 | Orbay |
| 2005/0065526 A1 | 3/2005 | Drew et al. |
| 2005/0070902 A1 | 3/2005 | Medoff |
| 2005/0085813 A1 | 4/2005 | Spitler et al. |
| 2005/0085818 A1 | 4/2005 | Huebner |
| 2005/0085824 A1 | 4/2005 | Castaneda |
| 2005/0085921 A1 | 4/2005 | Gupta et al. |
| 2005/0113836 A1* | 5/2005 | Lozier ............... A61B 17/1617 606/80 |
| 2005/0113892 A1 | 5/2005 | Sproul |
| 2005/0113929 A1 | 5/2005 | Cragg et al. |
| 2005/0119749 A1 | 6/2005 | Lange |
| 2005/0124972 A1 | 6/2005 | Mische et al. |
| 2005/0125066 A1 | 6/2005 | Mcafee |
| 2005/0131407 A1 | 6/2005 | Sicvol et al. |
| 2005/0142163 A1 | 6/2005 | Hunter et al. |
| 2005/0143734 A1 | 6/2005 | Cachia et al. |
| 2005/0154331 A1 | 7/2005 | Christie et al. |
| 2005/0159749 A1 | 7/2005 | Levy et al. |
| 2005/0177172 A1 | 8/2005 | Acker et al. |
| 2005/0182399 A1 | 8/2005 | Levine |
| 2005/0192578 A1 | 9/2005 | Horst |
| 2005/0197537 A1 | 9/2005 | Bonadio et al. |
| 2005/0209557 A1 | 9/2005 | Carroll et al. |
| 2005/0216000 A1 | 9/2005 | Colleran et al. |
| 2005/0216007 A1 | 9/2005 | Woll et al. |
| 2005/0216008 A1 | 9/2005 | Zwirnmann et al. |
| 2005/0228391 A1 | 10/2005 | Levy et al. |
| 2005/0234472 A1 | 10/2005 | Huebner |
| 2005/0240188 A1 | 10/2005 | Chow et al. |
| 2005/0240190 A1 | 10/2005 | Gall et al. |
| 2005/0240193 A1 | 10/2005 | Layne et al. |
| 2005/0245928 A1 | 11/2005 | Colleran et al. |
| 2005/0251142 A1 | 11/2005 | Hoffmann et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0283159 A1 | 12/2005 | Amara |
| 2005/0288676 A1 | 12/2005 | Schnieders et al. |
| 2005/0288795 A1 | 12/2005 | Bagga et al. |
| 2006/0002980 A1 | 1/2006 | Ringeisen et al. |
| 2006/0004362 A1 | 1/2006 | Patterson et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0047787 A1 | 3/2006 | Agarwal et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064106 A1 | 3/2006 | Fernandez |
| 2006/0064164 A1 | 3/2006 | Thelen et al. |
| 2006/0064173 A1 | 3/2006 | Guederian et al. |
| 2006/0069392 A1 | 3/2006 | Renzi Brivio et al. |
| 2006/0079894 A1 | 4/2006 | Colleran et al. |
| 2006/0079905 A1 | 4/2006 | Beyar et al. |
| 2006/0085009 A1 | 4/2006 | Truckai et al. |

(56) References Cited

U.S. PATENT DOCUMENTS

| | | |
|---|---|---|
| 2006/0089647 A1 | 4/2006 | Culbert et al. |
| 2006/0089648 A1 | 4/2006 | Masini |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116773 A1 | 6/2006 | Cooney et al. |
| 2006/0122600 A1 | 6/2006 | Cole |
| 2006/0122610 A1 | 6/2006 | Culbert et al. |
| 2006/0142760 A1 | 6/2006 | McDonnel |
| 2006/0142858 A1 | 6/2006 | Colleran et al. |
| 2006/0149281 A1 | 7/2006 | Reiley et al. |
| 2006/0149379 A1 | 7/2006 | Kuslich et al. |
| 2006/0155289 A1 | 7/2006 | Windhager et al. |
| 2006/0173454 A1 | 8/2006 | Spitler et al. |
| 2006/0178737 A1 | 8/2006 | Furcht et al. |
| 2006/0184192 A1 | 8/2006 | Markworth et al. |
| 2006/0187748 A1 | 8/2006 | Kozyuk |
| 2006/0189994 A1 | 8/2006 | Wolford et al. |
| 2006/0195103 A1 | 8/2006 | Padget et al. |
| 2006/0200061 A1 | 9/2006 | Warkentine |
| 2006/0200140 A1 | 9/2006 | Lange |
| 2006/0200143 A1 | 9/2006 | Warburton |
| 2006/0217730 A1 | 9/2006 | Termanini |
| 2006/0229602 A1 | 10/2006 | Olsen |
| 2006/0235264 A1 | 10/2006 | Vassallo |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1 | 11/2006 | Edidin et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0012491 A1 | 1/2007 | Vasta |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0066480 A1 | 3/2007 | Moser et al. |
| 2007/0073342 A1 | 3/2007 | Stone et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123876 A1 | 5/2007 | Czartoski et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173838 A1 | 7/2007 | Li |
| 2007/0173839 A1 | 7/2007 | Running et al. |
| 2007/0173939 A1 | 7/2007 | Kim et al. |
| 2007/0179505 A1 | 8/2007 | Culbert |
| 2007/0198043 A1 | 8/2007 | Cox et al. |
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |
| 2007/0225726 A1 | 9/2007 | Dye et al. |
| 2007/0225810 A1 | 9/2007 | Colleran et al. |
| 2007/0233091 A1 | 10/2007 | Naifeh et al. |
| 2007/0233105 A1 | 10/2007 | Nelson et al. |
| 2007/0244485 A1 | 10/2007 | Greenhalgh et al. |
| 2007/0255287 A1 | 11/2007 | Rabiner |
| 2007/0270855 A1 | 11/2007 | Partin et al. |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009868 A1 | 1/2008 | Gotfried et al. |
| 2008/0009874 A1 | 1/2008 | Meridew et al. |
| 2008/0009875 A1* | 1/2008 | Sankaran ............ A61B 17/1617 606/84 |
| 2008/0009877 A1 | 1/2008 | Sankaran et al. |
| 2008/0012317 A1 | 1/2008 | Johnson |
| 2008/0015601 A1 | 1/2008 | Castro et al. |
| 2008/0019970 A1 | 1/2008 | Gorman |
| 2008/0021474 A1 | 1/2008 | Bonutti et al. |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0065140 A1 | 3/2008 | Bonutti |
| 2008/0071356 A1 | 3/2008 | Greenhalgh et al. |
| 2008/0077117 A1 | 3/2008 | Miller et al. |
| 2008/0077172 A1 | 3/2008 | Miller et al. |
| 2008/0077174 A1 | 3/2008 | Mische |
| 2008/0086133 A1 | 4/2008 | Kuslich et al. |
| 2008/0097332 A1 | 4/2008 | Greenhalgh et al. |
| 2008/0103501 A1 | 5/2008 | Ralph et al. |
| 2008/0103519 A1 | 5/2008 | Bonutti |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1 | 7/2008 | Saravia et al. |
| 2008/0161825 A1 | 7/2008 | Greenhalgh et al. |
| 2008/0167657 A1 | 7/2008 | Greenhalgh |
| 2008/0177261 A1 | 7/2008 | Mcminn |
| 2008/0183171 A1 | 7/2008 | Elghazaly et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208230 A1 | 8/2008 | Chin et al. |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0288003 A1 | 11/2008 | McKinley |

(56) References Cited

U.S. PATENT DOCUMENTS

| | | |
|---|---|---|
| 2008/0294163 A1 | 11/2008 | Chou et al. |
| 2008/0294166 A1 | 11/2008 | Goldin et al. |
| 2008/0294167 A1 | 11/2008 | Schumacher et al. |
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1 | 1/2009 | Chirico et al. |
| 2009/0012522 A1 | 1/2009 | Lob |
| 2009/0012564 A1 | 1/2009 | Chirico et al. |
| 2009/0018542 A1 | 1/2009 | Saravia et al. |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0048620 A1 | 2/2009 | Weiss et al. |
| 2009/0048629 A1 | 2/2009 | Rabiner |
| 2009/0048672 A1 | 2/2009 | Essenmacher |
| 2009/0054900 A1 | 2/2009 | Rabiner et al. |
| 2009/0076517 A1 | 3/2009 | Reiley et al. |
| 2009/0088752 A1 | 4/2009 | Metzinger et al. |
| 2009/0104586 A1 | 4/2009 | Cardoso et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131952 A1 | 5/2009 | Schumacher et al. |
| 2009/0131992 A1 | 5/2009 | Greenhalgh et al. |
| 2009/0138015 A1 | 5/2009 | Conner et al. |
| 2009/0143781 A1 | 6/2009 | Mische |
| 2009/0143827 A1 | 6/2009 | Levy et al. |
| 2009/0149890 A1 | 6/2009 | Martin |
| 2009/0149956 A1 | 6/2009 | Greenhalgh et al. |
| 2009/0157080 A1 | 6/2009 | Warburton |
| 2009/0163918 A1 | 6/2009 | Levy et al. |
| 2009/0177206 A1 | 7/2009 | Lozier et al. |
| 2009/0177239 A1 | 7/2009 | Castro |
| 2009/0216232 A1 | 8/2009 | Buford et al. |
| 2009/0228007 A1 | 9/2009 | Justin et al. |
| 2009/0228008 A1 | 9/2009 | Justin et al. |
| 2009/0275995 A1 | 11/2009 | Truckai et al. |
| 2009/0281628 A1 | 11/2009 | Oglaza |
| 2009/0292323 A1 | 11/2009 | Chirico et al. |
| 2009/0318981 A1 | 12/2009 | Kang |
| 2010/0023010 A1 | 1/2010 | Nelson et al. |
| 2010/0087821 A1 | 4/2010 | Trip et al. |
| 2010/0094292 A1 | 4/2010 | Parrott |
| 2010/0094347 A1 | 4/2010 | Nelson et al. |
| 2010/0100184 A1 | 4/2010 | Krueger et al. |
| 2010/0114181 A1 | 5/2010 | Lob |
| 2010/0131019 A1 | 5/2010 | Lob |
| 2010/0137862 A1 | 6/2010 | Diao et al. |
| 2010/0145397 A1 | 6/2010 | Overes et al. |
| 2010/0161061 A1 | 6/2010 | Hunt |
| 2010/0222884 A1 | 9/2010 | Greenhalgh |
| 2010/0241120 A1 | 9/2010 | Bledsoe et al. |
| 2010/0241123 A1 | 9/2010 | Middleton et al. |
| 2010/0241176 A1 | 9/2010 | Lob |
| 2010/0249785 A1 | 9/2010 | Betts |
| 2010/0286481 A1 | 11/2010 | Sharp et al. |
| 2010/0286692 A1 | 11/2010 | Greenhalgh et al. |
| 2011/0077650 A1 | 3/2011 | Braun et al. |
| 2011/0087227 A1 | 4/2011 | Mazur et al. |
| 2011/0137313 A1 | 6/2011 | Jensen et al. |
| 2011/0144645 A1 | 6/2011 | Saravia et al. |
| 2011/0178520 A1 | 7/2011 | Taylor et al. |
| 2011/0218585 A1 | 9/2011 | Krinke et al. |
| 2011/0282346 A1 | 11/2011 | Pham et al. |
| 2011/0295255 A1 | 12/2011 | Roberts et al. |
| 2011/0306975 A1 | 12/2011 | Kaikkonen et al. |
| 2011/0307021 A1 | 12/2011 | Anderson et al. |
| 2011/0307072 A1 | 12/2011 | Anderson et al. |
| 2011/0313537 A1 | 12/2011 | Anderson et al. |
| 2012/0029633 A1 | 2/2012 | Anderson et al. |
| 2012/0065638 A1 | 3/2012 | Moore |
| 2012/0152872 A1 | 6/2012 | Didehvar |
| 2012/0179161 A1 | 7/2012 | Rains et al. |
| 2012/0209273 A1 | 8/2012 | Zaretzka et al. |
| 2012/0232533 A1 | 9/2012 | Veldman et al. |
| 2012/0239038 A1 | 9/2012 | Saravia et al. |
| 2012/0253410 A1 | 10/2012 | Taylor et al. |
| 2013/0006245 A1 | 1/2013 | Stoneburner et al. |
| 2013/0012942 A1 | 1/2013 | Nelson et al. |
| 2013/0116693 A1 | 5/2013 | Nelson et al. |
| 2013/0165935 A1 | 6/2013 | Griffiths et al. |
| 2013/0231665 A1 | 9/2013 | Saravia et al. |
| 2013/0267953 A1 | 10/2013 | Brenzel et al. |
| 2014/0031823 A1 | 1/2014 | Mazur et al. |
| 2014/0058390 A1 | 2/2014 | Taylor et al. |
| 2014/0074093 A9 | 3/2014 | Nelson et al. |
| 2014/0088707 A1 | 3/2014 | Donner et al. |
| 2014/0128870 A1 | 5/2014 | Brenzel et al. |
| 2014/0200618 A1 | 7/2014 | Donner et al. |
| 2015/0141996 A1 | 5/2015 | Taylor et al. |
| 2015/0164514 A1 | 6/2015 | Wlodarski et al. |
| 2015/0320459 A1 | 11/2015 | Brenzel et al. |
| 2016/0128703 A1 | 5/2016 | Wlodarski et al. |

FOREIGN PATENT DOCUMENTS

| | | |
|---|---|---|
| CA | 2609175 A1 | 12/2005 |
| CA | 2537171 C | 8/2007 |
| CA | 2669737 A1 | 5/2008 |
| CA | 2670263 A1 | 5/2008 |
| CA | 2670438 A1 | 5/2008 |
| CA | 2678911 A1 | 9/2008 |
| CA | 2685046 A1 | 11/2008 |
| CA | 2727453 A1 | 12/2009 |
| CA | 2738478 A1 | 4/2010 |
| CN | 2326199 | 6/1999 |
| CN | 1530079 | 9/2004 |
| CN | 1533260 A | 9/2004 |
| CN | 2699849 Y | 5/2005 |
| CN | 1909848 A | 2/2007 |
| CN | 100379388 | 4/2008 |
| CN | 101208053 A | 6/2008 |
| CN | 101404946 | 4/2009 |
| CN | 101636119 A | 1/2010 |
| DE | 923085 | 7/1949 |
| DE | 3146065 A1 | 5/1983 |
| DE | 3234875 A1 | 3/1984 |
| DE | 198800197 U1 | 8/1988 |
| DE | 3922044 A1 | 2/1991 |
| DE | 4217236 | 11/1993 |
| DE | 202006017194 U1 | 2/2007 |
| DE | 102006016213 | 10/2007 |
| EP | 0145166 A2 | 6/1985 |
| EP | 145166 A2 | 6/1985 |
| EP | 145166 A3 | 8/1986 |
| EP | 253526 A1 | 1/1988 |
| EP | 263292 A1 | 4/1988 |
| EP | 275871 A1 | 7/1988 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 442137 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 611560 A1 | 8/1994 |
| EP | 745352 A2 | 12/1996 |
| EP | 546162 B1 | 9/1997 |
| EP | 807419 A2 | 11/1997 |
| EP | 819413 A2 | 1/1998 |
| EP | 931513 A2 | 7/1999 |
| EP | 0941037 | 9/1999 |
| EP | 0941037 B1 | 9/1999 |
| EP | 1099412 A2 | 5/2001 |
| EP | 1132051 A2 | 9/2001 |
| EP | 674495 B1 | 11/2001 |
| EP | 1155661 A1 | 11/2001 |

(56) References Cited

FOREIGN PATENT DOCUMENTS

| | | |
|---|---|---|
| EP | 1203569 A1 | 5/2002 |
| EP | 900065 B1 | 6/2002 |
| EP | 1277442 A2 | 1/2003 |
| EP | 1300122 A2 | 4/2003 |
| EP | 1348384 A2 | 10/2003 |
| EP | 1354562 | 10/2003 |
| EP | 1372496 A1 | 1/2004 |
| EP | 1391186 A1 | 2/2004 |
| EP | 1098600 B1 | 3/2004 |
| EP | 1277442 A3 | 3/2004 |
| EP | 1396231 A1 | 3/2004 |
| EP | 1410765 A2 | 4/2004 |
| EP | 1442718 A1 | 8/2004 |
| EP | 1442729 A1 | 8/2004 |
| EP | 1454592 A2 | 9/2004 |
| EP | 1459686 A2 | 9/2004 |
| EP | 1484077 A2 | 12/2004 |
| EP | 1079752 B1 | 1/2005 |
| EP | 1484077 A3 | 1/2005 |
| EP | 1495729 A1 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1563795 A1 | 8/2005 |
| EP | 1582159 A1 | 10/2005 |
| EP | 1582160 A1 | 10/2005 |
| EP | 1582161 A1 | 10/2005 |
| EP | 1582162 A1 | 10/2005 |
| EP | 1582163 A1 | 10/2005 |
| EP | 1582164 A1 | 10/2005 |
| EP | 1634548 A2 | 3/2006 |
| EP | 1639953 A1 | 3/2006 |
| EP | 1669035 A1 | 6/2006 |
| EP | 1073371 B1 | 8/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 1787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1905367 A1 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1277442 B1 | 7/2008 |
| EP | 1972308 A1 | 9/2008 |
| EP | 1987785 A2 | 11/2008 |
| EP | 2014261 A1 | 1/2009 |
| EP | 2025292 A1 | 2/2009 |
| EP | 1459689 B1 | 4/2009 |
| EP | 1484077 B1 | 6/2009 |
| EP | 1073371 B2 | 7/2009 |
| EP | 1459689 B3 | 11/2009 |
| ES | 2251888 | 5/2006 |
| FR | 2653006 A1 | 4/1991 |
| FR | 2686788 | 8/1993 |
| FR | 2781360 | 1/2000 |
| FR | 2861576 | 5/2005 |
| GB | 2173565 A | 10/1986 |
| GB | 2268068 A | 1/1994 |
| GB | 2274993 | 8/1994 |
| JP | 1310664 A | 12/1989 |
| JP | 2000287983 | 10/2000 |
| JP | 2007125386 | 5/2007 |
| JP | 2008500140 A | 1/2008 |
| JP | 2008540037 A | 11/2008 |
| JP | 2010510040 A | 4/2010 |
| JP | 2010510041 A | 4/2010 |
| JP | 2010510042 A | 4/2010 |
| JP | 2010522046 A | 7/2010 |
| JP | 2010524642 A | 7/2010 |
| JP | 2011523889 A | 8/2011 |
| JP | 2012504027 A | 2/2012 |
| RU | 2004104359 A | 2/2005 |
| WO | WO8904150 A1 | 5/1989 |
| WO | WO8907056 A1 | 8/1989 |
| WO | WO9003764 A1 | 4/1990 |
| WO | WO9011726 A1 | 10/1990 |
| WO | WO91/02493 A1 | 3/1991 |
| WO | WO9106260 A1 | 5/1991 |
| WO | WO9106265 A1 | 5/1991 |
| WO | WO9111962 A1 | 8/1991 |
| WO | WO9119461 A1 | 12/1991 |
| WO | WO9937219 A1 | 7/1994 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO9514433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO9618354 A2 | 6/1996 |
| WO | WO9618354 A3 | 8/1996 |
| WO | WO9625118 A1 | 8/1996 |
| WO | WO9640476 A1 | 12/1996 |
| WO | WO9703611 A1 | 2/1997 |
| WO | WO9703611 A1 | 2/1997 |
| WO | WO9718775 A1 | 5/1997 |
| WO | WO9742602 A1 | 11/1997 |
| WO | WO9742912 A1 | 11/1997 |
| WO | WO9747251 A1 | 12/1997 |
| WO | WO9801077 A1 | 1/1998 |
| WO | WO9805261 A2 | 2/1998 |
| WO | WO9807392 A1 | 2/1998 |
| WO | WO9819616 A1 | 5/1998 |
| WO | WO9824380 A1 | 6/1998 |
| WO | WO9826725 A1 | 6/1998 |
| WO | WO9838918 A1 | 9/1998 |
| WO | WO9846169 A1 | 10/1998 |
| WO | WO9856301 A1 | 12/1998 |
| WO | WO9922661 A1 | 5/1999 |
| WO | WO9922662 A1 | 5/1999 |
| WO | WO9947055 A1 | 9/1999 |
| WO | WO9951149 A1 | 10/1999 |
| WO | WO9953843 A1 | 10/1999 |
| WO | WO9955248 A1 | 11/1999 |
| WO | WO9962416 A1 | 12/1999 |
| WO | WO0006037 A1 | 2/2000 |
| WO | WO0009024 A1 | 2/2000 |
| WO | WO0012036 A1 | 3/2000 |
| WO | WO0012036 A1 | 3/2000 |
| WO | WO0021455 A1 | 4/2000 |
| WO | WO0025681 A1 | 5/2000 |
| WO | WO0028906 A1 | 5/2000 |
| WO | WO0030551 A1 | 6/2000 |
| WO | WO0030569 A1 | 6/2000 |
| WO | WO0038586 A1 | 7/2000 |
| WO | WO0042954 A2 | 7/2000 |
| WO | WO0044319 A1 | 8/2000 |
| WO | WO0044321 A2 | 8/2000 |
| WO | WO0044946 A1 | 8/2000 |
| WO | WO0045712 A1 | 8/2000 |
| WO | WO0045714 A1 | 8/2000 |
| WO | WO0045715 A1 | 8/2000 |
| WO | WO0045722 A1 | 8/2000 |
| WO | WO0047119 A1 | 8/2000 |
| WO | WO0048534 A1 | 8/2000 |
| WO | WO0071038 A1 | 11/2000 |
| WO | WO0076414 A1 | 12/2000 |
| WO | WO0108571 A1 | 2/2001 |

(56) References Cited

FOREIGN PATENT DOCUMENTS

| | | |
|---|---|---|
| WO | WO0128443 A1 | 4/2001 |
| WO | WO0134045 A1 | 5/2001 |
| WO | WO0149193 A1 | 7/2001 |
| WO | WO0154598 A1 | 8/2001 |
| WO | WO0160268 A1 | 8/2001 |
| WO | WO0160268 A1 | 8/2001 |
| WO | WO0176493 A1 | 10/2001 |
| WO | WO0176514 A2 | 10/2001 |
| WO | WO0178015 A2 | 10/2001 |
| WO | WO0180751 A1 | 11/2001 |
| WO | WO0185042 A1 | 11/2001 |
| WO | WO0213700 A2 | 2/2002 |
| WO | WO0213716 A1 | 2/2002 |
| WO | WO0217794 A1 | 3/2002 |
| WO | WO0217794 A1 | 3/2002 |
| WO | WO0224088 A2 | 3/2002 |
| WO | WO0234107 A2 | 5/2002 |
| WO | WO0234148 A2 | 5/2002 |
| WO | WO0237935 A2 | 5/2002 |
| WO | WO0245606 A1 | 6/2002 |
| WO | WO0249517 A1 | 6/2002 |
| WO | WO02058575 A1 | 8/2002 |
| WO | WO0267824 A2 | 9/2002 |
| WO | WO02078555 A1 | 10/2002 |
| WO | WO02089683 A1 | 11/2002 |
| WO | WO0296306 A1 | 12/2002 |
| WO | WO03007830 A1 | 1/2003 |
| WO | WO03013336 A2 | 2/2003 |
| WO | WO0217794 A8 | 3/2003 |
| WO | WO03030760 A1 | 4/2003 |
| WO | WO03043488 A2 | 5/2003 |
| WO | WO03045257 A2 | 6/2003 |
| WO | WO03047440 A2 | 6/2003 |
| WO | WO03068090 A1 | 8/2003 |
| WO | WO0217794 A9 | 9/2003 |
| WO | WO2004008949 A2 | 1/2004 |
| WO | WO2004017817 A2 | 3/2004 |
| WO | WO2004021904 | 3/2004 |
| WO | WO2004030549 A1 | 4/2004 |
| WO | WO2004039271 | 5/2004 |
| WO | WO2004064603 A2 | 8/2004 |
| WO | WO2004078220 A2 | 9/2004 |
| WO | WO2004078221 A2 | 9/2004 |
| WO | WO2004086934 A2 | 10/2004 |
| WO | WO2004092431 A1 | 10/2004 |
| WO | WO2004093633 A2 | 11/2004 |
| WO | WO2004098453 A2 | 11/2004 |
| WO | WO2004103209 A2 | 12/2004 |
| WO | WO2004110292 A2 | 12/2004 |
| WO | WO2004110300 A2 | 12/2004 |
| WO | WO2004112661 A1 | 12/2004 |
| WO | WO2005000159 A2 | 1/2005 |
| WO | WO2005020830 A1 | 3/2005 |
| WO | WO2005020833 A2 | 3/2005 |
| WO | WO2005023085 A2 | 3/2005 |
| WO | WO2005032326 A2 | 4/2005 |
| WO | WO2005032340 A2 | 4/2005 |
| WO | WO2005041799 A1 | 5/2005 |
| WO | WO2005044122 A1 | 5/2005 |
| WO | WO2005039651 A2 | 6/2005 |
| WO | WO2005051971 A1 | 6/2005 |
| WO | WO2005055874 A2 | 6/2005 |
| WO | WO2005020833 A3 | 7/2005 |
| WO | WO2005070314 A1 | 8/2005 |
| WO | WO2005092223 A2 | 10/2005 |
| WO | WO2005094693 A1 | 10/2005 |
| WO | WO2005094705 A2 | 10/2005 |
| WO | WO2005094706 A1 | 10/2005 |
| WO | WO2005096975 A2 | 10/2005 |
| WO | WO2005102196 A1 | 11/2005 |
| WO | WO2005107415 A2 | 11/2005 |
| WO | WO2005112804 A1 | 12/2005 |
| WO | WO2005112804 A1 | 12/2005 |
| WO | WO2005122931 A1 | 12/2005 |
| WO | WO2005122932 A2 | 12/2005 |
| WO | WO2005123171 A2 | 12/2005 |
| WO | WO2006011152 A2 | 2/2006 |
| WO | WO2006020530 A2 | 2/2006 |
| WO | WO2005112804 A9 | 3/2006 |
| WO | WO2006023793 A2 | 3/2006 |
| WO | WO2006026323 A2 | 3/2006 |
| WO | WO2006026323 A2 | 3/2006 |
| WO | WO2006026323 A9 | 4/2006 |
| WO | WO2006041460 A1 | 4/2006 |
| WO | WO2006041460 A1 | 4/2006 |
| WO | WO2006042188 A2 | 4/2006 |
| WO | WO2006042189 A2 | 4/2006 |
| WO | WO2006042334 A2 | 4/2006 |
| WO | WO2006034396 A3 | 5/2006 |
| WO | WO2006051547 A2 | 5/2006 |
| WO | WO2006055448 A1 | 5/2006 |
| WO | WO2006063083 A1 | 6/2006 |
| WO | WO2006066228 A2 | 6/2006 |
| WO | WO2006068682 A1 | 6/2006 |
| WO | WO2010065855 A1 | 6/2006 |
| WO | WO2006089929 A1 | 8/2006 |
| WO | WO2006090379 A2 | 8/2006 |
| WO | WO2006034436 A3 | 10/2006 |
| WO | WO2006108067 A2 | 10/2006 |
| WO | WO2006113800 A2 | 10/2006 |
| WO | 2608693 A1 | 11/2006 |
| WO | WO2006116760 A2 | 11/2006 |
| WO | WO2006116761 A2 | 11/2006 |
| WO | WO2006124764 A1 | 11/2006 |
| WO | WO2006124764 A1 | 11/2006 |
| WO | WO2006124937 A2 | 11/2006 |
| WO | WO2006127904 A1 | 11/2006 |
| WO | WO2006127904 A1 | 11/2006 |
| WO | WO2007002933 A2 | 1/2007 |
| WO | WO2007008177 A1 | 1/2007 |
| WO | WO2007009107 A2 | 1/2007 |
| WO | WO2007009123 A2 | 1/2007 |
| WO | WO2007011994 A2 | 1/2007 |
| WO | WO2007012046 A2 | 1/2007 |
| WO | WO2007025236 A2 | 3/2007 |
| WO | WO2007040949 A2 | 4/2007 |
| WO | WO2007041665 A2 | 4/2007 |
| WO | WO2006124937 A3 | 5/2007 |
| WO | WO2007053960 A1 | 5/2007 |
| WO | WO2007058943 A2 | 5/2007 |
| WO | WO2007059243 A1 | 5/2007 |
| WO | WO2007059243 A1 | 5/2007 |
| WO | WO2007059246 A1 | 5/2007 |
| WO | WO2007059259 A1 | 5/2007 |
| WO | WO2007059259 A1 | 5/2007 |
| WO | WO2007065137 A2 | 6/2007 |
| WO | WO2007069251 A2 | 6/2007 |
| WO | WO2007073488 A2 | 6/2007 |
| WO | WO2007076308 A2 | 7/2007 |
| WO | WO2007076374 A2 | 7/2007 |
| WO | WO2007076376 A2 | 7/2007 |
| WO | WO2007076377 A2 | 7/2007 |
| WO | WO2007078692 A2 | 7/2007 |
| WO | WO2007079237 A2 | 7/2007 |
| WO | WO2007082151 A1 | 7/2007 |
| WO | WO2007084239 A2 | 7/2007 |
| WO | WO2007092813 A2 | 8/2007 |
| WO | WO2007092813 A2 | 8/2007 |
| WO | WO2007092841 A2 | 8/2007 |
| WO | WO2007092841 A2 | 8/2007 |
| WO | WO2007036815 A2 | 9/2007 |
| WO | WO2007114982 A1 | 10/2007 |
| WO | WO2007115108 A1 | 10/2007 |
| WO | WO2007117571 A2 | 10/2007 |
| WO | WO2007120539 A2 | 10/2007 |
| WO | WO2007092841 A3 | 11/2007 |
| WO | WO2007124130 A2 | 11/2007 |
| WO | WO2007127255 A2 | 11/2007 |
| WO | WO2007127260 A2 | 11/2007 |
| WO | WO2007131002 A2 | 11/2007 |
| WO | WO2007134134 A2 | 11/2007 |
| WO | WO2007079237 A3 | 12/2007 |
| WO | WO2007145824 A2 | 12/2007 |
| WO | WO2008004229 A2 | 1/2008 |

(56) References Cited

FOREIGN PATENT DOCUMENTS

| | | |
|---|---|---|
| WO | WO2008006117 A2 | 1/2008 |
| WO | WO2008016910 A2 | 2/2008 |
| WO | WO2008019397 A2 | 2/2008 |
| WO | WO2008035849 A1 | 3/2008 |
| WO | WO2008037454 A1 | 4/2008 |
| WO | WO2008043254 A1 | 4/2008 |
| WO | WO2008058960 A2 | 5/2008 |
| WO | WO2008059027 A2 | 5/2008 |
| WO | WO2008060277 A2 | 5/2008 |
| WO | WO2008060277 A2 | 5/2008 |
| WO | WO2008063265 A1 | 5/2008 |
| WO | WO2008064346 A2 | 5/2008 |
| WO | WO2008064347 A2 | 5/2008 |
| WO | WO2008064347 A2 | 5/2008 |
| WO | WO2008064350 A2 | 5/2008 |
| WO | WO2008076330 A1 | 6/2008 |
| WO | WO2008076330 A1 | 6/2008 |
| WO | WO2008076357 A1 | 6/2008 |
| WO | WO2008094407 A1 | 8/2008 |
| WO | WO2007011353 A3 | 9/2008 |
| WO | WO2007092813 A3 | 9/2008 |
| WO | WO2008109566 A1 | 9/2008 |
| WO | WO2008112308 A1 | 9/2008 |
| WO | WO2008116170 A2 | 9/2008 |
| WO | WO2008116175 A2 | 9/2008 |
| WO | WO2008118945 A1 | 10/2008 |
| WO | WO2008121608 A2 | 10/2008 |
| WO | WO2008132728 A1 | 11/2008 |
| WO | WO2008134287 A2 | 11/2008 |
| WO | WO2008134758 A1 | 11/2008 |
| WO | WO2008139456 A2 | 11/2008 |
| WO | WO2008144709 A2 | 11/2008 |
| WO | WO2008144709 A2 | 11/2008 |
| WO | WO2007078692 A3 | 12/2008 |
| WO | WO2008121608 A3 | 1/2009 |
| WO | WO2008134287 A3 | 1/2009 |
| WO | WO2009006622 A2 | 1/2009 |
| WO | WO2009007331 A2 | 1/2009 |
| WO | WO2009009772 A1 | 1/2009 |
| WO | WO2009010412 A1 | 1/2009 |
| WO | WO2009012347 A1 | 1/2009 |
| WO | WO2009026070 A1 | 2/2009 |
| WO | WO2009027325 A1 | 3/2009 |
| WO | WO2009039430 A1 | 3/2009 |
| WO | WO2006026323 A3 | 4/2009 |
| WO | WO2006026397 A3 | 4/2009 |
| WO | WO2009045751 A1 | 4/2009 |
| WO | WO2009067568 | 5/2009 |
| WO | WO2009659227 A1 | 5/2009 |
| WO | WO2009072125 A1 | 6/2009 |
| WO | WO2009076086 A1 | 6/2009 |
| WO | WO2008144709 A3 | 7/2009 |
| WO | WO2009088376 A1 | 7/2009 |
| WO | WO2009094478 A1 | 7/2009 |
| WO | WO2008060277 A3 | 9/2009 |
| WO | WO2008112912 A3 | 9/2009 |
| WO | WO2009132333 A2 | 10/2009 |
| WO | WO2009143374 A2 | 11/2009 |
| WO | WO2009143496 A1 | 11/2009 |
| WO | WO2008112875 A3 | 12/2009 |
| WO | WO2009146457 A1 | 12/2009 |
| WO | WO2009152270 A1 | 12/2009 |
| WO | WO2009152272 A1 | 12/2009 |
| WO | WO2009152273 A1 | 12/2009 |
| WO | WO2009132333 A3 | 1/2010 |
| WO | WO2010/017990 | 2/2010 |
| WO | WO2008139456 A3 | 2/2010 |
| WO | WO2010037038 A2 | 4/2010 |
| WO | WO2010056895 A1 | 5/2010 |
| WO | WO2010062379 A1 | 6/2010 |
| WO | WO2010091242 A1 | 8/2010 |
| WO | WO2010035156 A1 | 11/2010 |

OTHER PUBLICATIONS

US 7,201,752, 04/2007, Huebner et al. (withdrawn)
International Search Report for International Application No. PCT/US14/69907, dated Jun. 4, 2015.
Written Opinion for International Application No. PCT/US14/69907, dated Jun. 4, 2015.
European Patent Office, Supplementary European Search Report, European Patent Application No. 11735124, dated Aug. 28, 2015.
State Intellectual Property Office of China, Second Official Action, Chinese Patent Application No. 201180013862.2, dated May 13, 2015.
App No. PCT/US2012/028145 International Search Report, dated Sep. 13, 2012.
App No. PCT/US2012/028145 Written Opinion of the International Searching Authority, dated Sep. 13, 2012.
Ilyas, Asif M., "Intramedullary Fixation of Distal Radius Fractures," Elsevier, Inc. on behalf of the American Society for Surgery of the Hand, New York, New York, Feb. 2009.
Figl, Markus, et al., "Volar Fixed-Angle Plate Osteosynthesis of Unstable Distal Radius Fractures: 12 Months Results," Springer, New York, New York, Feb. 19, 2009.
Photograph, OrthopaedicLIST, 2010, Wilmington, North Carolina.
Non Final Office Action in U.S. Appl. No. 14/492,599, dated Sep. 22, 2015.
Final Office Action in U.S. Appl. No. 14/492,599, dated Jun. 16, 2016.
App No. PCT/US2011/021735 International Search Report, dated May 25, 2011.
App No. PCT/US2011/021735 Written Opinion of the International Searching Authority, dated May 25, 2011.
App No. PCT/US 09/30971 International Search Report, dated Mar. 6, 2009.
App No. PCT/US 09/30971 Written Opinion of the International Searching Authority, dated Mar. 6, 2009.
Barnes, C. Lowry, et al., "Advanced Core Decompression System," Wright, 2008, Arlington, Tennessee.
"OptiMesh 1500E—Percutaneous Interbody Fusion Surgical Technique," Spineology Inc., Feb. 2010, Saint Paul, Minnesota.
Corti, G., et al., "Acute Vertebral Body Compression Fracture treated with OptiMesh—Indications, Applications and First Clinical Results," Eurospine, 2005, Uster-Zürich Switzerland.
Advanced Core Decompression System—Surgical Technique, Wright, 2010, Arlington, Tennessee.
State Intellectual Property Office of China, First Office Action, Chinese Patent Application No. 201180013862.2, Aug. 8, 2014.
State Intellectual Property Office of China, First Search Report, Chinese Patent Application No. 201180013862.2, Aug. 8, 2014.
App No. PCT/US2011/027602 International Search Report, dated Jul. 5, 2011.
App No. PCT/US2011/027602 Written Opinion of the International Searching Authority, dated Jul. 5, 2011.
App No. PCT/US2011/21074 International Search Report, dated May 23, 2011.
App No. PCT/US2011/21074 Written Opinion of the International Searching Authority, dated May 23, 2011.
App No. PCT/US2011/027597 International Search Report, dated Jul. 6, 2011.
App No PCT/US2011/027597 Written Opinion of the International Searching Authority, dated Jul. 6, 2011
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.

(56) References Cited

OTHER PUBLICATIONS

Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal Orthopedic Trauma, vol. 22, No. 8, Supplement, Philadelphia, Pennsylvania, Sep. 2008.
Arora, Rohit, et al., "A Representative Case of Osteoporotic Ditsal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadelphia, Pennsylvania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al., "Wrist Fractures in Osteoporotic Patients," The Journal of Orthopedic Trauma, vol. 22, No. 8, Supplement, Philadelphia, Pennsylvania, Sep. 2008.
Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis-Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G01498, Needham, Massachusetts, Jan. 1, 2009.
State Intellectual Property Office of the People's Republic of China Office Action in Application No. 201510621438.6, Apr. 1, 2017.

* cited by examiner

APPARATUS AND METHODS FOR BONE ACCESS AND CAVITY PREPARATION

CROSS-REFERENCE TO RELATED APPLICATIONS

This application is a continuation of U.S. patent application Ser. No. 14/594,482, filed on Jan. 12, 2015, which is a continuation of U.S. patent application Ser. No. 13/009,657, filed on Jan. 19, 2011, now U.S. Pat. No. 8,961,518, which is a nonprovisional of U.S. Provisional Applications Nos. 61/296,722, filed on Jan. 20, 2010, and 61/389,507, filed on Oct. 4, 2010, all of which are hereby incorporated by reference herein in their entireties.

FIELD OF TECHNOLOGY

Aspects of the disclosure relate to providing apparatus and methods for repairing bone fractures. In particular, the disclosure relates to apparatus and methods for repairing bone fractures utilizing a device that is inserted into a bone.

BACKGROUND

Bone fracture fixation may involve using a structure to counteract or partially counteract forces on a fractured bone or associated bone fragments. In general, fracture fixation may provide longitudinal (along the long axis of the bone), transverse (across the long axis of the bone), and rotational (about the long axis of the bone) stability. Fracture fixation may also preserve normal biologic and healing function.

Bone fracture fixation often involves addressing loading conditions, fracture patterns, alignment, compression force, and other factors, which may differ for different types of fractures. For example, midshaft fractures may have ample bone material on either side of the fracture in which anchors may be driven. End-bone fractures, especially on the articular surface may have thin cortical bone, soft cancellous bone, and relatively fewer possible anchoring locations. Typical bone fracture fixation approaches may involve one or both of: (1) a device that is within the skin (internal fixation); and (2) a device that extends out of the skin (external fixation).

Internal fixation approaches typically involve one or both of: (a) a plate that is screwed to the outside of the bone; and (b) an implant that is inserted inside the bone.

Plates are often characterized by relatively invasive surgery, support of fractured bone segments from one side outside of bone, and screws that anchor into the plate and the bone.

Implants may include intramedullary rods or nails, such as those used in mid shaft treatments. The typical intramedullary rod or nail is fixed in diameter and is introduced into the medullary canal through an incision. Flexible intramedullary rod-like solutions utilize structures that can be inserted into the medullary cavity through an access site and then be made rigid. The flexible structures may be reinforced with polymers or cements. Multi-segment fractures, of either the midshaft or end-bone, may require alignment and stability in a manner that generates adequate fixation in multiple directions. Implants may be used to treat midshaft fractures and end-bone fractures.

Implant-based therapies may involve removing bone tissue from the interior of the bone to prepare the interior for the implant. Preparation for the implant may involve providing a space in the bone interior for reception of the implant.

Proper location, size, shape, orientation and proximity to bone fragments and anatomical features, among other factors, may increase the therapeutic effectiveness of the implant.

It would be desirable, therefore, to provide apparatus and methods for preparation of a bone interior.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
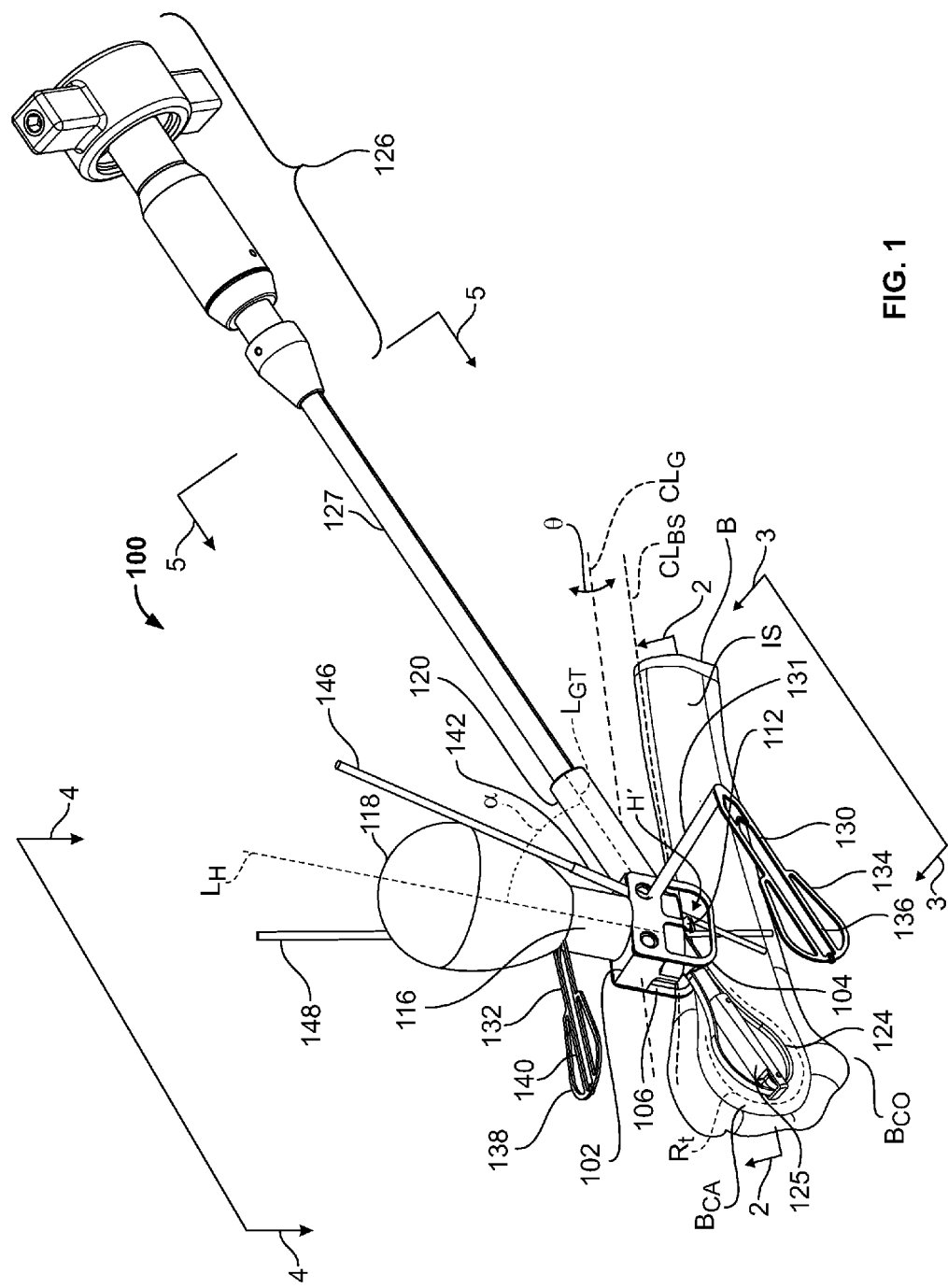
FIG. 1 shows illustrative apparatus in accordance with principles of the invention.

Apparatus and methods for preparing the interior of a bone for therapy are provided. The therapy may include therapy for a bone fracture. The apparatus and methods may involve orienting a surgical instrument for proper deployment in the interior of the bone. The surgical instrument may provide access from outside the bone to the interior of the bone. The surgical instrument may prepare the interior to receive a therapeutic device. The surgical instrument may include a therapeutic device.

Apparatus and methods for positioning a surgical instrument relative to exterior features of a bone are provided. The apparatus may be a surgical instrument guide.

The surgical instrument may be a device for repairing the bone. The surgical instrument may be a prosthetic device. For example, the surgical instrument may include one or more of the features of devices that are shown and described in U.S. Patent Application Publication No. 2009/0182336A1, which is hereby incorporated by reference herein in its entirety. The surgical instrument may be for accessing an interior region of the bone. For example, the surgical instrument may be a bone saw. The surgical instrument may be a drill. The surgical instrument may be for preparing the interior region of the bone to receive a therapeutic device. For example, the surgical instrument may be a broach.

The surgical instrument may have a portion that is configured to be positioned in a targeted region inside the bone.

The bone may have a surface. The surface may have a normal axis. The normal axis may be substantially perpendicular to the surface. The surface may have an anterior-posterior axis. The anterior-posterior axis may extend in a direction that is substantially normal to the anterior and posterior sides of the bone. The surface may have a proximal-distal axis. The proximal-distal axis may extend in a direction that is substantially along the bone. The bone surface may have curvature. The curvature may define a curvature axis. The curvature may be circumferential around the bone. The curvature axis may be parallel or near parallel with the proximal-distal axis.

The surgical instrument guide may include a bottom index. The bottom index may provide for aligning the device at a position along the surface normal axis. The position may be flush with the surface. The bottom index may be a bottom surface of the device. The bottom index may be one or more features that project from the bottom surface of the device.

The surgical instrument guide may include first and second lateral extensions. The first lateral extension may be configured to respond to an anterior contour of the bone. The anterior contour may be a contour on the anterior side of the bone. The second lateral extension may be configured to respond to a posterior contour of the bone. The posterior contour may be a contour on the posterior side of the bone. The first and second lateral extensions may provide for aligning the device along the anterior-posterior axis.

The surgical instrument guide may include a distal index. The distal index may be configured to provide visual alignment along the proximal-distal axis.

In some embodiments, the surgical instrument guide may include a first bone contactor. The first bone contactor may be configured to engage the surface. The apparatus may include a second bone contactor. The second bone contactor may be configured to engage the surface. When the first and second bone contactors engage the surface, the first and second contactors resist rotation about the surface normal axis.

In some embodiments, the first and second bone contactors may be configured to penetrate the surface.

In some embodiments, the surgical instrument guide may include first and second lateral cleats. The first lateral cleat may be configured to engage an anterior portion of the bone. The second lateral cleat may be configured to engage a posterior portion of the bone. When the first and second lateral cleats are engaged in the bone, the first and second lateral cleats may resist rotation about the proximal-distal axis of the bone.

The surgical instrument guide may include an instrument guide member. The surgical instrument guide may include an aligning member. The aligning member may be configured to align the guide member with the bone. The surgical instrument guide may include a base member. The base member may support the aligning member.

In some embodiments, the surgical instrument guide may include a lateral cleat. The lateral cleat may be configured to resist movement of the base member in a direction along the circumference of the elongated bone. The lateral cleat may include a stem that is directly fixed to the base.

In some embodiments, the surgical instrument guide may include a bone contactor. The bone contactor may be configured to resist rotation of the base about an axis that is substantially normal to the surface.

In some embodiments, the bone contactor may be a first bone contactor and the surgical instrument guide may include a second bone contactor. The first and second bone contactors may extend from a surface of the base. The first and second bone contactors may be configured to contact the bone surface along the curvature axis of the bone surface.

In some embodiments, the surgical instrument guide may include a handle support and a grip. The grip may be rotatable relative to the handle support when a torque greater than a threshold torque is applied to the grip.

In some embodiments, the surgical instrument guide may include an alignment template. The alignment template may be configured to register the instrument guide member to a target region inside the bone.

In some embodiments, the instrument template may include a dimension that corresponds to a dimension of a surgical instrument that is configured for deployment in the bone interior through the instrument guide member.

In some embodiments, the template may include a fluoroscopically detectable material.

In some embodiments, the template may be fixed to the base. The template may map to a lateral view plane in the cavity.

In some embodiments, the template may map to an anterior-posterior view plane in the cavity.

In some embodiments, the surgical instrument guide may include a first template that maps to the lateral view plane and a second template that maps to the anterior-posterior view plane.

In some embodiments, the surgical instrument guide may include a channel. The channel may be configured to direct an elongated fixation member into the bone. The elongated fixation member may be a wire. The wire may be a k-wire. The elongated fixation member may be a rod. The rod may be a threaded rod.

In some embodiments, the surgical instrument guide may include a first channel and a second channel. The first and second channels may be configured to direct first and second elongated fixation members into the bone.

In some embodiments, the first and second channels may be oblique to each other.

The methods may include a method for performing a procedure in a bone interior. The method may include positioning an instrument template outside the bone interior at a position that corresponds to a target region inside the bone. The method may include generating an electronic image showing the instrument template and the target region. The method may include delivering an instrument to the target region.

In some embodiments, the delivering may include arranging a guide member to direct the instrument to the target region. The guide member may have a fixed orientation relative to the instrument template.

In some embodiments, the positioning may include positioning a coring saw outline.

In some embodiments, the positioning may include positioning a broach outline.

In some embodiments, the positioning may include positioning a prosthesis outline.

In some embodiments, the positioning may include positioning a bone implant outline.

In some embodiments, the generating may include receiving an image using fluoroscopy.

In some embodiments, the instrument template may be a first instrument template and the method may include positioning a second instrument template outside the bone interior at a position that corresponds to the target region; and generating an electronic image showing the second instrument template and the target region.

In some embodiments, the positioning of a second instrument template may include arranging the second instrument template in a plane that is oblique to a plane that includes the first instrument template.

In some embodiments, the positioning of the second instrument template comprises arranging the second instrument template in a plane that is substantially orthogonal to a plane that includes the first instrument template.

In some embodiments, the delivering may include delivering a coring saw.

In some embodiments, the delivering may include delivering a bone interior broach.

In some embodiments, the delivering may include delivering a prosthesis.

The methods may include a method for guiding an instrument into a bone interior. The method may include positioning an instrument guide adjacent a bone. The instrument guide may include a first fixation element and a second fixation element.

The method may include passing a first fixation member through the bone such that the first fixation member is in contact with the first fixation element. The method may include passing a second fixation member through the bone such that the second fixation member is in contact with the second fixation element.

In some embodiments, the passing of a second fixation member may include orienting the second fixation member substantially obliquely with respect to the first fixation member.

In some embodiments, the passing of the second fixation member may include encompassing human tissue in a region defined by the first fixation member, the second fixation member and the instrument guide such that the instrument guide is retained adjacent the bone by the human tissue.

Apparatus and methods for guiding an instrument relative to an elongated bone are provided. The apparatus may be a surgical instrument guide.

The bone may have a longitudinal axis.

The surgical instrument guide may include an instrument guide member and a base member. The base member may support the guide member. The instrument guide member may be configured to pivot with respect to the base member from a first position to a second position. The first position may define a first angle relative to the bone longitudinal axis. The second position may define a second relative to the bone longitudinal axis.

In some embodiments, the surgical instrument guide may include an alignment template. The alignment template may register the instrument guide member to a first target region inside the bone when the guide member is in the first position. The alignment template may register the instrument guide member to a second target region inside the bone when the guide member is in the second position.

In some embodiments, the template may have a dimension that corresponds to a dimension of a surgical instrument that is configured for deployment in the bone interior through the instrument guide member.

In some embodiments, the template may include a fluoroscopically detectable material.

In some embodiments, the template may be fixed to the guide member. The template may map to a lateral plane in the bone interior. The template may map to an anterior plane in the cavity. The template may map to a posterior plane in the cavity.

In some embodiments, the template may be a first template and the surgical instrument guide may include a second template. The second template may be fixed to the guide member. The second template may map to a lateral plane in the cavity.

In some embodiments, the surgical instrument guide may include a guide member stop. The guide member stop may be configured to fix the position of the guide member with respect to the base member.

In some embodiments, the stop may induce a frictional force between a first surface on the guide member and a second surface on the base member.

In some embodiments, the stop may include a projection that interferes with relative movement between the guide member and the base.

The methods may include a method for introducing an instrument into an interior of a bone. The method may include introducing the instrument into a guide member that is pivotably mounted on a base. The base may be positioned adjacent a bone. The method may include pivoting the guide member relative to the base to change an angle between the guide member and the base. The method may include advancing the instrument through the guide member.

In some embodiments, the pivoting may include adjusting the angle to align an instrument template with a target region inside the interior of the bone.

In some embodiments, the adjusting may include viewing an electronic image that shows the instrument template and the target region.

In some embodiments, the method may include fixing the angle between the guide member and the base.

Apparatus and methods for broaching an interior region of a bone are provided. The bone may include first bone material. The first bone material may include cancellous bone. The bone may include second bone material. The second bone material may include cortical bone. The second bone material may have a density that is higher than a density of the first bone material.

The apparatus may include rotator. The apparatus may include a broaching member.

The broaching member may be moved in the bone interior to displace, disaggregate, disintegrate, dislocate, excavate, abrade, cut or otherwise broach bone material. The broaching member may be rotated in the bone interior. The rotation may be continuous. The rotation may be pulsed. The rotation may be unidirectional. The rotation may alternate between a first rotational direction and a second rotational direction.

The broaching member may be fixed to the rotator. The broaching member may be configured to be moved relative to the rotator to displace bone material that is radially away from the rotator.

In some embodiments, the broaching member may be configured to substantially deflect around second bone material.

In some embodiments, the broaching member may be configured to form in the bone a space having a first contour that corresponds to a shape of the broaching member. The broaching member may be configured to form in the bone a space having a second contour that corresponds to anatomy that includes the second bone material. The broaching member may be a first broaching member and the apparatus may include a second broaching member. The second broaching member may be disposed opposite the first broaching member.

In some embodiments, the broaching member may include a cutting edge.

In some embodiments, the broaching member may include a flexible wire segment. The wire segment may include braided wire.

In some embodiments, the apparatus may include a reinforcement that supports the broaching member. The reinforcement may support a cutting edge.

In some embodiments, the broaching member may have a proximal end that is fixed to the rotator and a distal end that is fixed to the rotator.

In some embodiments, the broaching member may have a proximal end that is fixed to the rotator and a distal end that is free.

In some embodiments, the broaching member may include an edge of an open cell in a mesh.

The broaching member may include a segment that has any suitable form. For example, the segment may be straight, circular, rhombic, square, triangular, oval, ellipsoid, spiral, loop-shaped, hoop-shaped, teardrop-shaped, eggbeater-shaped, football-shaped, or any other suitable shape. The segment may be a closed loop. The loop may be asymmetric.

The segment may have one or more of a variety of transverse cross sections, such as square, rectangular, octagonal, contours with sharp edges, stranded cable, or other suitable configurations to facilitate bone displacement.

The segment may have a leading edge. The leading edge may be beveled at a suitable angle, including an angle from about 50 to about 75°. The angle may cause leading edge 2202 to be generally sharp or knife-like.

The segment may be rigid. The segment may be resilient.

The broaching member may have one or more ends that are attached to apparatus such as a drive shaft or a suitable support, such as a hub. The broaching member may have a free end. Broaching members with free distal ends may have any suitable shape at the tine distal ends, such as pointed, forked, rounded, blunt or truncated.

The broaching member may have an end that is attached to apparatus by crimping, welding, set-screw, snap fit or any other suitable fastening. The broaching member may have one or more ends that are of unitary construction with the apparatus.

The broaching member may include a tine. The tine may be resilient or stiff. The tine may have an end that is attached to a drive shaft. The tine may have a free end.

The broaching member may include a blade.

The broaching member may include numerous interconnected cells. The cells may be arranged in a network. The cells may be linked such that when the structure is stressed (e.g., compressed) at a point the stress is distributed to nearby cells. The cells may be constructed from laser-cut tube stock that is expanded into a suitable shape.

The broaching member may be one of a number of broaching members in a broaching head. For example, the broaching head may have one broaching member, 2-6 broaching members, 7-20 broaching members, more than 20 broaching members, 100 broaching members or any suitable number of broaching members.

When a large number (i.e., when the circumferential density of broaching members is relatively high) of broaching members are present during the rotation of a broaching head, a relatively lower torque may be required to drive the broaching head.

Broaching member may rotate in a bone cavity that has an irregular shape, for example, nonround, oblong, or angular. The cavity may be smaller than a diameter of broaching member.

Broaching member may include any suitable structural form such as wire, ribbon, cable, stranded wire, braided wire, braided ribbon, or any other suitable structural form.

Broaching member may include any suitable material, such as polymer, metal, composite, stainless steel, Nitinol (shapeset, superelastic or other Nitinol), other alloy or any other suitable material.

The broaching member may be supported by one or more reinforcements.

The reinforcement may be sized and positioned to support a segment of the broaching member in a desired contour. The reinforcement may provide bone-broaching abrasiveness, momentum or both.

The reinforcement may be a tube.

The reinforcement may be a brace. The brace may be fixed to the broaching member, for example, by crimping, welding or press-fit. The brace may include broaching edges for displacing bone material. The broaching edges may have any suitable form, such as serrated, saw-tooth, knife-edge, rectilinear edge or any other suitable form.

The reinforcement may be formed from polymer, metal, alloy or any other suitable material.

The reinforcement may be formed from a pattern that is cut into a metal tube.

In some embodiments, the apparatus may include a distal hub. The broaching member may have a distal end that is fixed to the distal hub. The distal hub may be configured to move between a first position and a second position. The first and second positions may be located along a longitudinal axis of the rotator.

The distal hub may be constructed of metal, stainless steel, laser-cut tube, polymer, ceramic or any other suitable material.

The distal hub may include flutes. The distal hub may include broaching edges.

The methods may include a method for broaching an interior region of a bone. The interior region may include a bottom surface. The bottom surface may be an surface of a portion of the bone that is opposite an access hole in the bone.

The method may include expanding a bone broaching member in the interior region. The method may include disaggregating relatively low-density material inside the bone using the member. The method may include deflecting the broaching member away from relatively high-density material inside the bone.

In some embodiments, the method may include rotating the bone broaching member using a flexible drive shaft.

In some embodiments, the method may include changing the elevation of the bone broaching member relative to the bottom surface.

In some embodiments, the disaggregating may include cutting the relatively low-density material.

In some embodiments, the disaggregating may include displacing the relatively low-density material.

In some embodiments, the method may include registering an exterior instrument guide to the bone broaching member; visually mapping the exterior instrument guide to the interior region; and deploying the bone broaching member to the interior region based on the exterior instrument guide. The exterior instrument guide may be exterior to the bone.

Apparatus and methods for treating a bone interior are provided.

The apparatus may include a flexible sheath. The flexible sheath may include stress-relief features that allow bending under tension and compression. The stress-relief features may include slots or slot patterns. The stress-relief features may be provided using laser-cutting.

The stress-relief features may include sintered particles. The particles may include metal, polymer, composite or any other suitable material.

The flexible sheath may have a first configuration and a second configuration. The second configuration may have a smaller radius of curvature than the first configuration. The apparatus may include a rotatable shaft. The rotatable shaft may extend through the sheath. The apparatus may include an elongated steering member. The elongated steering member may be configured to deflect the flexible sheath from the first configuration to the second configuration.

In some embodiments, the elongated steering member may be configured to be elastically deformed when the elongated steering member deflects the flexible sheath from the first configuration to the second configuration.

In some embodiments, the elongated steering member may include a first portion. The first portion may translate along a longitudinal direction of the sheath. The elongated steering member may include a second portion. The second portion may be configured to extend radially outward through a passage in the sheath when the elongated steering member deflects the flexible sheath from the first configuration to the second configuration.

In some embodiments, the rotatable shaft may have a distal end and the apparatus may include an expandable head that extends from the distal end. The expandable head may include a compressed configuration for translating within the sheath. The expandable head may include an expanded configuration when the expandable head is deployed outside the sheath.

In some embodiments, the expandable head may be configured to displace cancellous bone and not cortical bone.

Apparatus and methods for preparation of the interior of a bone are provided.

The apparatus may include an elongated member. The elongated member may have a longitudinal axis. The elongated member may be curved about the longitudinal axis. The elongated member may be configured to rotate about the longitudinal axis inside the bone.

In some embodiments, the elongated member may include a substantially spiral segment. The spiral segment may include a proximal end and a distal end. The proximal end may be disposed at a first radius from the longitudinal axis. The distal end may be disposed at a second radius from the longitudinal axis. The second radius may be at least as great as the first radius. The second radius may be greater than the first radius.

In some embodiments, the elongated member may be a first elongated member and the apparatus may include a second elongated member. The second elongated member may be curved about the longitudinal axis. The second elongated member may be configured to rotate about the longitudinal axis.

In some embodiments, the second elongated member may include a substantially spiral second segment.

In some embodiments, the proximal end may be a first proximal end and the distal end may be a first distal end. The spiral second segment may include a second proximal end and a second distal end. The second proximal end may be disposed at a third radius from the longitudinal axis. The second distal end may be disposed at a fourth radius from the longitudinal axis. The fourth radius may be at least as great as the third radius. The fourth radius may be greater than the third radius.

In some embodiments, the third radius may be substantially the same as the first radius; and the fourth radius may be substantially the same as the second radius.

In some embodiments, the apparatus may include a circumferential offset. The circumferential offset may be in a circumferential direction about the longitudinal axis. The circumferential offset may be between the second proximal end and the first proximal end. The circumferential offset may be between the second distal end and the first distal end.

In some embodiments, the apparatus may include a support. The support may include a proximal support end. The proximal support end may be fixed to a shaft. The apparatus may include a support segment. The support segment may be fixed to at least one of the first and second spiral segments. The support segment may conform to a contour of the spiral segment.

The methods may include a method for preparing a bone interior. The method may include providing access to a bone intramedullary space. The method may include introducing into the intramedullary space an elongated member. The elongated member may have a substantially spiral segment. The spiral segment may have a longitudinal axis. The method may include rotating the substantially spiral segment about the longitudinal axis to displace cancellous bone matter.

In some embodiments, the elongated member may be a first elongated member, the substantially spiral segment may be a first substantially spiral segment, and the method may include introducing into the intramedullary space a second elongated member. The second elongated member may have a substantially spiral second segment. The substantially spiral second segment may share the longitudinal axis with the first substantially spiral segment. The method may include rotating the substantially spiral second segment about the longitudinal axis.

In some embodiments, the first spiral segment may have a first periodic rotation cycle. The second spiral segment may have a second periodic rotation cycle. The second periodic rotation cycle may lag behind the first periodic rotation cycle by a phase lag. The phase lag may be about Pi radians.

Apparatus and methods for sawing a hole in a bone are provided. The bone may have a longitudinal bone axis.

The apparatus may include a bone coring saw. The bone coring saw may include a tooth. The tooth may include a first cutting member and a second cutting member. The first cutting member may be configured to cut bone when the coring saw rotates in a first direction. The second cutting member may be configured to cut bone when the coring saw rotates in a second direction. The second direction may be rotationally opposite from the first direction.

The bone coring saw may include a cylindrical tube. The cylindrical tube may define a tube longitudinal direction and a tube radial direction. The bone coring saw may include a saw tooth. The saw tooth may extend longitudinally from an end of the cylindrical tube. The saw tooth may include a cutting surface that is oblique to the tube radial direction.

The methods may include a method for sawing a hole in the bone. The method may include forming a substantially cylindrical passage into the intramedullary space of a bone. The substantially cylindrical passage may extend along a direction that is at an acute angle to the longitudinal bone axis. The method may include removing from the bone a substantially cylindrical plug that is substantially coaxial with the passage.

In some embodiments, the forming may include tunneling through the bone using a K-wire.

In some embodiments, the removing may include sawing a hole using a rotary coring saw.

In some embodiments, the method may include rotating the rotary coring saw about a portion of the K-wire.

In some embodiments, the method may include sustaining a coaxial relationship between the K-wire and the rotary coring saw. The sustaining may include rotating the rotary coring saw about a bushing. The K-wire, the bushing and the rotary coring saw may be substantially coaxial.

In some embodiments, the method may include translating the K-wire relative to the rotary coring saw to remove from the coring saw the cylindrical plug.

The method may include a method for providing access to an intramedullary space of a bone. The method may include supporting a cylindrical body of a rotary saw at an acute angle to a surface of the bone; and engaging teeth of the rotary saw with the surface.

Apparatus and methods for accessing the inside of a bone are provided.

The apparatus may include a rotatable saw that includes a cannula. The apparatus may include a bushing that is disposed in the cannula. The apparatus may include a wire that is disposed substantially coaxially with the rotatable saw in the bushing.

In some embodiments, the wire may include a distal end that is configured to penetrate the bone. The wire may include a proximal end that is configured to receive torque.

In some embodiments, the wire may be configured to drill a pilot hole in the bone. The pilot hole may have an axis that forms an acute angle with a surface of the bone at the opening of the pilot hole. The saw may include teeth. The teeth may be arranged adjacent a distal end of the cannula. The bushing may be configured to align the rotatable saw coaxially with the axis when the teeth contact the bone.

In some embodiments, the apparatus may include a biased member proximal the bushing. The biased member may be configured to urge a distal end of the bushing toward the bone when the teeth have penetrated into the bone.

In some embodiments, the bushing may be fitted into the cannula with a tolerance that provides friction between the bushing and the rotatable saw. The friction may resist proximally-directed force from a bone core in the cannula while the teeth are cutting into the bone.

In some embodiments, the rotatable saw may include a cylindrical body having a wall thickness that is traversed by a vent. The vent may be configured to exhaust bone matter.

In some embodiments, the wire may include a distal diameter and a proximal diameter. The proximal diameter may be greater than the distal diameter. The wire may include a shoulder where the distal diameter adjoins the proximal diameter. The shoulder may be configured to be translated proximally relative to the rotatable saw to eject a bone core from the cannula.

The apparatus may include an assembly for accessing the inside of a bone.

The assembly may include an arrangement of teeth. The teeth may be supported at the end of a rotatable frame. The frame may define one or more passageways. The passageways may extend from a cannula inside the frame to a region that is outside the frame.

In some embodiments, the assembly may include a bushing. The bushing may be disposed in the cannula. The assembly may include a wire. The wire may be disposed substantially coaxially with the rotatable saw in the bushing.

In some embodiments, the wire may be configured to drill a pilot hole in the bone. The pilot hole may have an axis that forms an acute angle with a surface of the bone at the opening of the pilot hole. The busing may be configured to align the rotatable saw coaxially with the axis when the teeth contact the bone.

Apparatus and methods for preparing a bone interior are provided. The apparatus may have a longitudinal apparatus axis.

The apparatus may include one or more broaching members. The broaching members may be blades. A first blade may be linked to a second blade by a linkage. The linkage may be configured to be rotated about the longitudinal axis. The linkage maybe configured to be radially displaced from the longitudinal apparatus axis.

In some embodiments, at least one of the first and second blades may be rigid.

In some embodiments, at least one of the first and second blades may include stainless steel.

In some embodiments, at least one of the first and second blades may include Nitinol.

In some embodiments, the linkage may include a pin.

In some embodiments, the linkage may be a first linkage. The apparatus may include an actuator. The actuator may be linked to the first blade by a second linkage. The actuator may be linked to the second blade by a third linkage. The actuator may include a main body. The main body may include members that are configured to be displaced relative to each other. One of the members may be fixed relative to the main body.

In some embodiments, at least one of the second and third linkages may include a pin.

In some embodiments, the third linkage is distal the second linkage.

In some embodiments, the actuator may be configured to radially displace the first linkage by changing a distance between the second linkage and the third linkage.

In some embodiments, the actuator may include a first elongated actuator member. The first elongated actuator member may be linked to the second linkage. The actuator may include a second elongated actuator member. The second elongated actuator member may be linked to the third linkage. The second elongated actuator member may be configured to radially displace the first linkage by changing a longitudinal offset between the first and second elongated members.

In some embodiments, the apparatus may be configured to traverse a path in the bone interior. The apparatus may include a fourth linkage that constrains the longitudinal offset based on position of the apparatus along the path.

In some embodiments, the fourth linkage may be a manual linkage.

In some embodiments, the longitudinal offset may include a range of values. The range of values may include a first value. The first value may correspond to a first linkage first radial displacement. The range of values may include a second value. The second value may correspond to a first linkage second radial displacement. The second radial displacement may be greater than the first radial displacement.

In some embodiments, the range may include a third value. The third value may correspond to a first linkage third radial displacement. The first linkage third radial displacement may be less than the second radial displacement.

In some embodiments, the apparatus may include a cutting surface. The cutting surface may be disposed on one of the first and second blades. At the first and third radial displacements, the cutting surface may be disengaged from the bone.

In some embodiments, at the second radial displacement, the cutting surface may be engaged with the bone.

In some embodiments, the first blade may have a first bound portion. The first bound portion may be between the first and second linkages. The first blade may have a first free portion. The first free portion may extend beyond the first linkage in a direction away from the second linkage.

In some embodiments, the second blade may have a second bound portion. The second bound portion may be between the first and third linkages. The second blade may have a second free portion. The second free portion may extend beyond the first linkage in a direction away from the third linkage.

In some embodiments, the first bound portion may be longer than the second bound portion.

In some embodiments, the second bound portion may be longer than the first bound portion.

In some embodiments, the first free portion may be longer than the second free portion.

In some embodiments, the second free portion may be longer than the first free portion.

In some embodiments, the apparatus may include a cutting surface. The cutting surface may be disposed on at least one of the first and second blades. The fourth linkage may be programmed to position the cutting surfaces at different radial displacements along the path. Each of the radial displacements may correspond to a longitudinal position on the path.

In some embodiments, the fourth linkage may control the longitudinal offset based on an electronic signal. The electronic signal may be based on a set of digital instructions. The digital instructions may be based on a digitized image of the bone interior.

In some embodiments, the apparatus may include a third blade. The apparatus may include a fourth blade. The third blade may be linked to the fourth blade by a fourth linkage. The fourth linkage may be configured to be rotated about the longitudinal axis. The fourth linkage may be configured to be radially displaced from the longitudinal axis. The actuator may be configured to radially displace the fourth linkage by changing the longitudinal offset between the first and second elongate members.

The methods may include a method for preparing the bone interior. The method may include rotating a cutting surface inside a bone about a rotational axis. The method may include moving a control member from a first control position to a second control position.

The cutting surface may be configured to occupy a first radial position that corresponds to the first control position. The cutting surface may be configured to occupy a second radial position that corresponds to the second control position. The cutting surface may be configured to occupy a third radial position that corresponds to an intermediate control position. The intermediate control position may be between the first and second control positions. The third radial position may be at a greater radial distance from the rotational axis than are both the first and second radial positions.

In some embodiments, the first and second radial positions may be at substantially the same distance from the rotational axis.

In some embodiments, when the cutting surface is at one or both of the first and second radial positions, the cutting surface may be disengaged from the bone. When the cutting surface is at the third radial position, the cutting surface may be engaged with the bone.

Apparatus and methods for positioning a bone fragment are provided.

The apparatus may include a probe support. The probe support may have a proximal end and a distal end. The apparatus may include a handle. The handle may be attached to the proximal end. The apparatus may include a probe. The probe may be attached to the distal end. The probe support may be configured to traverse an angled access hole in a metaphyseal bone surface. The probe support may be configured to provide mechanical communication between the handle and the probe when the handle is outside a bone interior and the probe is inside the bone interior.

In some embodiments, the probe may have a conical tip.

In some embodiments, the probe may have a rounded tip.

In some embodiments, the probe support may include a proximal segment and a distal segment. The proximal segment may extend from the handle. The distal segment may support the probe.

In some embodiments, the proximal and distal segments may define an obtuse angle.

In some embodiments, the proximal segment may have a first flexibility. The distal segment may have a second flexibility. The second flexibility may be greater than the first flexibility.

In some embodiments, the apparatus may include an intermediate segment. The intermediate segment may be between the proximal and distal segments. The intermediate segment may include a curve.

In some embodiments, the proximal segment may have a first flexibility. The intermediate segment may have a second flexibility. The distal segment may have a third flexibility. The second flexibility may be greater than the third flexibility.

The methods may include a method for treating a bone. The bone may have a longitudinal bone axis.

The method may include providing a hole in the bone. The hole may be at an angle to the longitudinal bone axis. The hole may provide access to a bone interior region. The method may include advancing a probe through the hole and into the interior region. The method may include displacing cancellous bone using the probe.

In some embodiments, the displacing may include identifying a spatial distribution of low-density matter in the interior region.

In some embodiments, the method may include displaying an image of the interior region and the probe when the probe is inside the interior region.

The methods may include another method for treating the bone. The method may include providing a hole in the bone. The hole may be at an angle to the longitudinal bone axis. The hole may provide access to a bone interior region. The method may include advancing a probe through the hole and into the interior region. The method may include displacing bone matter using the probe.

In some embodiments, the displacing may include identifying a spatial distribution of cancellous bone in the interior region.

In some embodiments, the method may include displaying an image of the interior region and the probe when the probe is inside the interior region.

In some embodiments, the displacing may include positioning a first cortical bone fragment relative to a second cortical bone fragment.

In some embodiments, the method may include displaying an image of the interior region and the probe when the probe is inside the interior region.

Apparatus and methods in accordance with the invention will be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown or described herein. Some embodiments may omit steps shown or described in connection with the illustrative methods. Some embodiments may include steps that are not shown or described in connection with the illustrative methods.

Illustrative embodiments will now be described with reference to the accompanying drawings, which form a part hereof.

The apparatus and methods of the invention will be described in connection with embodiments and features of an illustrative bone repair device and associated hardware and instrumentation. The device and associated hardware and instruments will be described now with reference to the FIGS. It is to be understood that other embodiments may be utilized and structural, functional and procedural modifications may be made without departing from the scope and spirit of the present invention.

FIG. 1 shows illustrative instrument guide 100 positioned at site H' on bone B. Broach head 124 may be delivered through guide 100 to target region $R_t$ of intramedullary space IS. Target region $R_t$ is illustrated as being within cancellous bone $B_{CA}$, but could be in either, or both, of cancellous bone $B_{CA}$ and cortical bone $B_{CO}$. Side template 130 and top template 132 are registered to guide tube 120. Arm 131 may support template 130. A practitioner may position templates 130 and 132 such that templates 130 and 132 "project" onto target region $R_t$ so that guide 100 will guide broach head 124 to target region $R_t$.

Template 130 may include lobe outline 134 and shaft outline 136 for projecting, respectively, a "swept-out" area of broach head 124 and a location of shaft-like structure 125. Template 132 may include lobe outline 138 and shaft outline 140 for projecting, respectively, a target "swept-out" area of broach head 124 and a target location of shaft-like structure 125. Templates 130 and 132 may be configured to project a shape of any suitable instrument that may be deployed, such as a drill, a coring saw, a prosthetic device or any other suitable instrument.

Fluoroscopic imaging may be used to position templates 130 and 132 relative to target region $R_t$.

Broach head 124 may rotate in intramedullary space IS to clear intramedullary bone matter so that a prosthetic device may be implanted. Broach head 124 may be driven and supported by broach control 126 and broach sheath 127.

Guide 100 may include base 102. Alignment members 104 and 106 (shown in FIG. 10) may extend from base 102 to align guide centerline $CL_G$ of guide 100 with bone centerline $CL_{BS}$ of the top surface of bone B. One or both of alignment members 104 and 106 may be resilient. One or both of alignment members 104 and 106 may be stiff.

Alignment members 104 and 106 may be relatively free to slide along surfaces of bone B. Guide 100 may include contacts 108 and 110 (shown in FIG. 10) that may engage bone B along centerline $CL_{BS}$. Contacts 108 and 110 may extend from a bottom surface (shown in FIG. 10) of guide 100. Contacts 108 and 110 may prevent guide centerline $CL_G$ from rotating out of alignment with bone centerline $CL_{BS}$.

Contacts 108 and 110 may assure alignment of guide 100 with the surface of bone B, because two points of contact may be stable on an uneven surface even in circumstances in which 3, 4 or more contacts are not stable.

Figure 10:
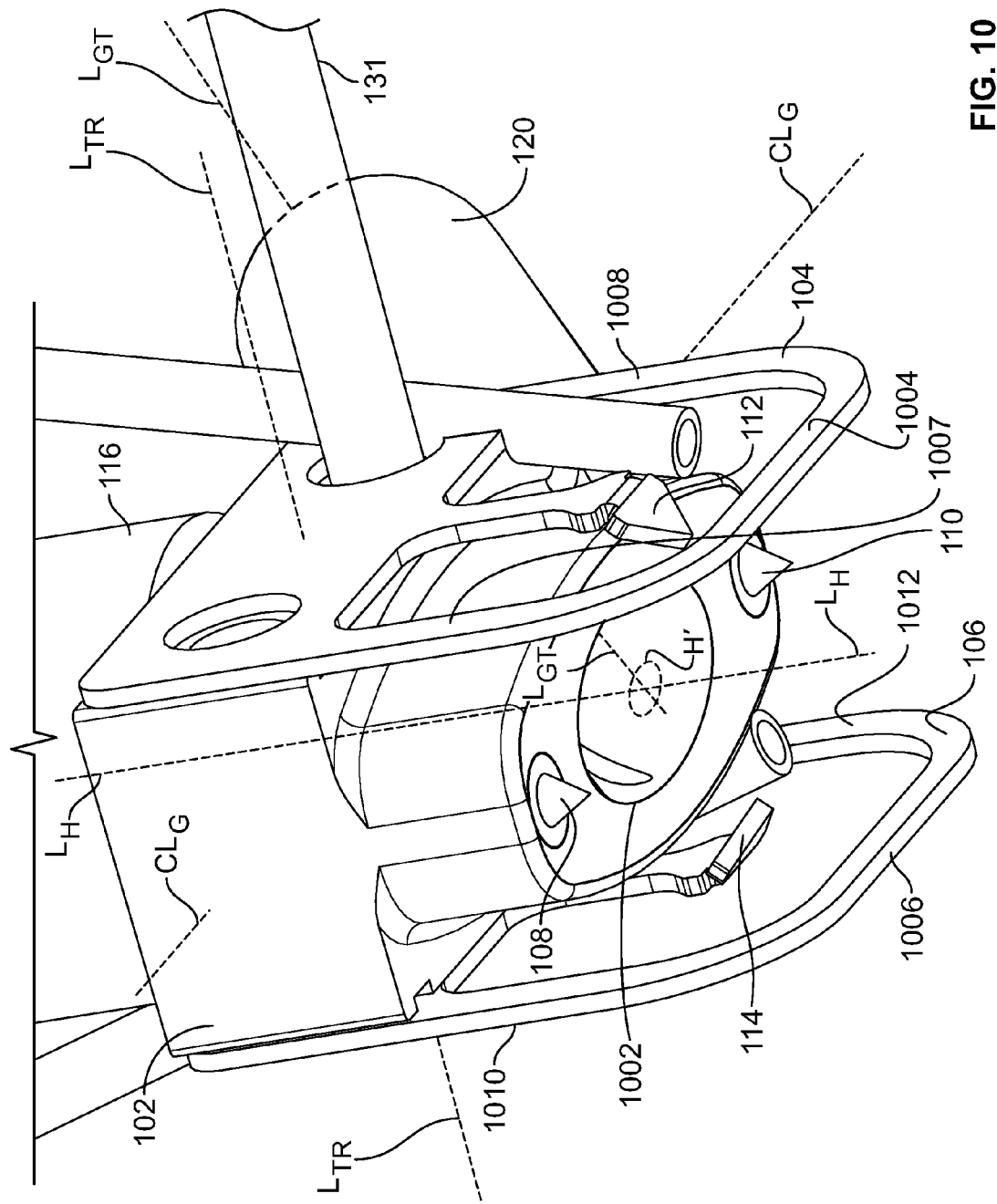
FIG. 10 shows a portion of the apparatus shown in FIG. 1.

Guide 100 may include lateral cleats 112 and 114 (shown in FIG. 10). Lateral cleats 112 and 114 may engage the surface of bone B to prevent guide 100 from rotating in direction θ about guide centerline $CL_G$. Lateral cleats 112 and 114 may be resilient to allow some sliding over bone B.

When a practitioner positions guide 100 on bone B, alignment members 104 and 106 may be the first components of guide 100 to engage bone B. Alignment members 104 and 106 may bring guide centerline $CL_G$ into alignment with bone centerline $CL_{BS}$ before contacts 108 and 110 and cleats 112 and 114 engage bone B. Then, in some embodiments, cleats 112 and 114 may engage bone B to inhibit rotation in direction θ. Then, in some embodiments, contacts 108 and 110 may engage bone B along bone centerline $CL_{BS}$. Contacts 108 and 110 may have sharp points to provide further resistance to de-alignment of guide centerline $CL_G$ from bone centerline $CL_{BS}$. In some embodiments, there may be no more than two contacts (e.g., 108 and 110) to ensure that the contacts are in line with bone centerline $CL_{BS}$.

Guide 100 may include stem 116 and grip 118. A practitioner may manually grip grip 118. In some embodiments, a torque-limiter (not shown) may be provided to limit the torque that the practitioner can apply via grip 118 to contacts 108 and 110.

Guide tube 120 may receive and guide any suitable instrument. Guide tube 120 may be oriented at angle α with respect to handle 116. In some embodiments, angle α may be fixed. In some embodiments, angle α may be adjustable. In some embodiments, templates 130 and 132 may be fixed relative to guide tube 120. In some embodiments, including some embodiments in which a is adjustable and some in which a is not adjustable, guide tube 120 may be oriented so that the axis $L_{GT}$ of guide tube 120 intersects bone B at substantially the same point as does axis $L_H$ of stem 116. Grip 118 will thus be positioned directly over the center of hole site H'.

Figure 5:
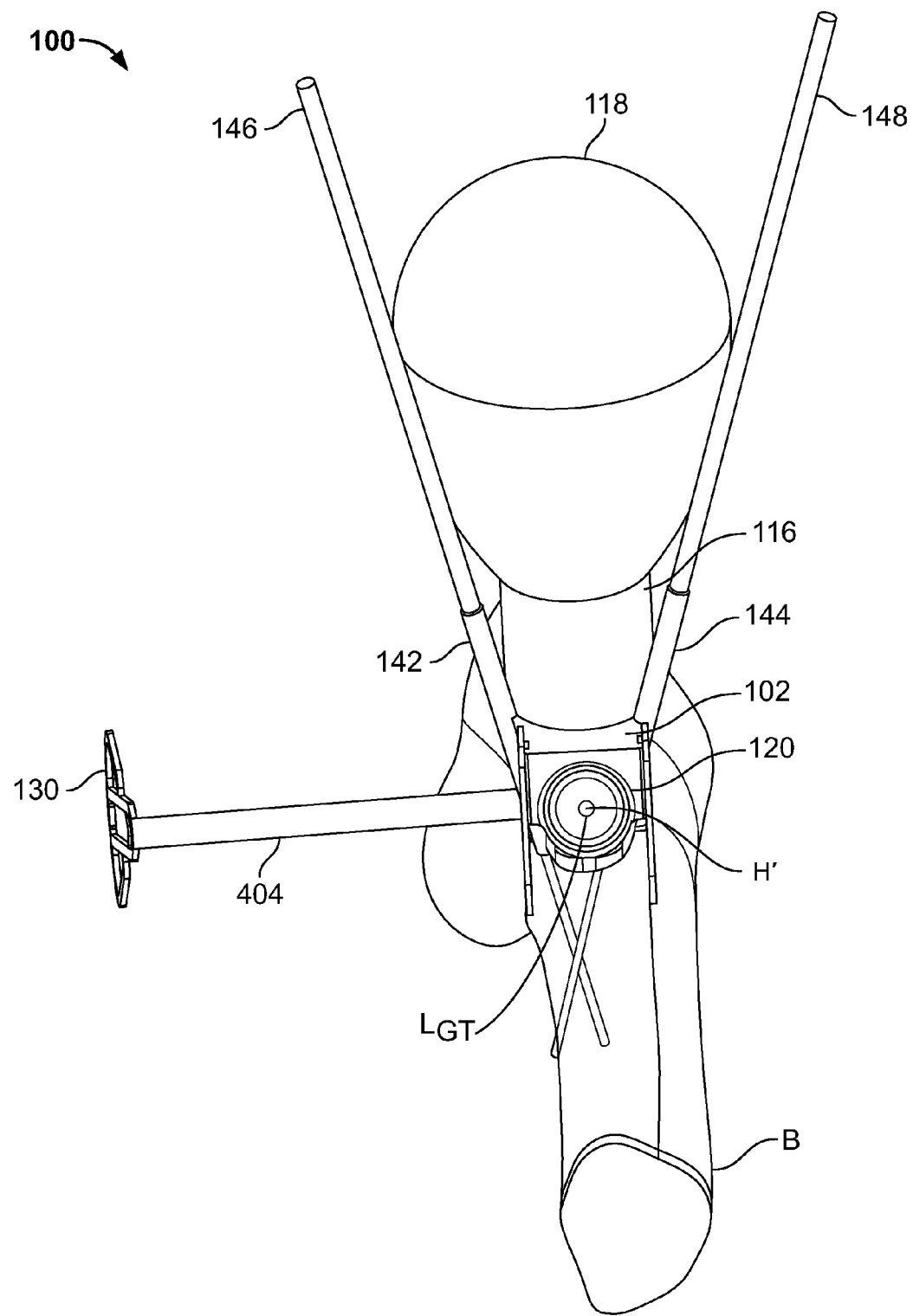
FIG. 5 shows a view, taken along lines 5-5 (shown in FIG. 1) of a portion of the apparatus shown in FIG. 1.

Guide 100 may include channels 142 and 144 (shown in FIG. 5). Rods 146 and 148 may be inserted through channels 142 and 144, respectively, through cortical bone $B_{CO}$. Rods 146 and 148 may stabilize guide 100 on bone B. Rods 146 and 148 may be K-wires. Rods 146 and 148 may be inserted using a wire drill.

Figure 2:
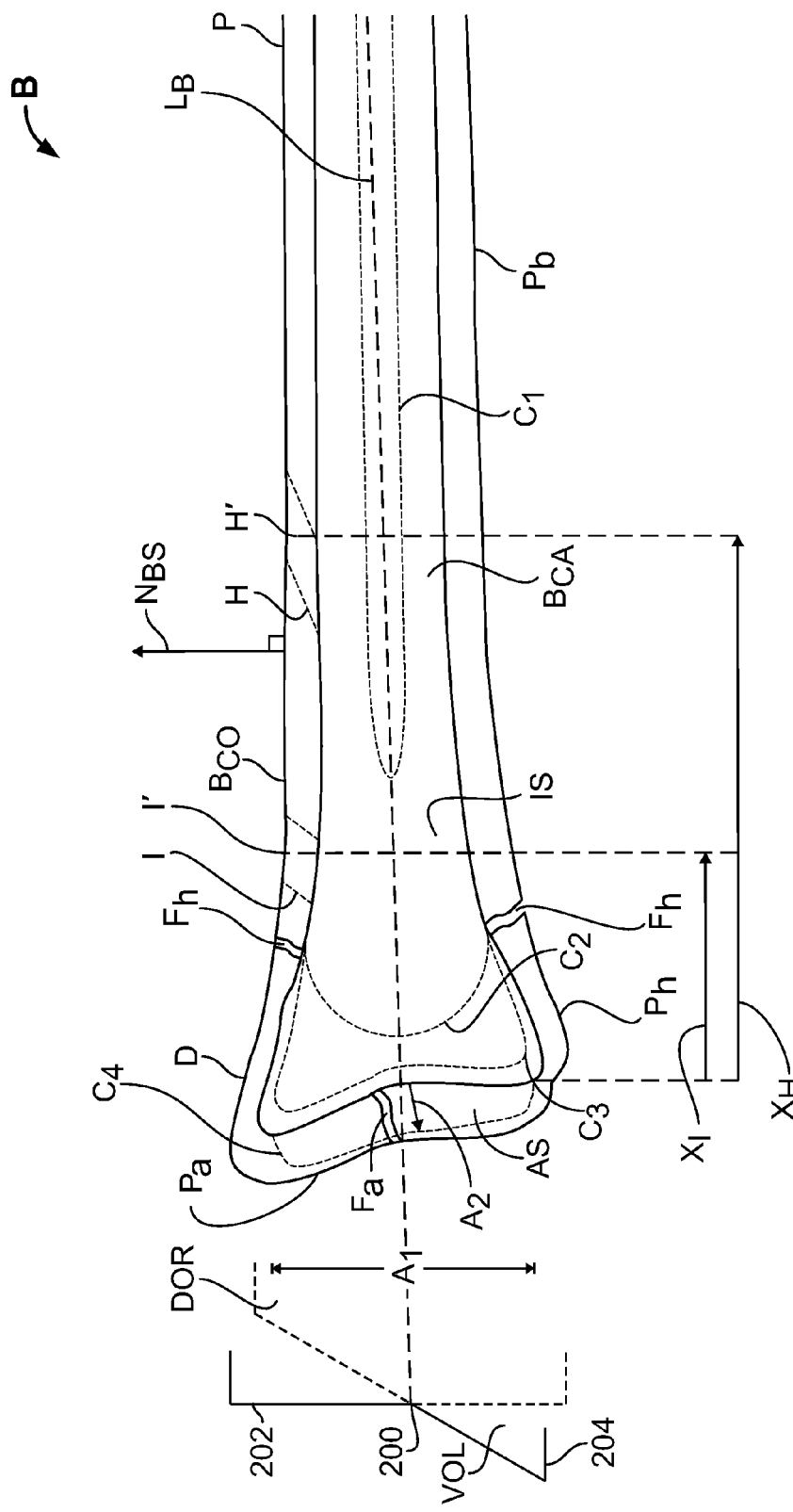
FIG. 2 shows illustrative anatomy in connection with which the invention may be practiced.

FIG. 2 illustrates anatomical features of fractured bone B. Reference frame 200 shows that the view of bone B is substantially in anterior/posterior plane 200. Lateral plane 204 includes volar half-plane VOL and dorsal half-plane DOR.

Bone B is illustrated as a radius that is fractured at fractures $F_h$ and $F_a$. Bone B includes bone portions $P_b$, $P_h$ and $P_a$ in distal end D. Bone segment $P_b$ is the largest portion of bone B. Bone segment $P_h$ is a head portion of bone B. Bone segments $P_h$ and $P_a$ include articular surface AS.

Bone portions $P_b$, $P_h$ and $P_a$ are separated or partially separated along fractures $F_a$ and $F_h$. Fracture $F_a$ transects articular surface AS. Fracture $F_h$ transects head of bone B.

Bone B, shown in a cross section that includes approximate longitudinal axis $L_B$, includes cortical bone $B_{CO}$ and cancellous bone $B_{CA}$. Deployment of an implant into distal end D of bone B may require an access hole at site H'. Deployment of the implant may require displacement of cancellous bone $B_{CA}$. Illustrative contours $C_1$, $C_2$ and $C_3$ in cancellous bone $B_{CA}$ are different contours within which cancellous bone $B_{CA}$ may be displaced. Contour $C_4$, which is a projection of contour $C_3$ onto articular surface AS, shows that contour $C_4$, for example, may be asymmetric. For example, contour $C_4$ may have major axis $A_1$ and minor axis $A_2$ (shown in half). The other contours may also be asymmetric.

Apparatus and methods provided herein may provide an access hole H at site H'. An apparatus inserted at site H' through access hole H, may travel a distance $x_H$ through intermedullary space IS to reach a head portion of bone B. An apparatus inserted at site I' through access hole I may travel a distance $x_I$ through intermedullary space IS to reach a head portion of bone B. An apparatus inserted at H' may require a "bend" to travel through intermedullary space IS to reach a head portion of bone B. An apparatus inserted at I' may not require a "bend" to reach a head portion of bone B. Apparatus and methods provided herein may displace cancellous bone $B_{CA}$ within a contour such as $C_1$, $C_2$ or $C_3$.

Figure 3:
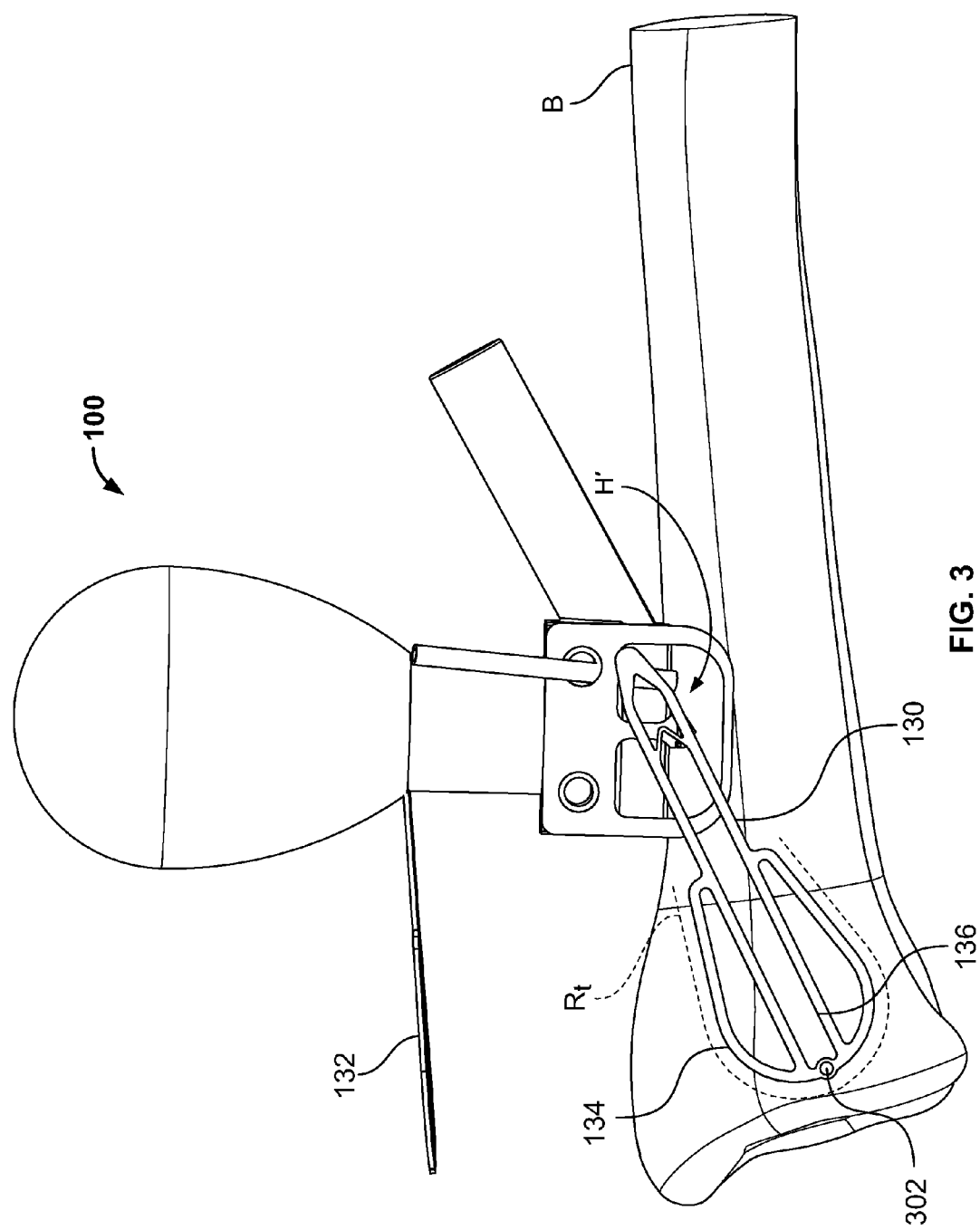
FIG. 3 shows a view, taken along lines 3-3 (shown in FIG. 1) of a portion of the apparatus shown in FIG. 1.

FIG. 3 shows guide 100, from the side, positioned at site H' at which an access hole is to be provided. Template 130 is positioned to register with target area $R_t$ a broach (with outline 134) and a drill (with outline 136). Template 132 extends normal to the plane of FIG. 3. Fluoroscopy may be used to select the target area based on contours of cancellous bone $B_{CA}$ and cortical bone $B_{CO}$ (shown in FIG. 2) in bone B. A rod such as a K-wire may be inserted through hole 302 and bone B to fix a position of guide 100 relative to bone B.

Figure 4:
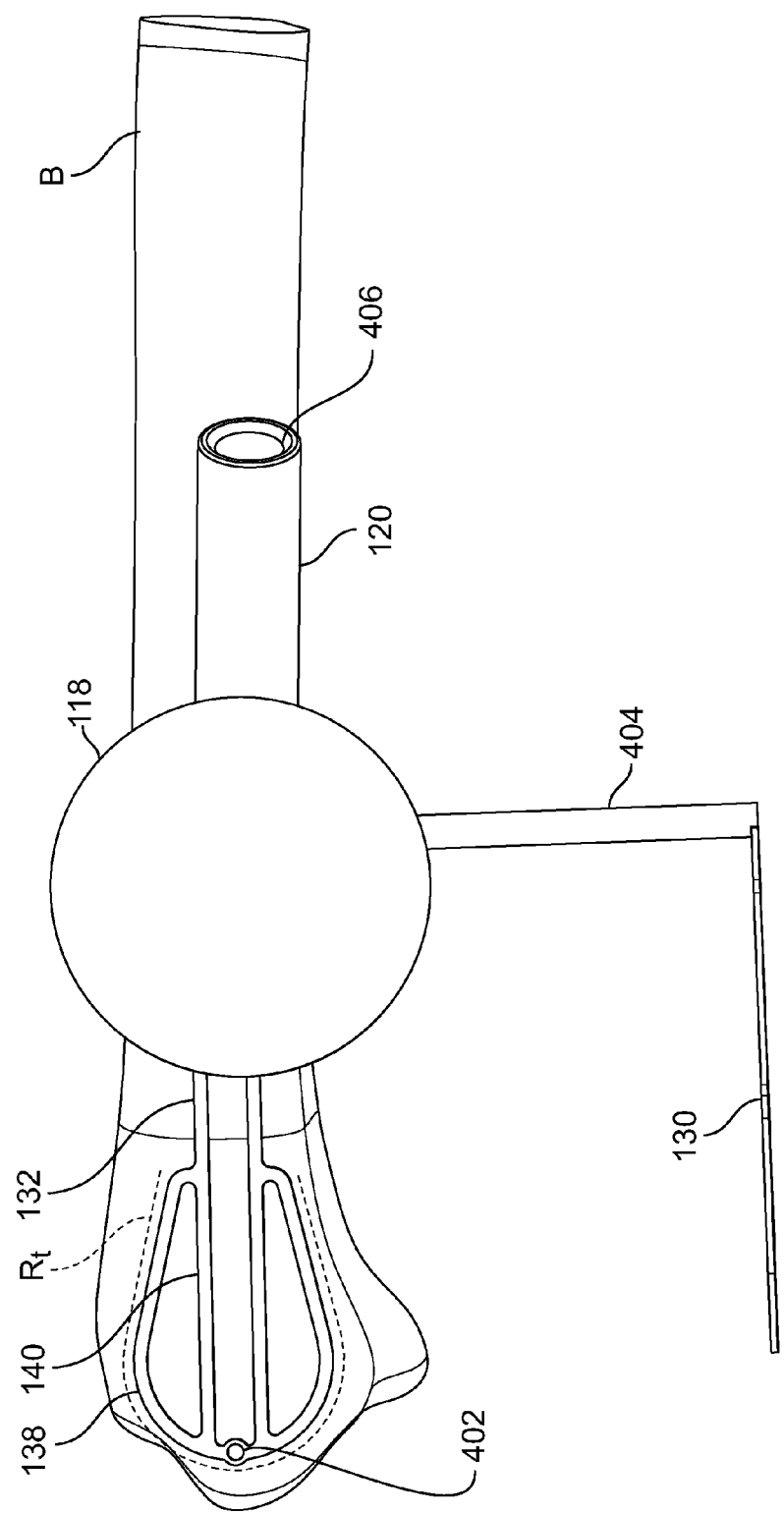
FIG. 4 shows a view, taken along lines 4-4 (shown in FIG. 1) of a portion of the apparatus shown in FIG. 1.

FIG. 4 shows guide 100, from the top, positioned at site H' (not shown). Template 132 is positioned to register with target area $R_t$ the broach (with outline 138) and the drill (with outline 140).

Template 132 extends from the base of grip 118.

Arm 404 supports template 130, which extends normal to the plane of FIG. 3. Fluoroscopy may be used to select the target area based on contours of cancellous bone $B_{CA}$ (shown in FIG. 2) and cortical bone $B_{CO}$ (shown in FIG. 2) in bone B. A rod such as a K-wire may be inserted through hole 402 and bone B to fix a position of guide 100 relative to bone B.

Cannula 406 is present in guide tube 120 for delivering instruments to intramedullary space IS (shown in FIG. 2) of bone B.

FIG. 5 shows guide 100, from above and posterior, positioned at site H'. H' is approximately centered along axis $L_{GT}$ of guide tube 120. Distal ends of rods 146 and 148 penetrate bone B to maintain a position of guide 100. Rods 146 and 148 may be at oblique to each other. Rods 146 and 148 may be skewed relative to each other.

Figure 6:
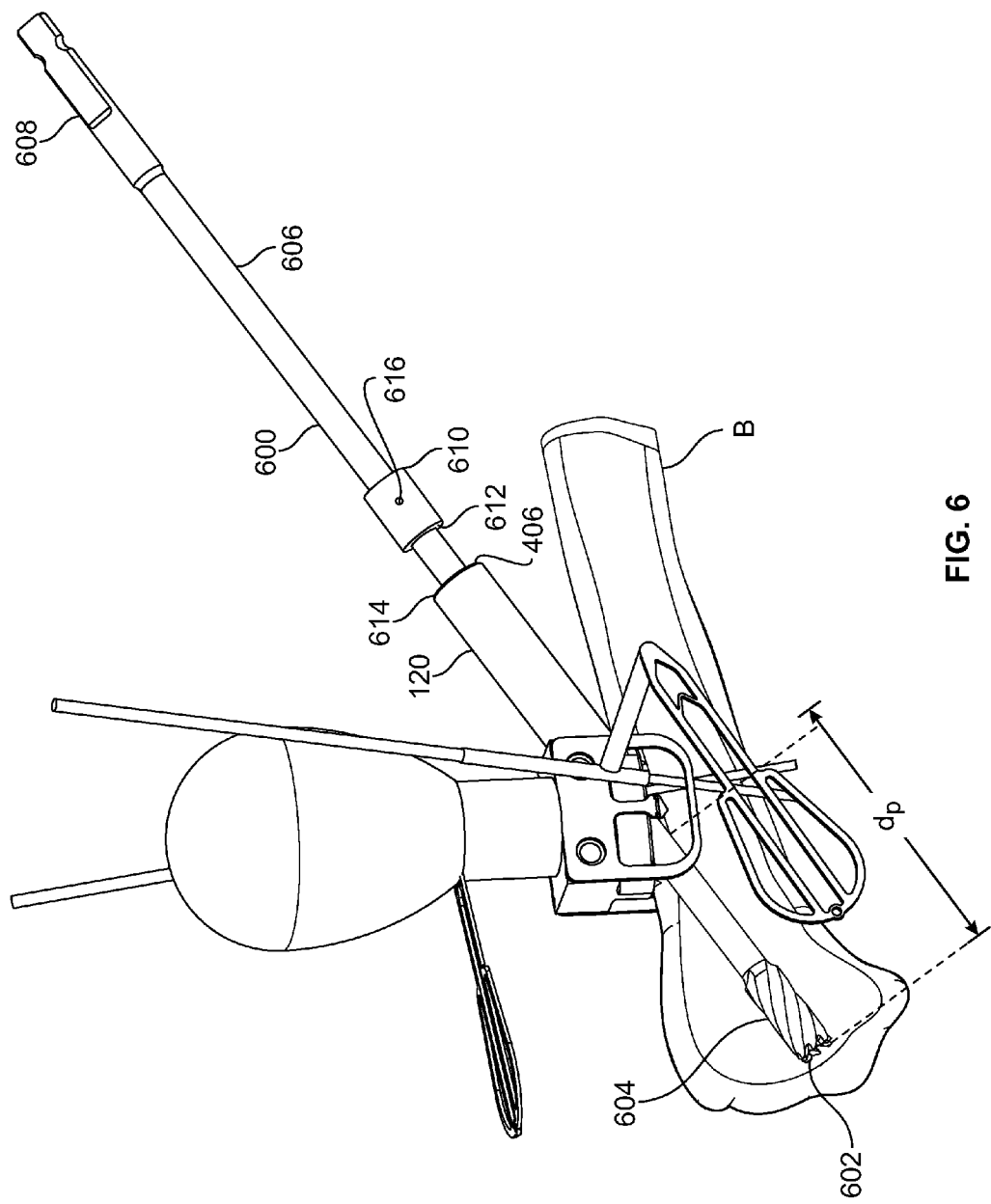
FIG. 6 shows a portion of the apparatus shown in FIG. 1 along with other apparatus in accordance with principles of the invention.

FIG. 6 shows illustrative drill 600 inserted in guide tube 120 and penetrating bone B. Drill 600 may penetrate cortical bone $B_{CO}$ (shown in FIG. 2) and cancellous bone $B_{CA}$ (shown in FIG. 2). Drill 600 may include teeth 602, flutes 604, shaft 606, torque adapter 608 and any other suitable features. Torque adapter 608 may be an A-O type torque adapter or any other suitable torque adapter. Stop 610 may be present to limit penetration depth $d_P$ of drill 600. Stop 610 may be any suitable feature that limits forward axial motion of members 600. Stop 610 may include annular distal surface 612, which may abut rim 614 of guide tube 120 when $d_P$ is reached. Fastener 616, which may be a set screw, may be used to fix the position of stop 610 along shaft 606 to fix the magnitude of $d_P$.

Figure 7:
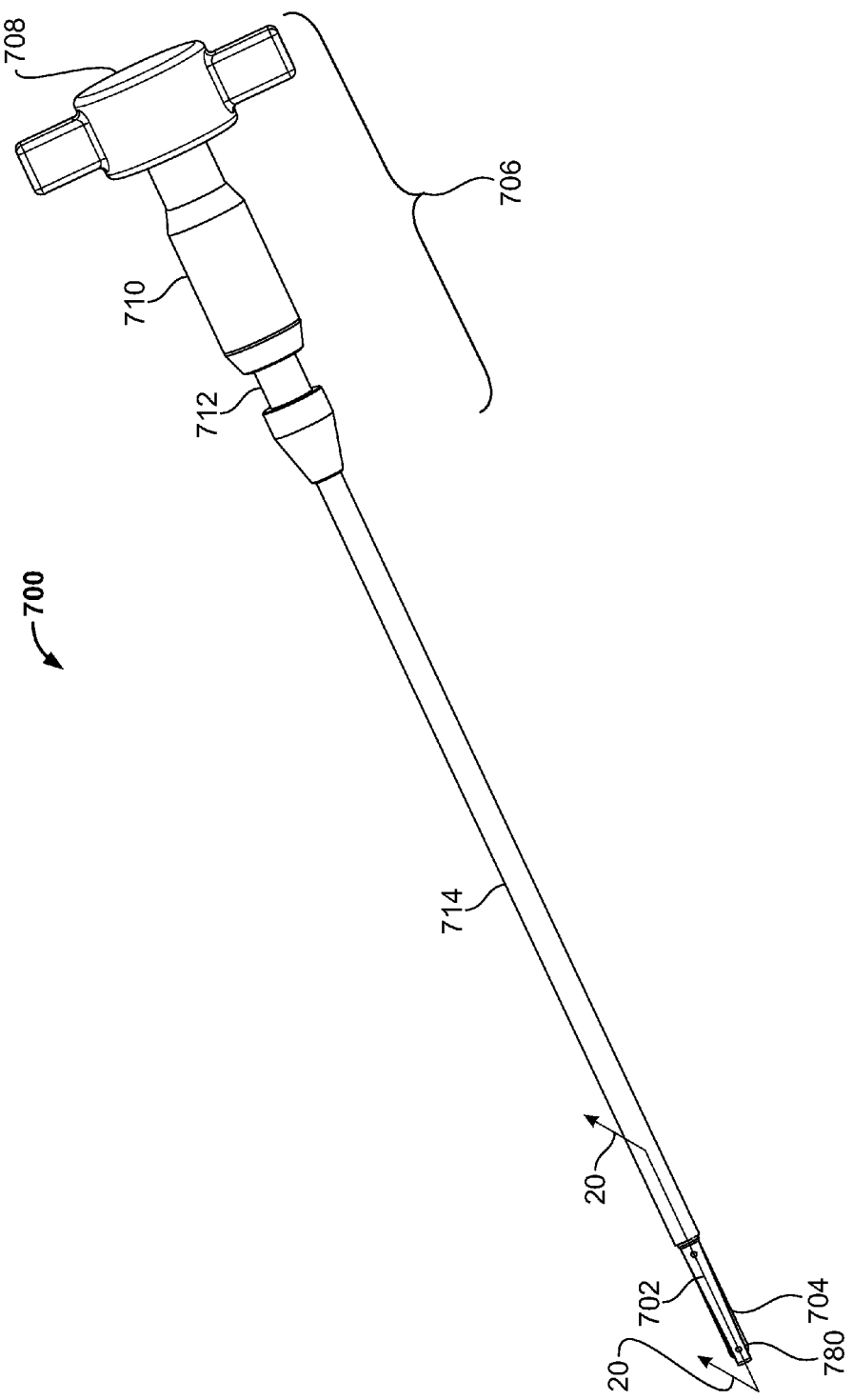
FIG. 7 shows a portion of the apparatus shown in FIG. 1 in a state that is different from the state shown in FIG. 1.

FIG. 7 shows illustrative intramedullary broach 700. Broach 700 may include broach head 702. Broach head 702 may include illustrative broaching member 704.

Broaching member 704 may be sufficiently rigid to displace cancellous bone $B_{CA}$. Broaching member 704 may be sufficiently flexible to be deformed by cortical bone $B_{CO}$. In some embodiments, broaching member 704 may be expandable. Broach head 702 may be supported by and rotated by shaft assembly 714. Broach control 706 may include drive handle 708 for rotating and translating broach head 702. Broach control 706 may include expansion control hub 710. Expansion control hub 710 may be displaceable along control shaft to expand or contract broaching member 704. Broach head 702 may include distal end 780. Expansion control hub 710 is shown in the "contract" position.

Figure 8:
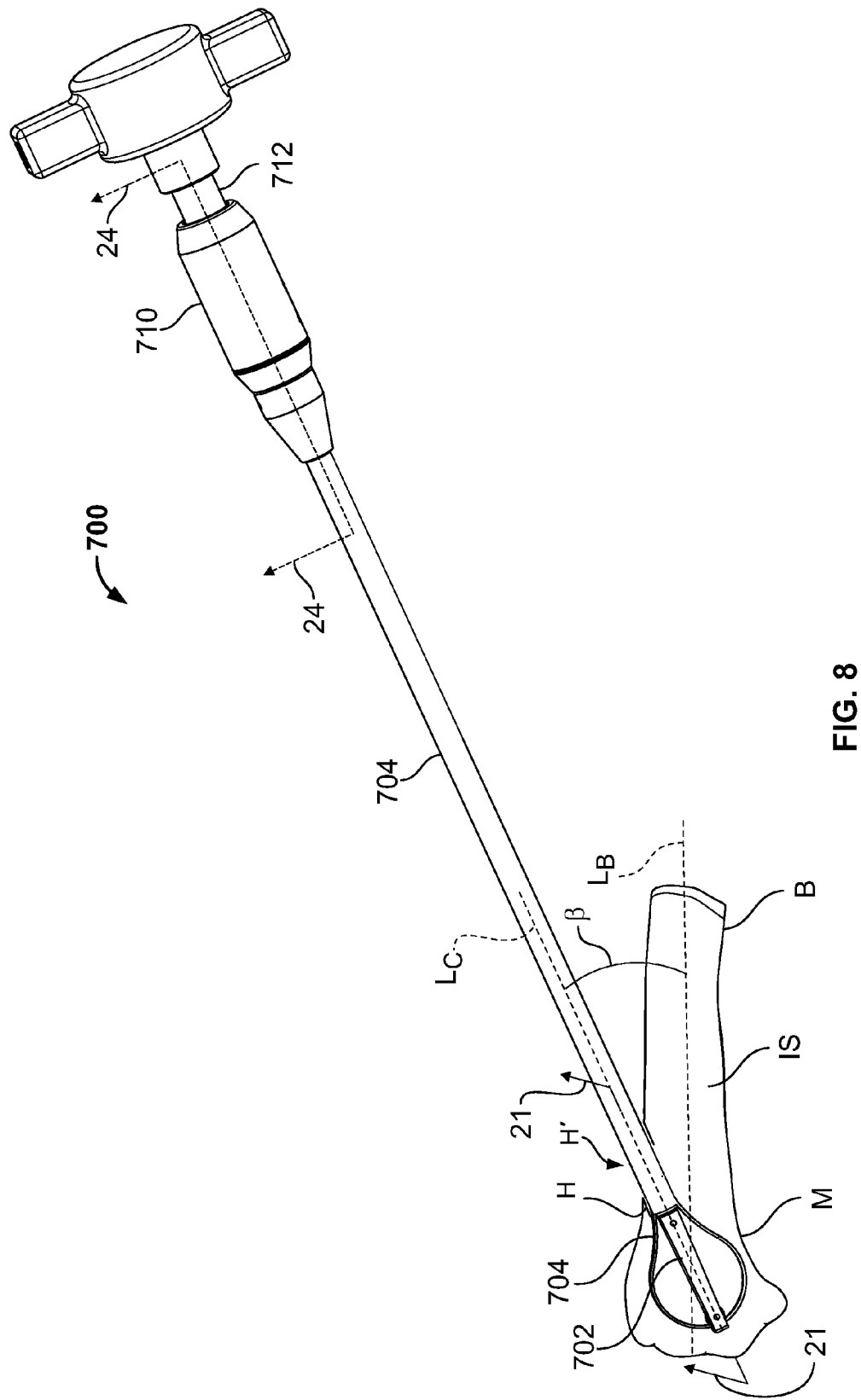
FIG. 8 shows a portion of the apparatus shown in FIG. 1.

FIG. 8 shows broach 700 deployed in bone B through hole H. Broach 700 may be deployed while broaching member 704 is contracted.

Broach head 702 may be advanced, through intramedullary space IS, into metaphyseal region M of bone B. Broach head 702 may be disposed in any portion of intramedullary space IS, such as in the end-bone.

Access hole H may be sufficiently small that it reduces the occurrence of cause stress risers at site H'. Expansion control hub 710 is shown in the "expand" position and broaching member 704 is shown expanded in bone B. Broaching member 704 may be expanded during or after deployment.

A standard orthopaedic drill instrument (not shown) may be used to open access hole H in cortical bone $B_{CO}$ (shown in FIG. 2) at site H' on bone B. The drill instrument may be guided by apparatus such as guide 100 (shown in FIG. 1). Axis hole H may be drilled along broach axis LC. Broach axis LC may form an angle β with bone axis LB. Broach 700 may be positioned such that broach axis Lc substantially coincides with guide tube axis LGT (shown in FIG. 1). Angle β may be an acute angle. Angle β may be complementary with angle α (shown in FIG. 1).

Figure 9:
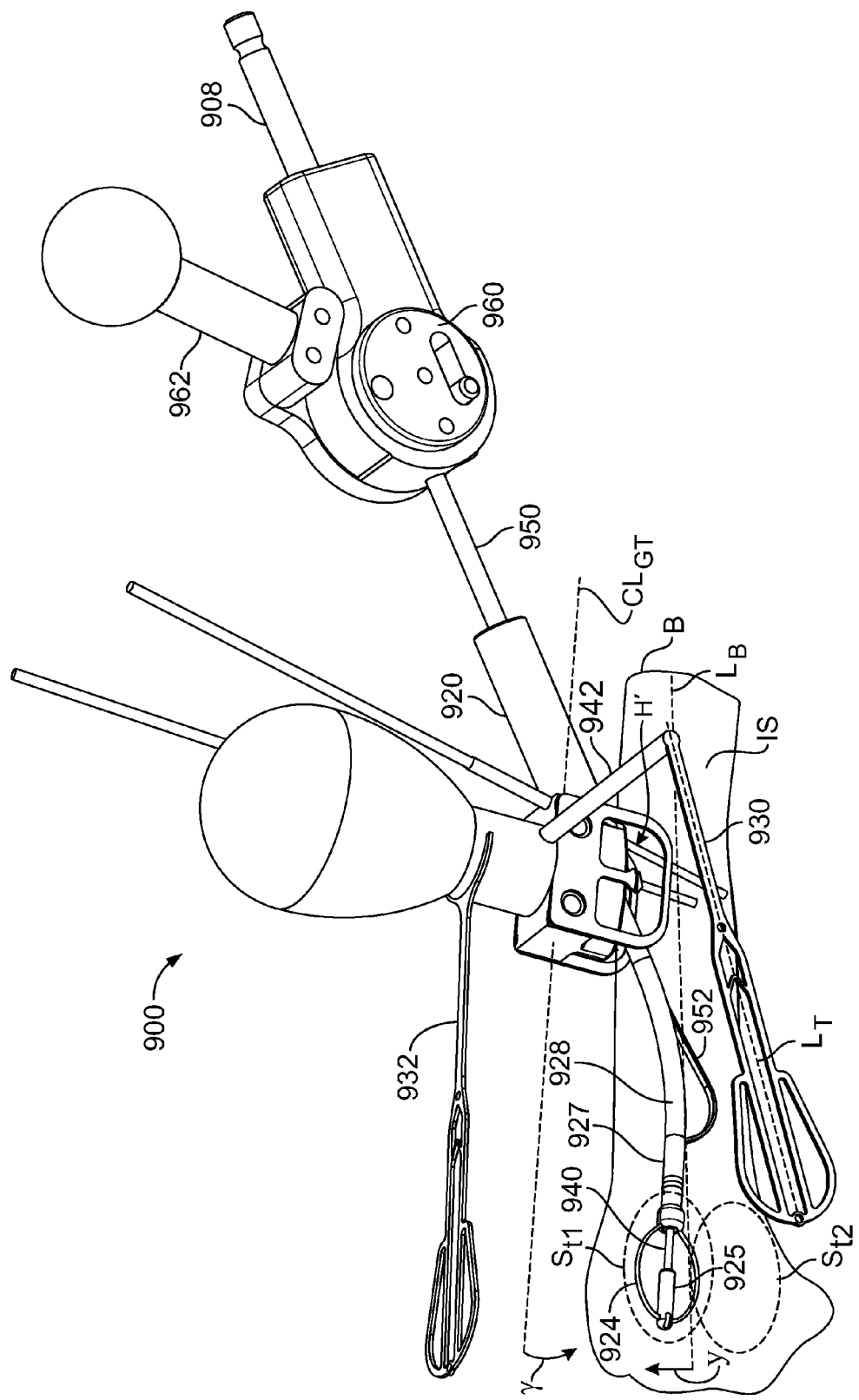
FIG. 9 shows a portion of the apparatus shown in FIG. 1 along with other apparatus in accordance with principles of the invention.

FIG. 9 shows illustrative instrument guide 900 at site H' on bone B. Instrument guide 900 may have one or more features in common with instrument guide 100 (shown in FIG. 1). Instrument guide 900 may include instrument templates 930 and 932 for positioning instrument guide 900 such that an instrument can be positioned at target region St1.

Illustrative steerable broach 950 may be deployed at target region St1 in intramedullary space IS by insertion through guide 900 at site H'. Broach 950 may include broach head 925. Broach head 925 may have one or more features or properties in common with broach head 125 (shown in FIG. 1). Broach head 925 may be supported by broach sheath 927. Broach head 925 may be rotated by drive shaft 940 which may extend inside broach sheath 927 and receive torque from torque adapter 908. Torque adapter 908 may provide rotation from any suitable rotation source drive shaft 940.

Broach sheath 927 may be flexible. Broach sheath 927 may be flexible in region 928 such that application of off-axis tension by elevator ribbon 952 may position broach head 925 at a distance y or −y relative to bone axis LB. Illustrative elevator control body 960 may apply axial compression to elevator ribbon 952 to cause broach sheath 927 to bend.

Broach sheath 927 may be configured to flex in more than one plane. Broach sheath 927 may be configured to flex substantially in one plane only.

Target region St1 could be in either, or both, of cancellous bone $B_{CA}$ and cortical bone $B_{CO}$ (shown in FIG. 2). Side template 930 and top template 932 are registered to guide tube 920. A practitioner may position templates 930 and 932 such that templates 930 and 932 "project" onto target region St1 so that guide 900 will guide broach head 925 to target region St1.

Side template 930 may be rotatable at arm 942 to change angle γ between side template 930 axis $L_T$ and guide 900 centerline $CL_{GT}$. γ may be selected to correspond to a degree of elevation in direction y or −y of broach head 925. γ may be selected to correspond to a degree of actuation of control 962 of control body 960. For example, γ may be selected such that side template 930 "projects" onto target region St2.

Fluoroscopic imaging may be used to position templates 930 and 932 relative to target region St1.

A practitioner can select the position of H' (distance $x_H$ shown in FIG. 2), the angle of hole H (shown in FIG. 2) relative to bone axis LB, the degree and distribution of flexing in region 928, the penetration of broach sheath 927, the size of broach head 925, the swept-out profile of broaching member 924, and any other suitable parameters, to determine the size, shape, orientation and location of a cavity to be swept out by broaching member 924. For example, one or more of the aforementioned parameters may be selected to position broach head 925 in target region St2.

FIG. 10 shows guide base 102 from below on the distal side. Stem 116 extends from the top of base 102. Guide tube 120 extends from the distal portion of base 102. Arm 131 extends from the side of base 102. Site H' of hole H (shown in FIG. 2) is shown projected onto opening 1002 of guide tube 120 and centered about axes LH and LGT.

Illustrative contacts 108 and 110 extend down from base 102 to engage bone B (shown in FIG. 2) and resist rotation about vertical axes $L_H$ and $L_{TR}$ and translation along guide centerline $CL_G$. Contacts 108 and 110 may be sufficiently sharp to penetrate or partially penetrate bone B. Cleats 112 and 114 may engage the surface of bone B and resist rotation about guide centerline $CL_G$. Base 102 may support any suitable number of contacts in any suitable pattern or location. Base 102 may support an arrangement of contacts that extends in a direction that is substantially oblique or transverse to guide centerline $CL_G$.

In some embodiments, base 102 may include a flange (not shown) that saddles bone B. The flange may include any suitable number of contacts in any suitable pattern, including an arrangement of contacts that extends in a direction that is substantially oblique or transverse to guide centerline $CL_G$.

Alignment members 104 and 106 may extend from base 102 to align guide centerline CLG of guide 100 with bone centerline CLBS of the top surface of bone B (shown in FIG. 2). Each of alignment members 104 and 106 include continuous alignment edges 1004 and 1006. Edge 1004 is supported by substantially vertical struts 1007 and 1008. Edge 1006 is supported by substantially vertical struts 1010 and 1012. Edges 1004 and 1006 are substantially parallel to centerline CLG.

In some embodiments, alignment members may be or may include tines that correspond to struts 1007, 1008, 1010 and 1012. One or more of the tines may extend straight down from base 102. One or more of the tines may extend down and in the proximal direction relative to base 102. One or more of the tines may extend down and in the distal direction relative to base 102.

In embodiments that include one or more tines (not shown), edges 1004 and 1006 may be absent. In those embodiments, the tines may flex independently of each other. One or more of the tines may be biased away from guide centerline CLG. One or more of the tines may be biased toward guide centerline CLG. One or more of the tines may be curved or arcuate.

Some embodiments may include a bushing (not shown) in guide tube 120. The bushing may provide stability for a K-wire in procedures in which the K-wire is used as a drill to provide preliminary access to the inside of a bone.

Figure 11:
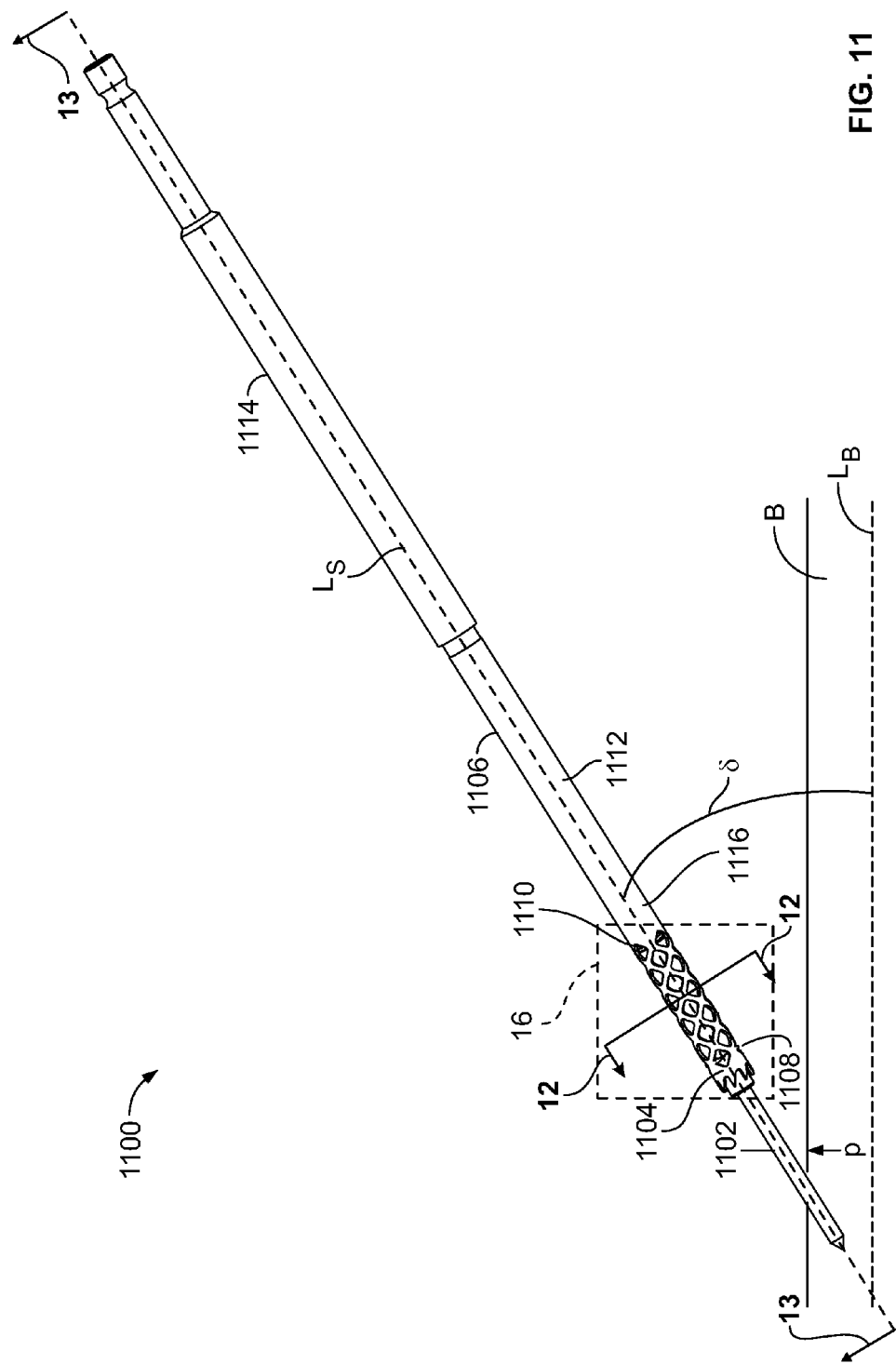
FIG. 11 shows other illustrative apparatus in accordance with principles of the invention.

FIG. 11 shows illustrative saw 1100. Saw 1100 may be used to cut an access hole at site H' or site I' (shown in FIG. 2) or any other suitable hole. Saw 1100 may be guided by guide 100 (shown in FIG. 1), guide 900 (shown in FIG. 9), guide 1900 (shown in FIG. 19) or any other suitable guide.

Saw 1100 may include wire 1102. Wire 1102 may be a K-wire or any other suitable wire. Saw 1100 may include centering sleeve 1104. Centering sleeve 1104 may be made of polymer, alloy or any other suitable material. Saw 1100 may include cutting member 1106. Cutting member 1106 may include teeth 1108, vents 1110 and cylindrical member 1112. Vents 1110 may provide chip clearance, side-cutting, reduced heating or other properties, among others. Saw 1100 may include torque adapter 1114. Torque adapter 1114 may transmit rotation from a rotation source to one or both of K-wire 1102 and cutting member 1106.

Wire 1102 may form an angled pilot hole in bone B. The hole may be formed at angle δ between saw axis $L_s$ and bone axis $L_B$. After wire 1102 penetrates bone B, saw 1100 may be advanced distally until teeth 1108 engage bone B and being to cut. Teeth 1108 will engage bone B first at point p, in the crotch between wire 1102 and bone B. Teeth 1108 may therefore be subjected to a contact force from bone B that is oblique to a plane defined by teeth 1108. Centering sleeve 1104 may support teeth 1108 against the oblique force and maintain teeth 1108 at a substantially constant radius from axis $L_s$ during the formation of an access hole.

A spring 1116 (shown in FIG. 13) may urge centering sleeve 1104 distally to keep centering sleeve 1104 at or near bone B as teeth 1108 penetrate into bone B.

Figure 12:
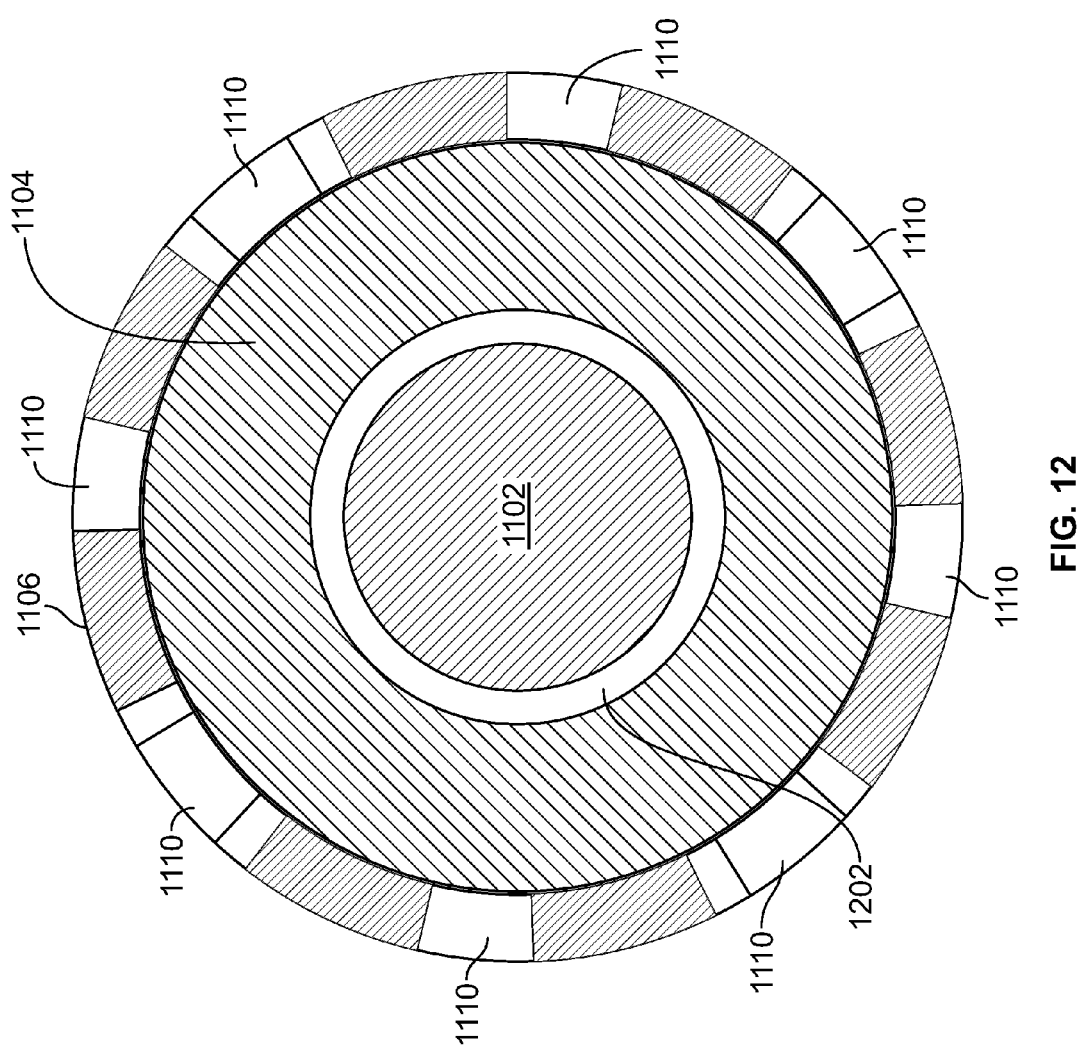
FIG. 12 shows a partial cross-sectional view, taken along lines 12-12 (shown in FIG. 11), of the apparatus shown in FIG. 11.

FIG. 12 shows that centering sleeve 1104 may be coaxially arranged within cutting member 1106. Wire 1102 may be coaxially arranged within centering sleeve 1104. Collar 1202 of centering sleeve 1104 may be provided at a distal end of centering sleeve 1104 to provide a close tolerance between wire 1102 and centering sleeve 1104.

Figure 13:
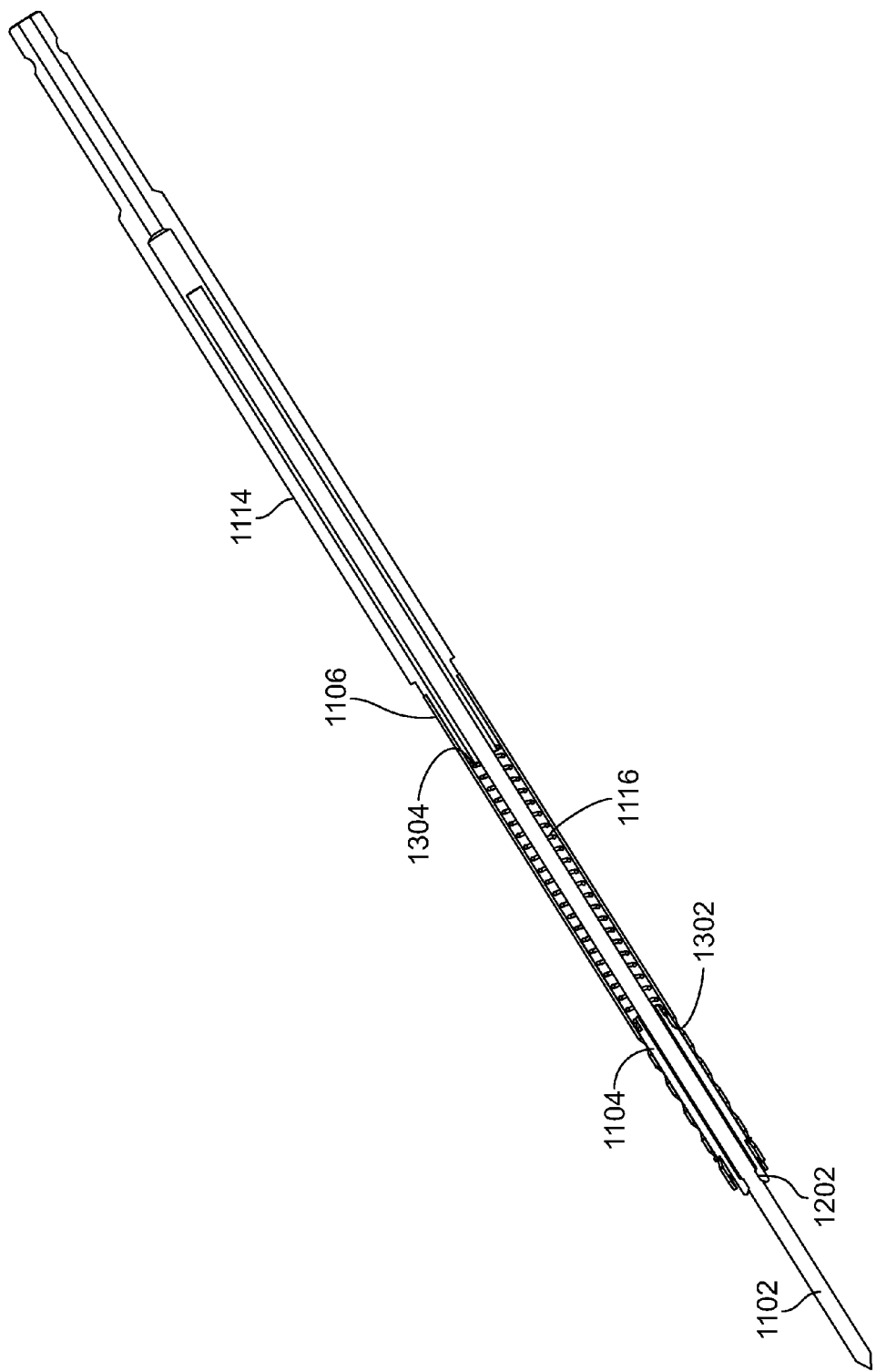
FIG. 13 shows a partial cross-sectional view, taken along lines 13-13 (shown in FIG. 11) of the apparatus shown in FIG. 11.

FIG. 13 shows spring 1116 compressed between proximal face 1302 of centering sleeve 1104 and distal face 1304 of torque adapter 1114.

In some embodiments, wire 1102 may be used to drill a pilot hole in bone B without apparatus such as centering sleeve 1104 and cutting member 1106. In such embodiments, a bushing (not shown) may be provided in a guide tube such as guide tube 120 (shown in FIG. 1). Wire 1102 may be placed through the bushing and driven by a torque adapter such as 1114. The bushing may have a bore that is sized to stabilize a K-wire driven in rotation by a surgical drill.

It may be desirable thereafter to cut in the bone a hole that is substantially coaxial with the K-wire. After the K-wire is drilled into the bone, in such embodiments, the bushing (not shown) may be removed from the guide tube to allow a coring saw to advance through the guide tube.

Figure 14:
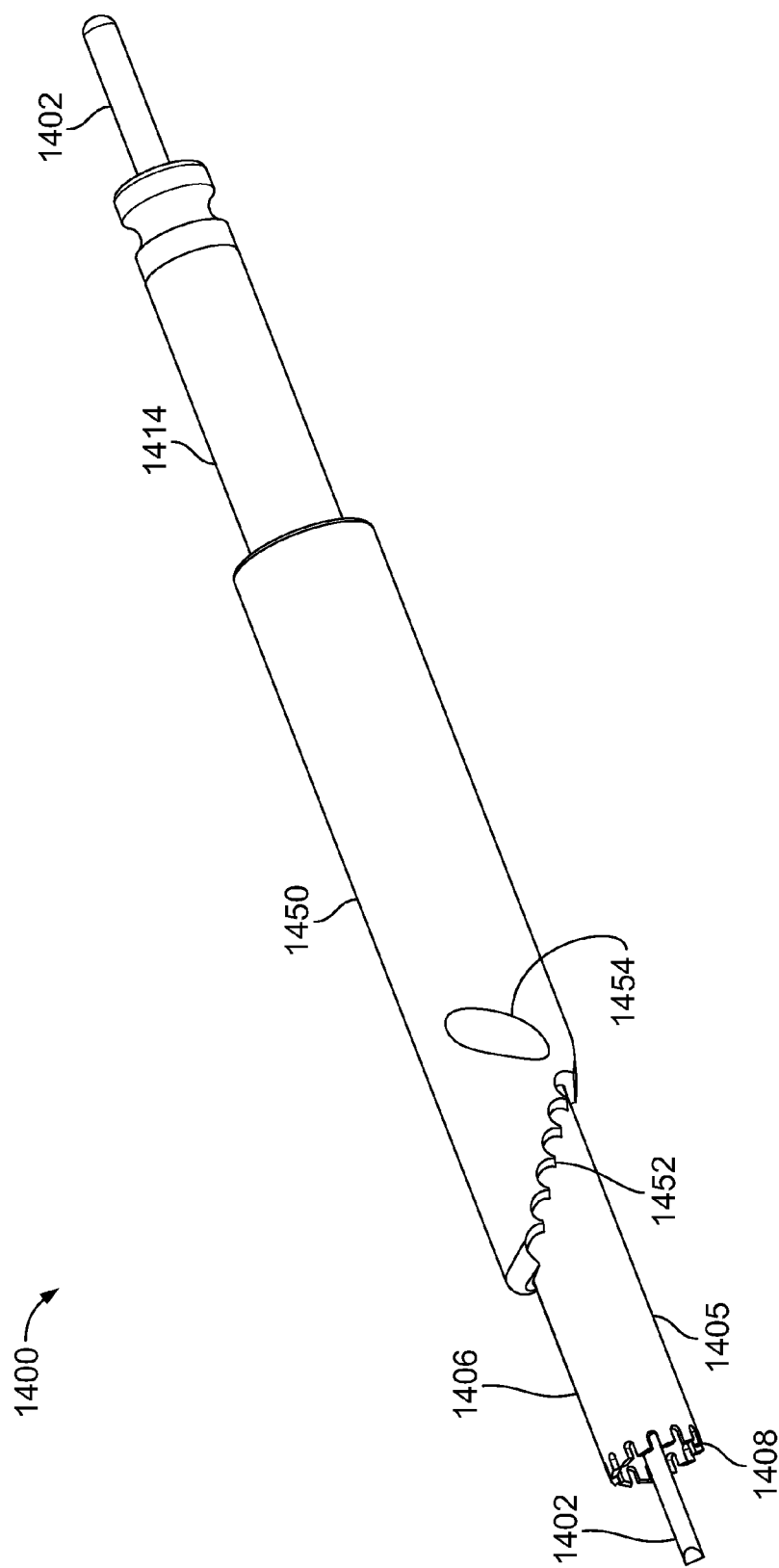
FIG. 14 shows other illustrative apparatus in accordance with principles of the invention.

FIG. 14 shows illustrative apparatus 1400 for cutting in bone B a hole that is substantially coaxial with wire 1402. FIG. 14 shows a relevant portion of coring saw guide 1450. Coring saw guide 1450 may include contacts 1452 for engaging a surface of bone B (shown in FIG. 2). Coring saw guide 1450 may include handle-mounting recesses such as 1454. A centering sleeve (not shown) may be disposed coaxially between wire 1402 and cutting member 1406. In some embodiments, a cutting member such as 1406 may be engaged by a collar (not shown) that is configured for delivery of torque.

A proximal end of wire 1402 may be engaged in a hand drill fitting and rotatingly driven into the bone as it is advanced distally through saw guide 1450.

Figure 15:
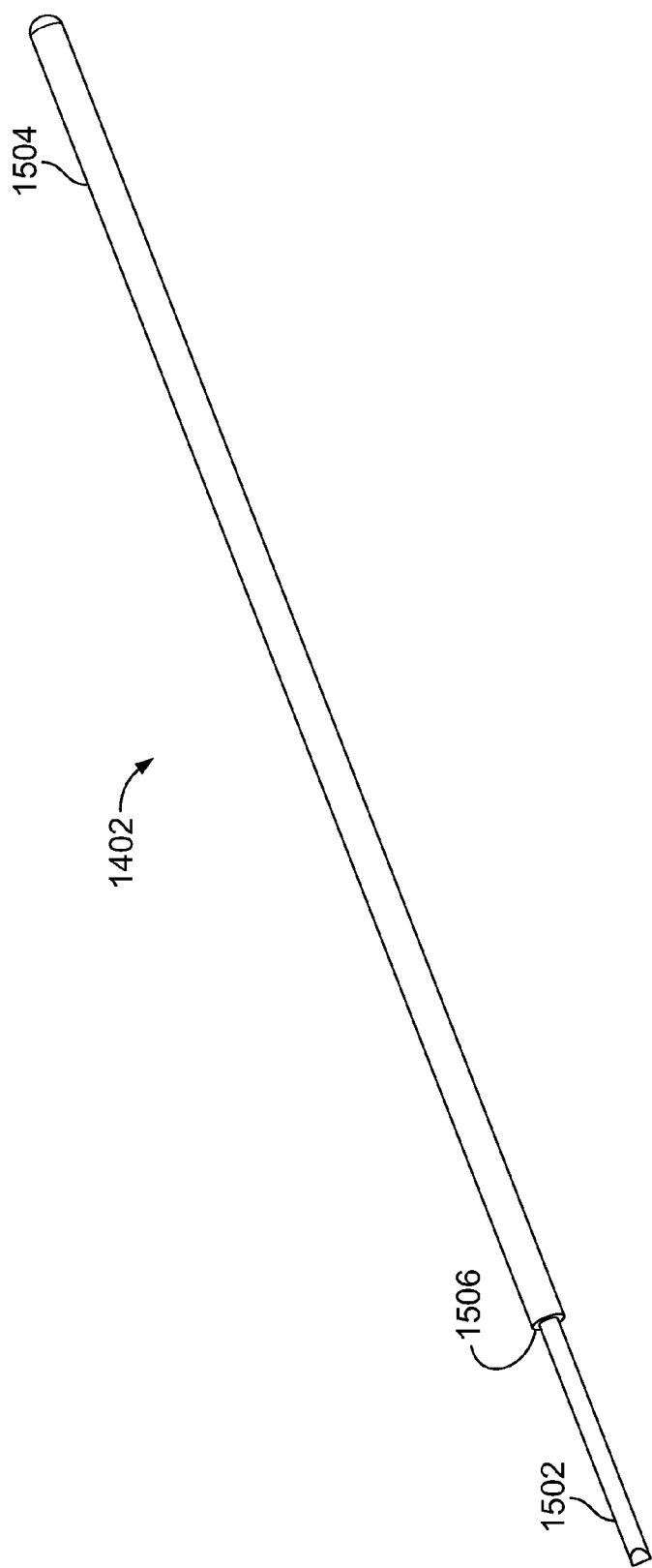
FIG. 15 shows a portion of the apparatus shown in FIG. 14.

FIG. 15 shows wire 1402. Distal end 1502 of wire 1402 may have a first diameter. Proximal end 1504 of wire 1402 may have a second diameter that is greater than the first diameter. Step 1506 between the first diameter and the second diameter may be used as a stop to limit the extent to which wire 1402 may be driven into bone B.

Proximal end 1504 of a wire such as 1402 may extend along and through a cannula in an A-O type adapter while the adapter drives a cutting member such as 1408 distally into a bone.

In some embodiments, step 1506 may be used to distally eject a bone plug from the interior of distal end 1405 of cutting member 1406 after a hole is cut and cutting member 1406 is withdrawn from the bone.

In some embodiments, a soft-tissue protector (not shown) may be provided to keep soft tissue proximate the access hole from becoming engaged by rotating apparatus. The protector may include a cannula for guiding the rotating apparatus into the hole. The protector may include a flange that "funnels" the apparatus into the cannula and blocks the soft tissue from approaching the apparatus.

Figure 16:
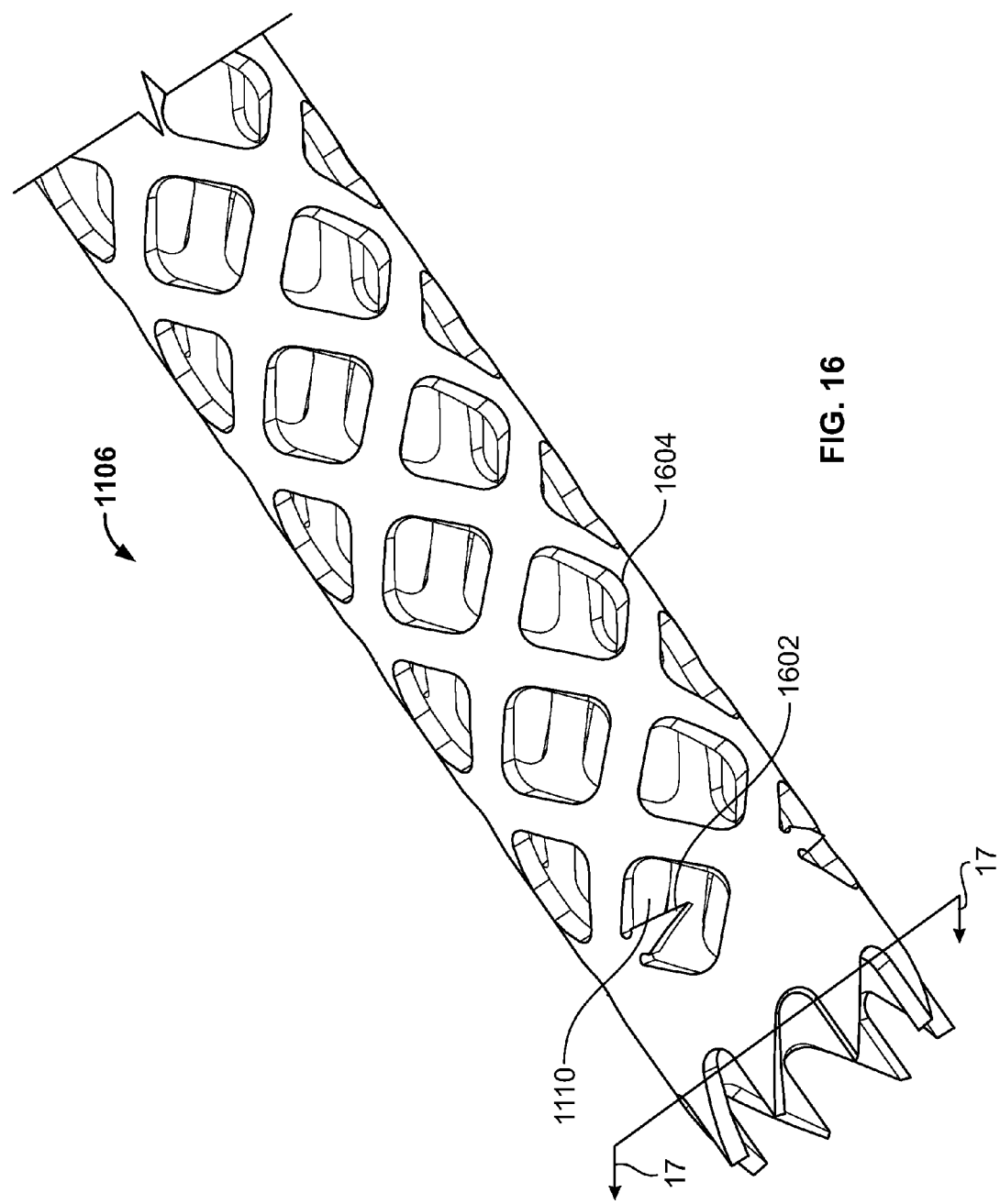
FIG. 16 shows a portion (labeled "16") of the apparatus shown in FIG. 11.

FIG. 16 shows a portion of illustrative cutting member 1106 from region 16 of FIG. 11. A circumferential tooth 1602 may extend into one or more of vents 1110 to engage bone on the inside of the cutter.

Tooth 1602 may provide friction between cutting member 1106 and the bone plug and may facilitate removal of the bone plug upon with withdrawal of cutting member 1106 from the access hole. The distal end of the bone plug may not be severed from bone B native tissue by cutting member 1106. Tooth 1602 may provide one or both of torsional and axial force to sever the plug from bone B. Vents 1110 may include vent edges 1604. Vent edges 1604 may cut a wall of the access hole.

Tooth 1602 may provide friction between cutting member 1106 and centering sleeve 1104. The friction may resist proximal motion of centering sleeve 1104.

Figure 17:
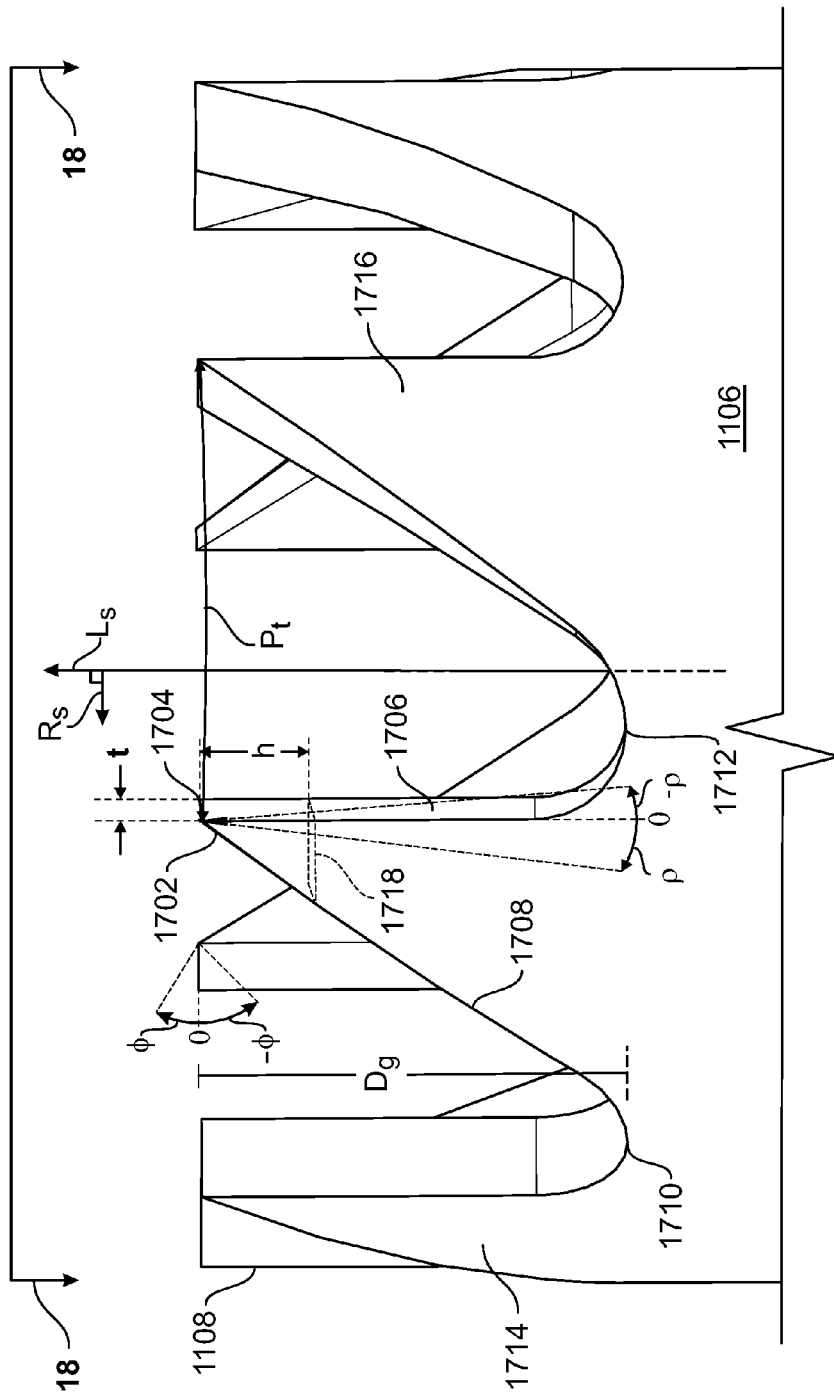
FIG. 17 shows a view, taken along lines 17-17 (shown in FIG. 16) of a portion of the apparatus shown in FIG. 16.

FIG. 17 shows illustrative teeth 1108 of cutter member 1106 (shown in FIG. 11). Illustrative tooth 1702 may include cutting edge 1704, face 1706 and back 1708. Face 1706 and back 1708 may partially define adjacent gullets 1710 and 1712, which intervene between tooth 1702 and neighboring teeth 1714 and 1716, respectively. Tooth 1702 may have thickness t. Tooth 1702 may be circumferentially set apart from neighboring tooth 1716 by pitch Pt. Cutting edge 1704 may be angled relative to saw radial direction $R_s$ by bevel angle φ (shown on a different tooth). Cutting edge 1704 is shown with φ=0°, but any suitable φ may be used. Face 1706 may have longitudinal rake angle ρ.

Larger rake angles (e.g., positive) may produce lower forces, but smaller included tooth angles, and therefore lower heat capacity. Smaller rake angles (e.g., negative) may increase heat capacity and increase heat generated in shearing but increase cutting forces.

Face 1706 is shown with ρ=0°, but any suitable ρ may be used. Gullet 1710 may have gullet depth $D_g$.

In some embodiments, tooth 1702 may include facet 1718 (shown in broken line). When facet 1718 is present, tooth face 1706 may be shortened by distance h. Facet 1718 may have a normal (not shown) that is oriented at any suitable angle relative to axis $L_s$ and radius $R_s$.

Figure 18:
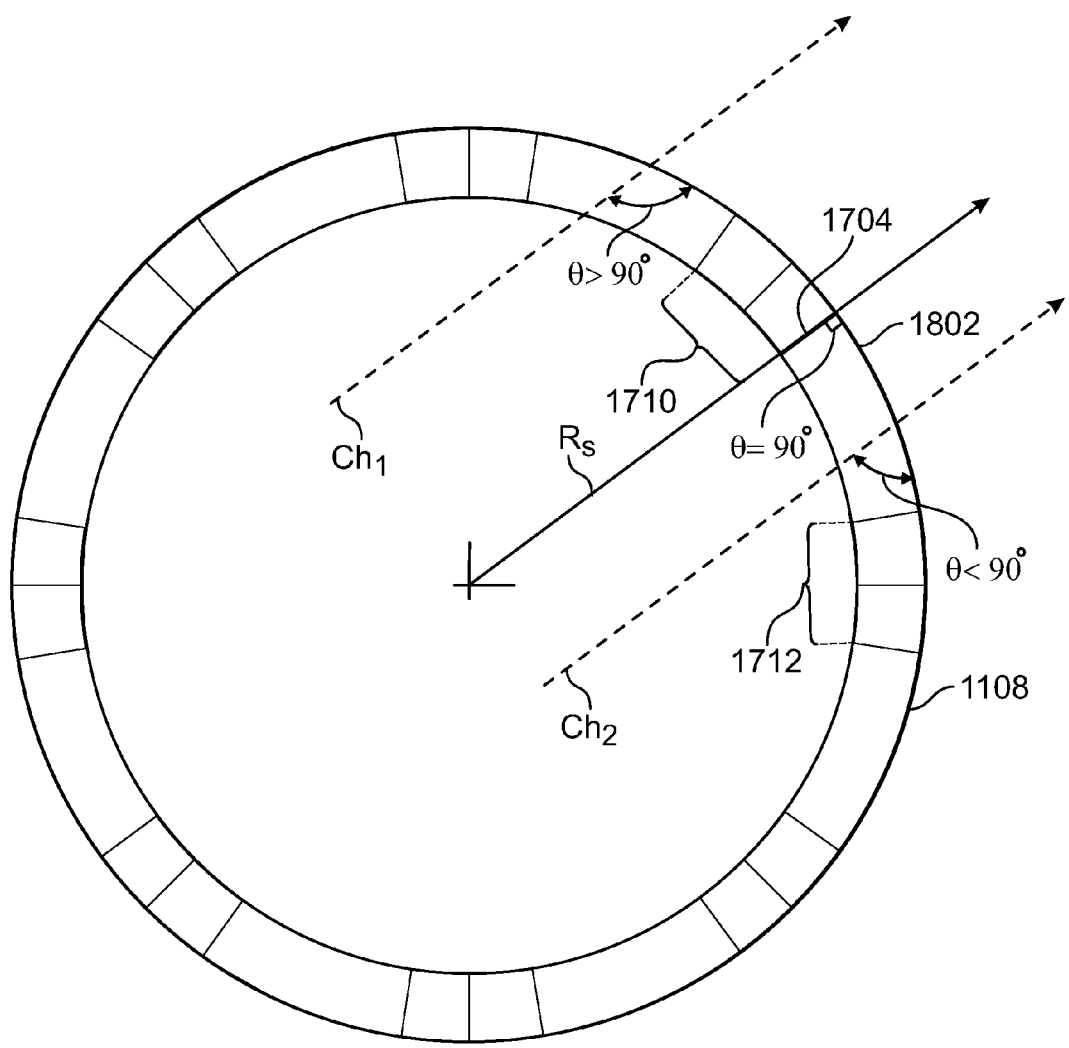
FIG. 18 shows a view, taken along lines 18-18 (shown in FIG. 17) of the apparatus shown in FIG. 17.

FIG. 18 shows teeth 1108 (shown in FIG. 11) as viewed along lines 18-18 (shown in FIG. 17). Cutting edge 1704 forms angle θ with saw outer wall 1802. Cutting edge 1704 is shown with θ≈90°, but any suitable θ may be used. For example, a tooth formed by cutting along chord $Ch_1$ may create a cutting edge having θ>90°. A tooth formed by cutting along chord $Ch_2$ may create a cutting edge having θ<90°.

In some embodiments, a cutting member may have bi-directionally cutting teeth. Each tooth such tooth may have a right and a left cutting edge. When the coring saw rotates clockwise, a right edge cuts. When the coring saw rotates counterclockwise, a left edge cuts.

Figure 19:
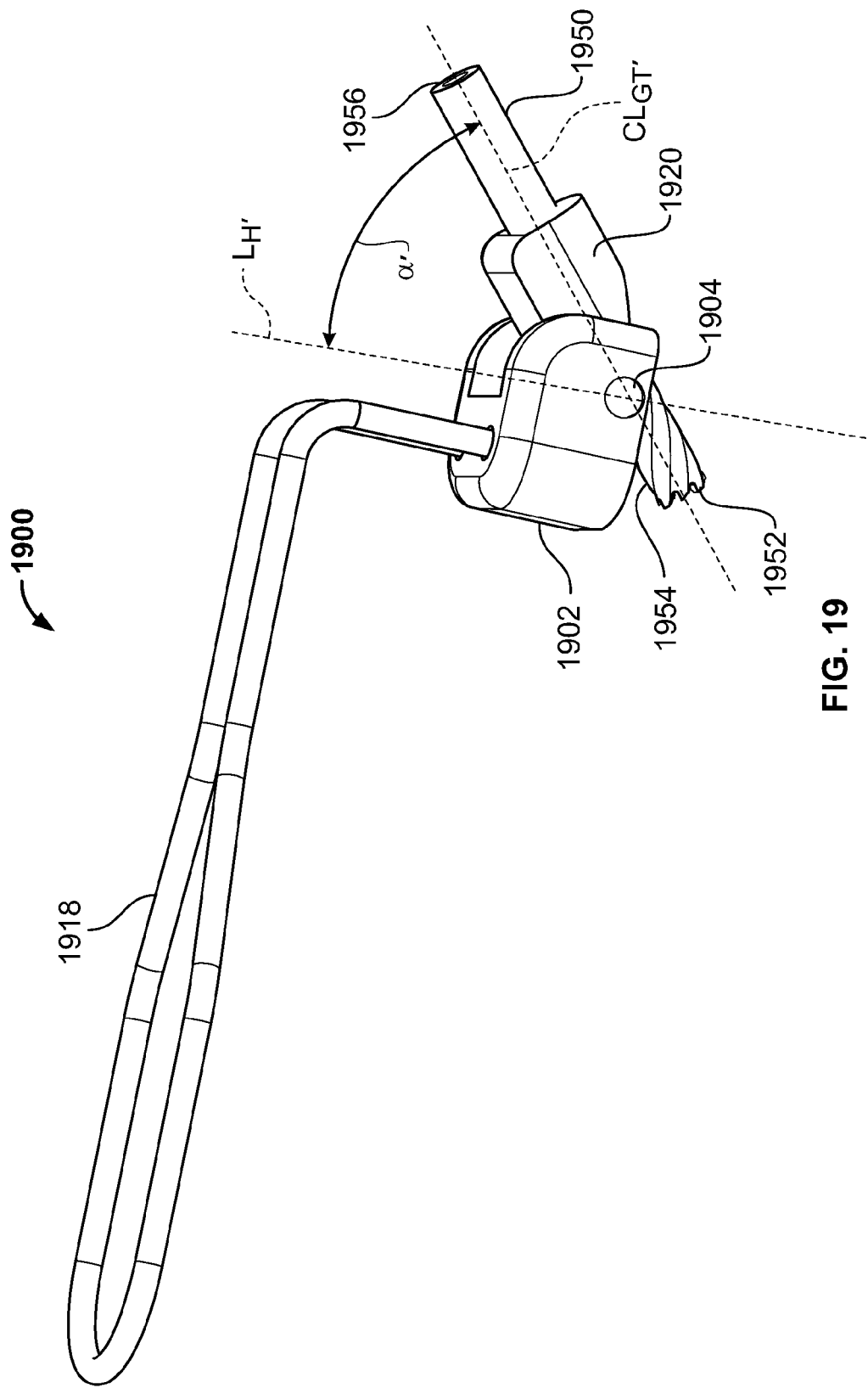
FIG. 19 shows other illustrative apparatus in accordance with principles of the invention.

FIG. 19 shows illustrative instrument guide 1900. Illustrative instrument guide 1900 may have one or more features in common with one or more of guide 100 (shown in FIG. 1) and guide 900 (shown in FIG. 9). Guide 1900 may be used to guide an instrument into bone B at a site such as H' or I' (shown in FIG. 2).

Guide 1900 may include base 1902. Base 1902 may be placed against bone B (shown in FIG. 2) at site H'. Base 1902 may include contacts (not shown), alignment members (not shown), cleats (not shown) or any other suitable features. Grip 1918 may extend from base 1902. Base 1902 may include pivot 1904. Pivot 1904 may pivotably support guide tube 1920. Guide tube 1920 centerline $CL_{GT'}$ may be positioned at any suitable angle α' relative to axis $L_{H'}$ so that saw 1950 may be advanced through bone B (not shown) at angle α'. The intersection of axis $L_{H'}$ and $CL_{GT'}$ may substantially coincide with site H' or site I' for different values of α'. A practitioner may change angle α' before or during penetration of saw 1950 into bone B. For example, a practitioner may initiate a pilot hole at α'≈0° and then change α' to obtain the desired angle for the access hole.

Saw 1950 may include teeth 1952, flutes 1954, cannula 1956 or any other suitable features, including the features described and shown herein in connection with other saws.

Figure 20:
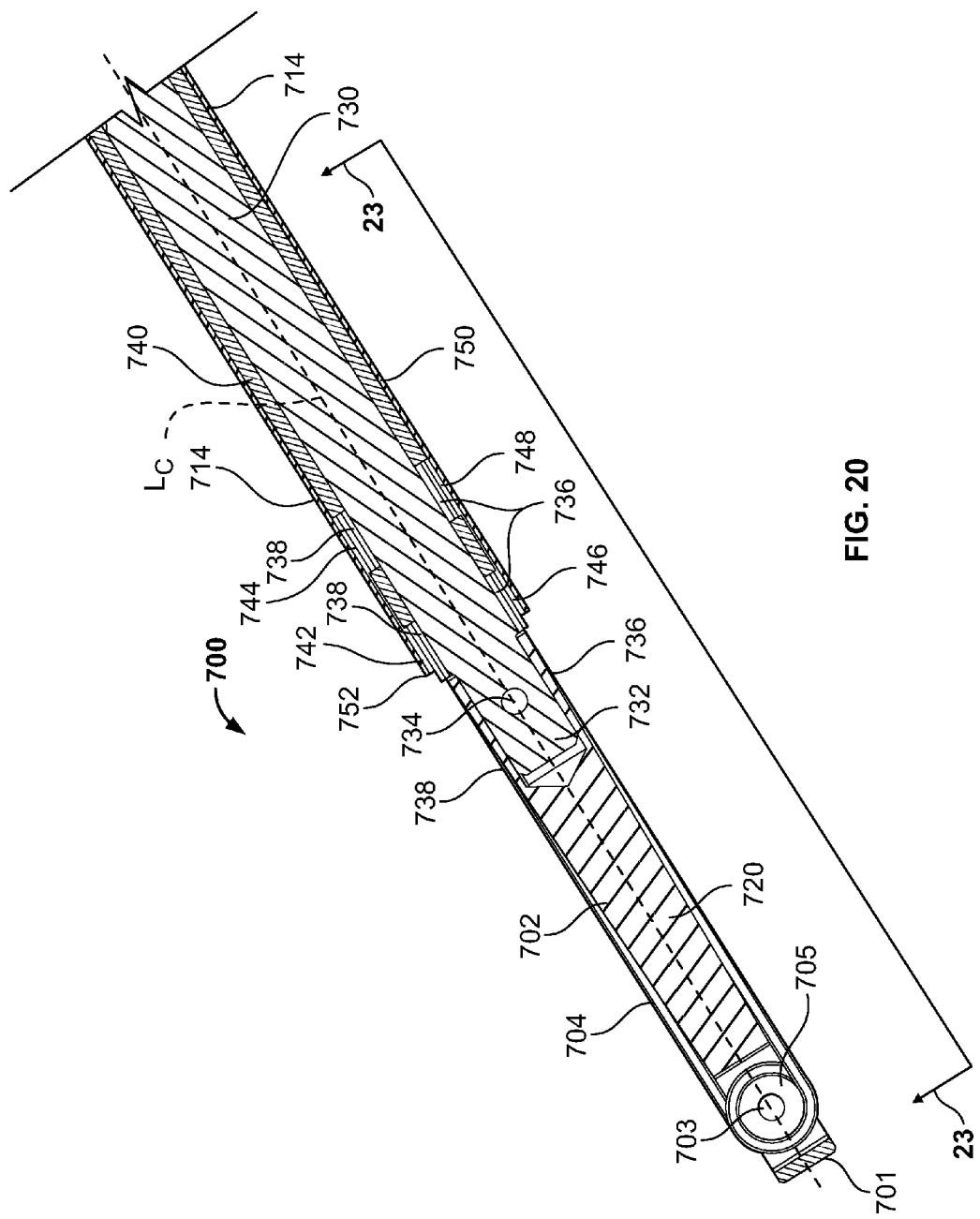
FIG. 20 shows a partial cross-sectional view, taken along lines 20-20 (shown in FIG. 7) of the apparatus shown in FIG. 7.

FIG. 20 shows a view of a distal portion of broach 700 taken along lines 20-20 (shown in FIG. 7). Pin 703 may be located near the distal end of bracket 720. Pin 703 may fix the position of the distal end of broaching member 704. Pin 703 may support cylindrical form 705. Cylindrical form 705 may be coaxially mounted on pin 703. Cylindrical form 705 may support a spiral segment of broaching member 704. One or more distal portions of broaching member 704 may be welded or otherwise suitably fixed to cylindrical form 705.

Cylindrical form 705 may constrain or partially constrain the orientation of distal portions of broaching member 704. Cylindrical form 705 may be fixed relative to bracket 720. Cylindrical form 705 may be rotatable relative to bracket 720.

Broach head 702 may include end cap 701. Broaching member 704 may remove tissue that is generally proximal end cap 701. In some embodiments, member 704 may expand in such a manner as to extend distally of end cap 701. In such embodiments, the broaching member may remove tissue that is distal of end cap 701.

Reducing or minimizing the distance between the distal end of broaching member 704 and end cap 701 may allow broaching member 704 to remove tissue that is more immediately proximal end cap 701. End cap 701 may be positioned at the distal end of bracket 720. End cap 701 may be configured to have a smooth, atraumatic surface. Bracket 720 may be attached to drive shaft 730.

Shaft assembly 714 may include drive shaft 730. Drive shaft 730 may support bracket 720 at union 732. Drive shaft 730 may be secured to bracket 720 by pin 734. Drive shaft 730 may provide rotation to broach head 702.

Proximal ends 736 and 738 of broaching member 704 may be fixed to slide 740, which may be a tube. Proximal end 738 may be threaded through or keyed into windows 742 and 744 in slide 740. Proximal end 736 may be threaded through or keyed into slots 746 and 748 in slide 740. Slide 740 may slide relative to drive shaft 730 to expand and contract broaching member 704. Slide 740 is shown in the "contract" state, in which broaching member 704 is drawn close to bracket 720. Slide cover 750 may slide with slide 740. One or both of slide 740 and slide cover 750 may be translated along axis $L_c$ by control hub 710 (shown in FIG. 7) or any other suitable position controller.

Slide cover 750 may remain stationary relative to drive shaft 730 when slide 740 slides relative to drive shaft 730. In embodiments in which slide cover 750 remains stationary when slide 740 moves, distal end 752 of slide cover 750 may limit the radial position of broaching member 704 at a fixed distance along drive shaft 730 and thus affect the deformation of broaching member 704 in the expanded state.

Broaching member 704 may undergo one or both of elastic and plastic deformation.

Figure 21:
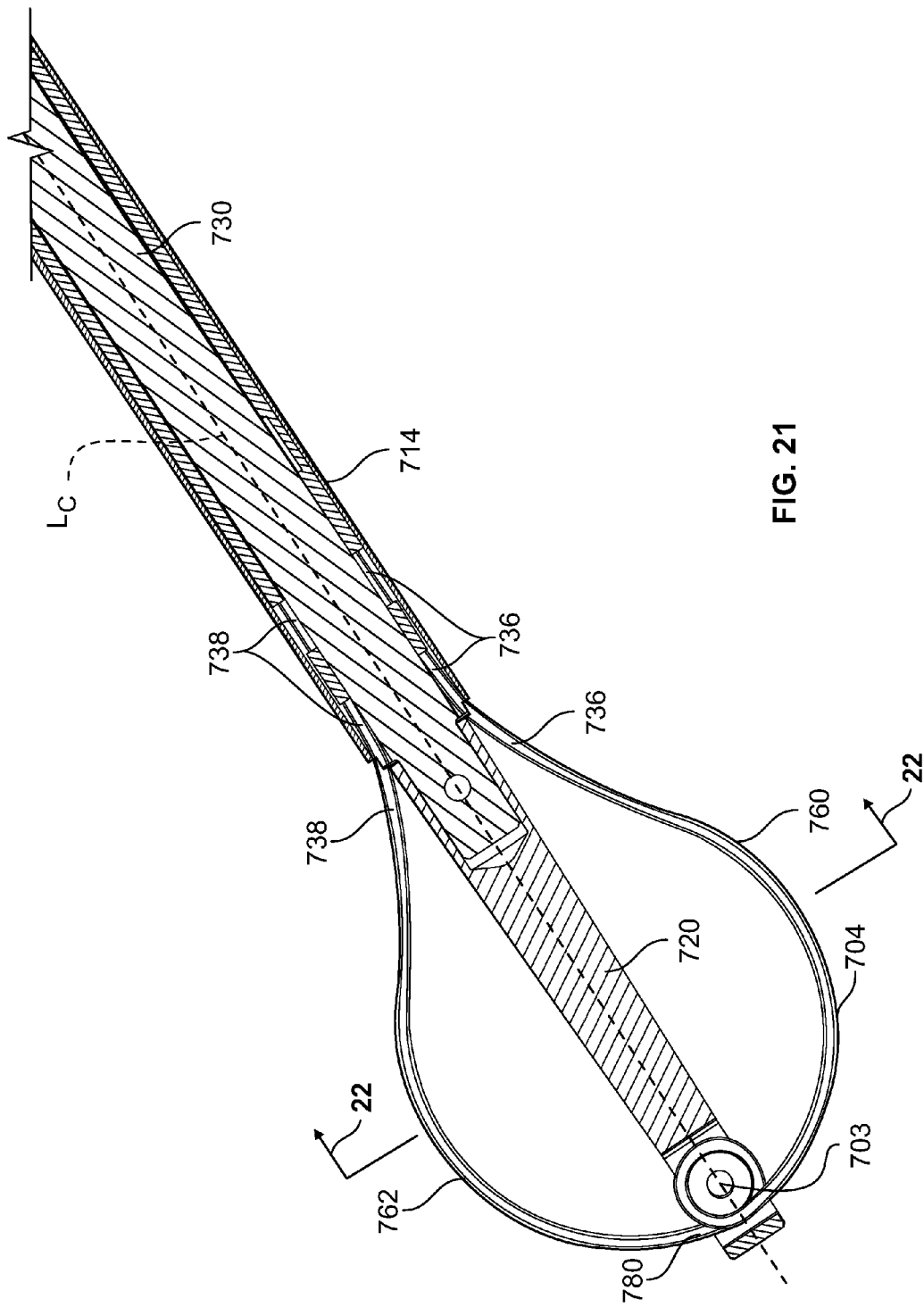
FIG. 21 shows a partial cross-sectional view, taken along lines 21-21 (shown in FIG. 8) of the apparatus shown in FIG. 8.

FIG. 21 shows a view of a distal portion of broach 700 taken along lines 20-20 (shown in FIG. 7) when broaching member 704 is in an expanded state. Broaching member 704 is shown as mainly circular. However, any desired shape may be able to be imparted in the expanded state such as but not limited to: square, triangular, oval, ellipsoid, teardrop, football, or any other suitable shape.

Different shapes may be obtained using several methods, such as utilizing a pre-set shape in a shape memory alloy, modifying the geometry of the member cross-section (along the member length) such that it preferentially bends in a desired manner, constraining broaching member 704 (e.g., in force, shear or moment) in a way that forces the expansion to take desired shape, having the final shape be that of the expanded geometry and the reduced or collapsed geometry be that of a higher strain configuration, and/or any other suitable method of forming a desired shape.

For example, largely or substantially preventing radial movement of broaching member proximal ends 736 and 738, and allowing movement of the distal end of broaching member 704 generally about pin 703 while elastically deforming broaching member proximal ends 736 and 738, due to reducing the distance between the distal end and proximal ends 736 and 738 of broaching member 704, may modify the geometry of broaching member 704 from a generally straight configuration to a generally eggbeater shape.

The deformation may relatively increase the distance between (a) sections 760 and 762 and (b) bracket 720. As this distance is increased, the swept-out volume of broaching member 704, as broaching member 704 rotates generally about an axis such as $L_c$ (shown in FIG. 8), is increased.

In some embodiments, a broach may include a broaching member that includes one or more stiff tines (not shown) that is joined to a drive shaft. The drive shaft may have a longitudinal axis. The tine may be joined to the drive shaft radially close to the axis at a proximal end of the tine. The tine may have a distal end that is spaced radially apart from the axis. The distal end of the tine may be distal of the distal end of the drive shaft. There may be numerous tines on the drive shaft. Such embodiments may be appropriate for rotation in intramedullary space IS of bone B (shown in FIG. 2) using high torque at low rotational speeds.

Figure 22:
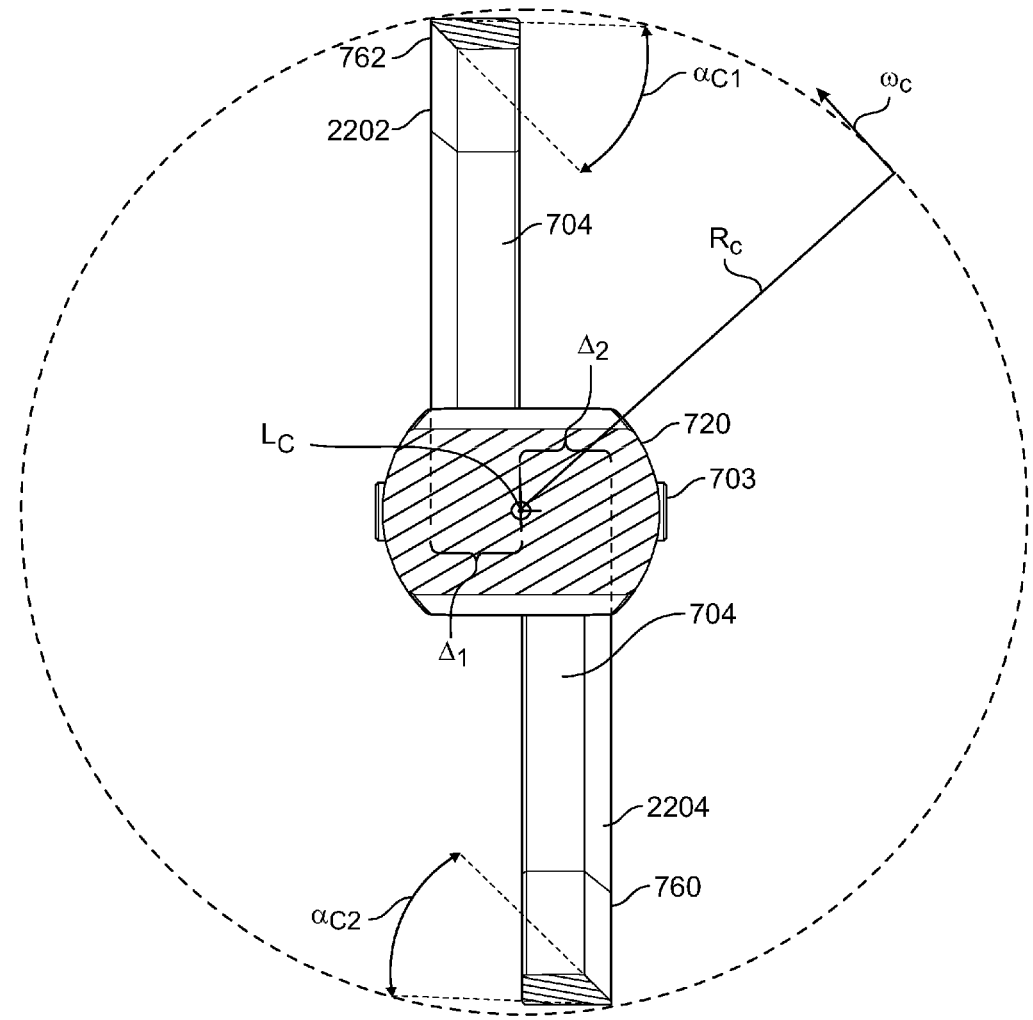
FIG. 22 shows a partial cross-sectional view, taken along lines 22-22 (shown in FIG. 21) of the apparatus shown in FIG. 21.

FIG. 22 shows broaching member 704 in partial cross section from view lines 22-22 (shown in FIG. 21). Broaching member 704 may have leading edges 2202 and 2204 that may be rotated in direction $\omega_c$ by drive shaft 730 (shown in FIG. 21). Broaching member 704 may sweep out a space in bone B (shown in FIG. 2) based on radius $R_c$, which corresponds to sections 760 and 762 (shown in FIG. 21).

Leading edge 2202 may be beveled at angle $\alpha_{c1}$. Angle $\alpha_{c1}$ may be any suitable angle, including an angle from about 5° to about 75°. Angle $\alpha_{c1}$ may cause leading edge 2202 to be generally sharp or knife-like. This may aid in the broaching member's ability to remove tissue.

Leading edge 2204 may be beveled at angle $\alpha_{c2}$. Angle $\alpha_{c2}$ may be any suitable angle, including an angle from about 5° to about 75°. Angle $\alpha_{c2}$ may cause leading edge 2204 to be generally sharp or knife-like. This may aid in the broaching member's ability to remove tissue.

As broaching member 704 is rotated clockwise generally about axis $L_c$ leading edges 2202 and 2204 may generally be the first portion of sections 760 and 762 to come in contact with tissues such as relatively less dense cancellous bone $B_{CA}$ (shown in FIG. 2). Sections 760 and 762 may be configured to be sufficiently flexible such that if either of sections 760 and 762 contacts relatively more dense materials, such as diaphysis, metaphysis and epiphysis bone, sections 760 and 762 may deflect generally radially in direction $-\omega_c$ about axis $L_c$ and/or in the linear direction towards axis $L_c$ at any location along the length of sections 760 and 762 or any other portion of broaching member 704. Deflection or deformation of sections 760 and 762 may have the affect of not disturbing the more dense tissues.

Leading edges 2202 and 2204 may be offset from axis $L_c$ by offsets $\Delta_1$ and $\Delta_2$ respectively. Appropriate magnitudes of offsets $\Delta_1$ and $\Delta_2$ may be selected. In some embodiments, offsets $\Delta_1$ and $\Delta_2$ may be constrained by the collapsed diameter (overall diameter of broach head 702 in a plane transverse to axis $L_c$ when broaching member 704 is collapsed, e.g., for deployment) of the configuration and the desired expanded engagement (radius $R_c$) of broaching member 704 with the tissue. Offsets $\Delta_1$ and $\Delta_2$ may aid in the broaching member's efficiency at displacing tissue.

Figure 22A:
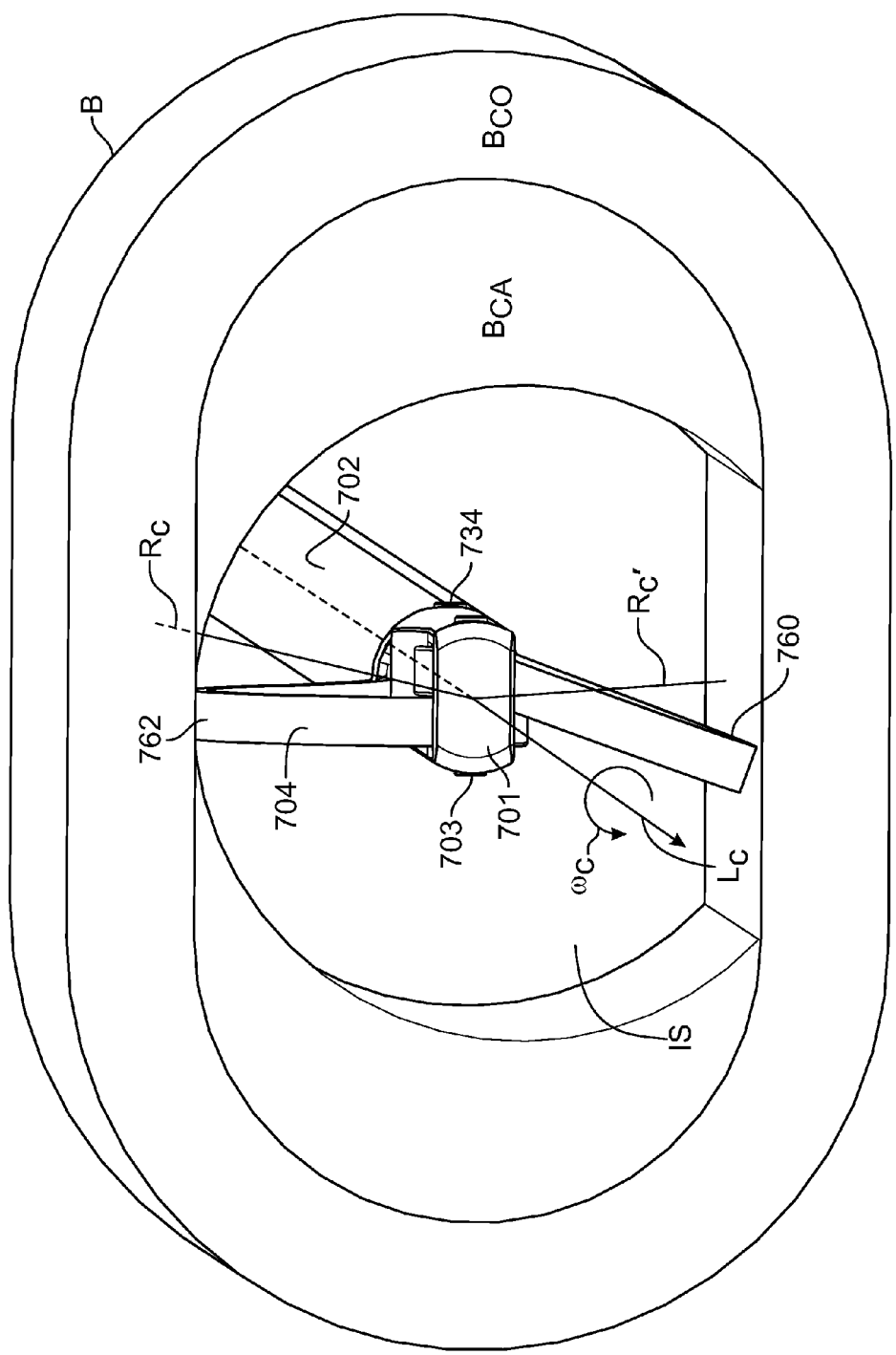
FIG. 22A shows the apparatus shown in FIG. 22 along with illustrative anatomy in connection with which the invention may be practiced.

FIG. 22A shows broach head 704 in intramedullary space IS of bone B and illustrates how flexible broaching members can broach bone of a relatively lower density and be deflected by bone of a relatively higher density. Sections 760 and 762 have displaced or removed some of cancellous bone $B_{CA}$ from bone B by rotating in direction $\omega_c$ about axis $L_c$. Sections 760 and 762 may be sufficiently stiff to remove cancellous bone to radius $R_c$ from axis Lc in the "top" portion of bone B. Because of the placement of axis L; relative to the bottom portion of bone B, sections 760 and 762 contact cortical bone $B_{CO}$ at the bottom of bone B. Sections 760 and 762 may be sufficiently flexible to be deflected by cortical bone BCO. Section 760 is shown deflected in direction $-\omega_c$ by bone BCO. Sections 760 and 762 thus remove bone only to radius $R_c'$ in the "bottom" portion of bone B.

The cavity created by broach 700 may thus be bounded in part by cancellous bone BCA and in part by cortical bone BCO. The shape of the cavity portion that is bounded by cancellous bone BCA may be governed substantially by the geometry and mechanical properties of broach 700. The shape of the cavity portion that is bounded by cortical bone BCO may be governed substantially by the native anatomy of bone B.

Figure 23:
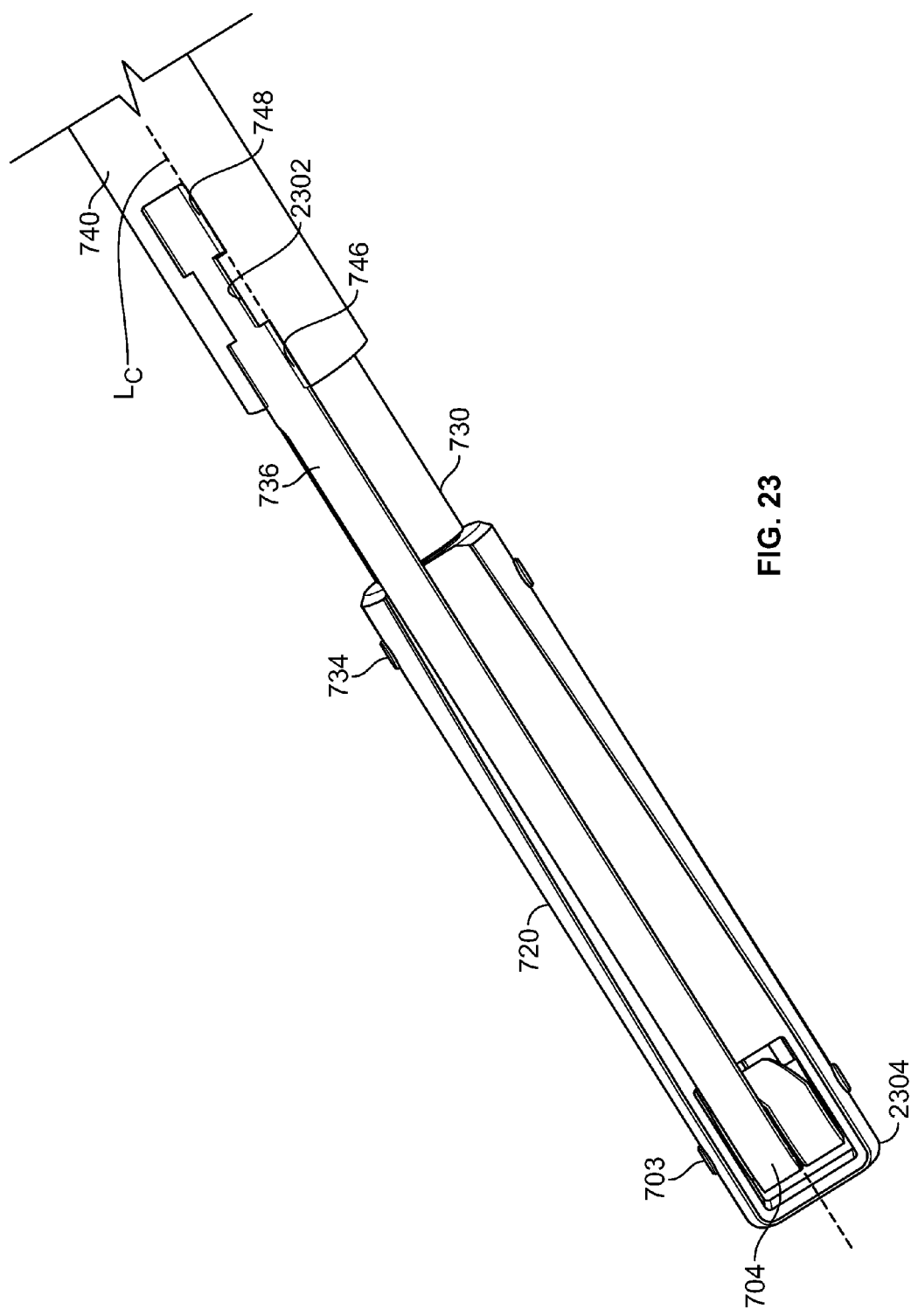
FIG. 23 shows a view, taken along lines 23-23 (shown in FIG. 20), of the apparatus shown in FIG. 20.

FIG. 23 shows a view of broach 700 along lines 23-23 (shown in FIG. 20). Broach 700 is in the contracted state. Slide cover 750 has been removed. Slots 746, 748 and 2302 in slide 740 may be configured to coincide with features on proximal end 736 (shown in FIG. 21) of broaching member 704. When proximal end 736 is engaged with slots 746, 748 and 2302, slots 746, 748 and 2302 may restrict movement of proximal end 736 in either direction generally along axis $L_c$. Slots 746, 748 and 2302 may have any suitable geometry that allows for the engagement and axial translation of proximal end 736.

Slots 746, 748 and 2302 may be of sufficient depth that, when proximal end 736 is engaged in slots 746, 748 and 2302, slide cover 750 (shown in FIG. 20) has adequate radial clearance with respect to proximal end 736 and slide 740 to slide over slide 740 and slots 746, 748 and 2302. An inner surface of slide cover 750 may prevent movement of proximal end 736 from moving in a direction generally away from axis $L_c$.

Slide 740 may include slots (not shown) that correspond to proximal end 738 (shown in FIG. 20) and have one or more features in common with, slots 746, 748 and 2302.

Broach head 720 may include broaching member wrap section 2304. Pin 703 may be integrated into wrap section 2304. Wrap section 2304 may be separate from pin 703. Wrap section 2304 may be configured to allow wrapping of broaching member 704 generally around wrap section 2304. Broaching member 704 may be looped in wrap section 2304. Broaching member 704 may be wrapped (as shown in FIG. 23) at least one full turn in wrap section 2304. Wrapping about wrap section 2304 may bias segments 760 and 762 (shown in FIG. 21) away from axis $L_c$.

Figure 24:
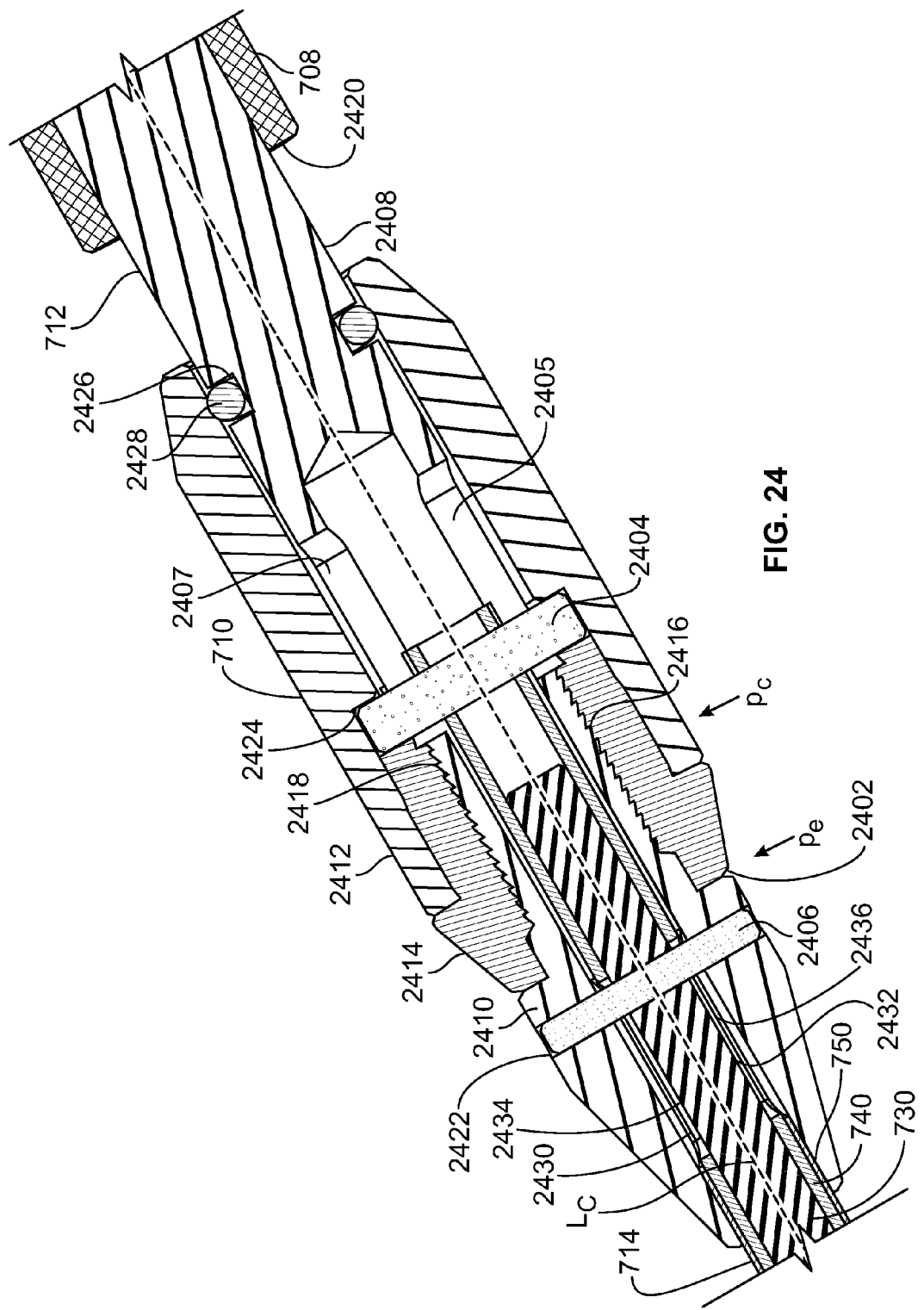
FIG. 24 shows a partial cross-sectional view, taken along lines 24-24 (shown in FIG. 8) of the apparatus shown in FIG. 8.

FIG. 24 shows a cross section, viewed along lines 24-24 (shown in FIG. 8) of a portion of broach control 706 (shown in FIG. 7). Expansion control hub 710 is shown with base 2402 at position $p_e$. This may correspond to the expanded state of broaching member 704, as shown in FIG. 8. Base 2402 may be moved distally to position $p_c$. This may correspond to the contracted state of broaching member 704, as shown in FIG. 7. Expansion control hub 710 may operate in connection with body 2408. Body 2408 may include control shaft 712 and distal stop 2410. Control shaft 712 may include threads 2418.

Expansion control hub 710 may include outer member 2412 and inner member 2414. Outer member 2412 and inner member 2414 may be fixed to each other. Slide pin 2404 may be captured between outer member 2412 and inner member 2414. Inner member 2414 may include threads 2416 for engagement with threads 2418 on control shaft 712. Slide pin 2404 may travel in slots 2405 and 2407 in body 2408.

Expansion control hub 710 may be moved along axis $L_c$ by applying force to expansion control hub 710. In some embodiments, expansion control hub 710 may be advanced axial generally along axis $L_c$ by applying rotational force generally about axis $L_c$ to expansion control hub 710 such that threads 2416 move advance or retreat through threads 2418.

Axial movement of expansion control hub 710 relative to body 2408 may be transferred to slide 740 and slide cover 750 while drive shaft 730 remains axially fixed to body 2408 by pin 2406. Slide 740 may include cut-outs 2430 and 2432. Slide cover 750 may include cut-outs 2434 and 2436. Cut-outs 2430, 2432, 2434 and 2436 may provide clearance of pin 2406 when slide 740 and slide cover 750 travel axially.

When expansion control hub 710 is moved axially, proximal ends 736 and 738 (shown in FIG. 20) of broaching member 704 thus move axially. Distal end 780 (shown in FIG. 7) of broaching member 704 may be axially fixed to drive shaft 730, which may be fixed to body 2408. Thus, when expansion control hub 710 moves distally, the distance between (a) proximal ends 736 and 738 and; (b) distal end 780 decreases and broaching member 704 expands. When expansion control hub 710 moves proximally, the distance between (a) proximal ends 736 and 738; and (b) distal end 780 increases and broaching member 704 contracts.

Distal stop 2410 and proximal stop 2420 may limit axial movement of expansion control hub 710. Although proximal stop 2420 is shown as being part of handle 708, proximal stop 2420 may be separate from handle 708.

Handle 708 may transfer rotational motion generally about axis $L_c$ to control shaft 712. Control shaft 712 may transfer the rotation to slide pin 2404 and drive shaft pin 2406. Slide pin 2404 may transfer the rotation to slide 740 and slide cover 750. Drive shaft pin 2406 may transfer the rotation to drive shaft 730, which may drive broaching member 704 (shown in FIG. 21).

Distal stop 2410 is shown as being integral with body 2408, but distal stop may be a separate element that is attached to control shaft 712 or a different part of body 2408.

Pin 2406 may extend into recess feature 2422. Recess feature 2422 may be a through-hole. Pin 2406 may extend through the through hole to a location external to body 2408.

Pin 2404 may extend into recess feature 2424. Recess feature 2424 may be a through-hole. Pin 2404 may extend through the through-hole to a location external to body outer member 2412. Recess feature may extend circumferentially about axis $L_c$. If recess feature 2424 extends circumferentially about axis $L_c$, expansion control hub 710 may rotate about axis $L_c$ substantially without restricting, or being restricted by, pin 2404.

Body 2408 may include circumferential recess 2426. Recess 2426 may be sized to engage O-ring 2428. Recess 2426 may prevent axial movement between body 2408 and O-ring 2428 generally along axis $L_c$. O-ring 2428 may be sized to provide an interference fit with outer member 2412. The interference fit may produce friction between O-ring 2428 and expansion control hub 710. The friction may allow expansion control hub 710 to be lightly locked at any rotational position relative to body 2408, generally about axis $L_c$.

Figure 25:
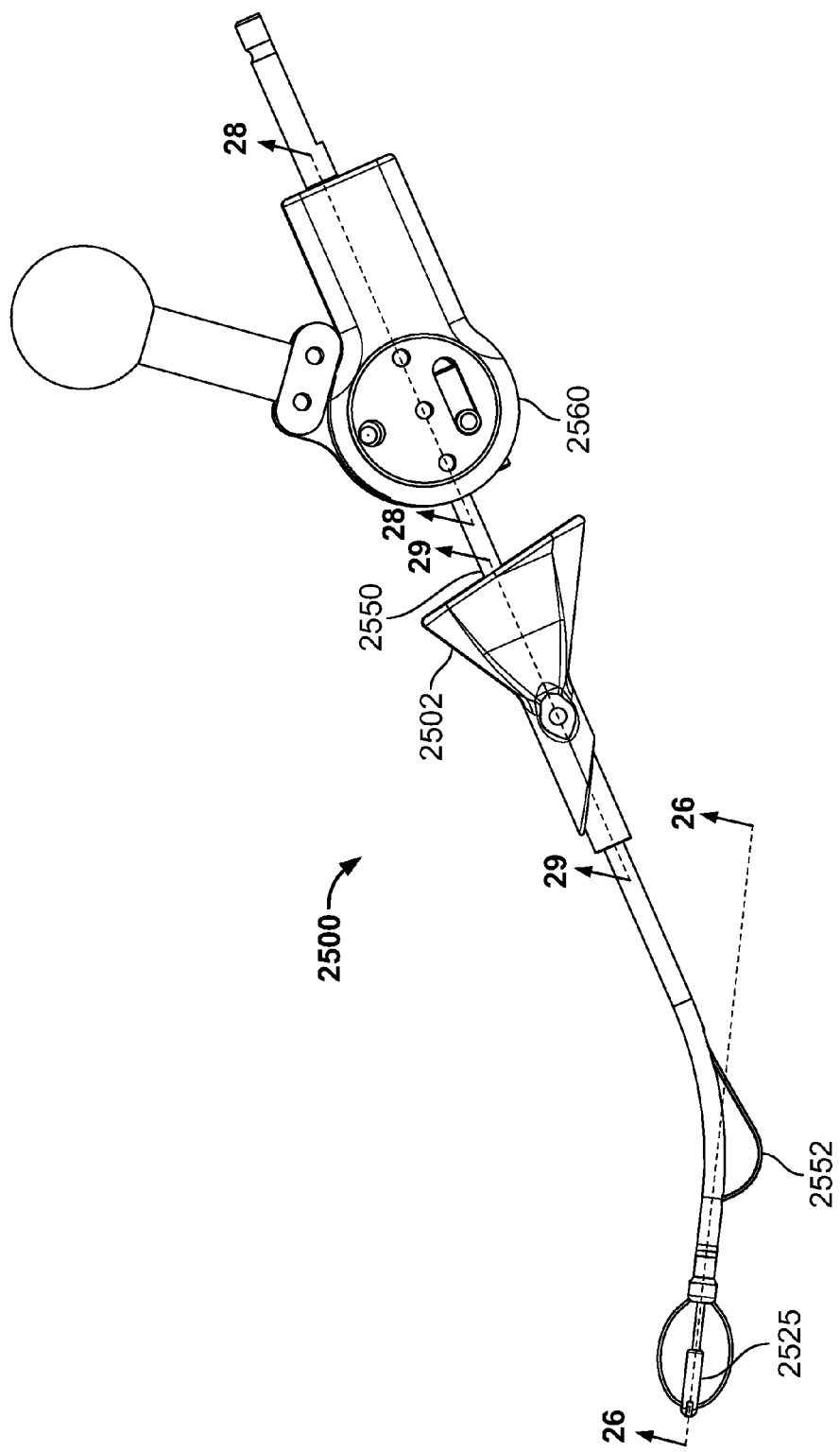
FIG. 25 shows a portion of the apparatus shown in FIG. 9, along with other apparatus.

FIG. 25 shows illustrative cavity preparation apparatus 2500. Apparatus 2500 may include broach 2550. Broach 2550 may have one or more features in common with broach 950 (shown in FIG. 9). Broach 2550 may include one or more of broach head 2525, elevator ribbon 2552 and control body 2560. Apparatus 2500 may include guide 2502. Guide 2502 may guide broach 2550 or any other suitable apparatus through an access hole such as H or I (shown in FIG. 2). Guide 2502 may retain soft tissue at a distance from the access hole to prevent engagement of the soft tissue by an instrument that is present in guide 2502.

FIGS. 26-29 show features of different portions of apparatus 2500.

Figure 26:
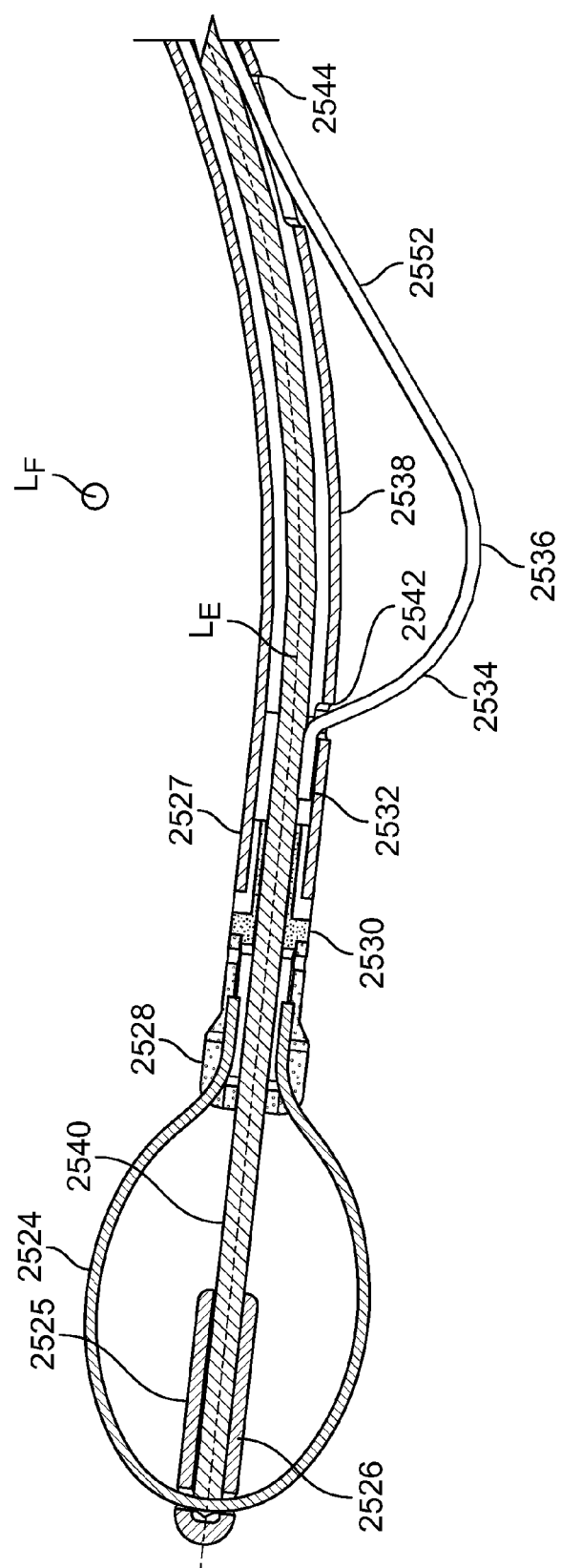
FIG. 26 shows a partial cross-sectional view, taken along lines 26-26 (shown in FIG. 25), of apparatus shown in FIG. 25.

FIG. 26 shows in partial cross section illustrative broach head 2525 and illustrative elevator ribbon 2552.

Broach head 2525 may be driven about axis LE by rotating drive shaft 2540. Broach head 2525 may include broaching member 2524, which may have one or more features in common with broaching member 704 (shown in FIG. 7). Broach head 2525 may include distal hub 2526 and proximal hub 2528. One or both of distal hub 2526 and proximal hub 2528 may transfer rotation to broaching member 2524. One or both of distal hub 2526 and proximal hub 2528 may support broaching member 2524.

Drive shaft 2540 may extend within broach sheath 2527. Drive shaft 2540 may be supported in rotation by bushing 2530 at the end of broach sheath 2527.

Illustrative elevator ribbon 2552 may be anchored to broach sheath 2527 at fixation 2532. When axial compressive force, generally along axis LE, is applied to elevator ribbon 2552, elevator ribbon 2552 may buckle along its length. For example, elevator ribbon 2552 may buckle at or near section 2534. Section 2536 may be used to support broach sheath 2527 at an elevation relative to cancellous bone $B_{CA}$ or cortical bone $B_{CO}$ in bone B (shown in FIG. 2).

Portions of elevator ribbon 2552 may extend inside broach sheath 2527 and pass through slots 2542 and 2544 to section 2534. In some embodiments, there may be contact between drive shaft 2540 and elevator ribbon 2552. In some embodiments, there may be no contact between drive shaft 2540 and elevator ribbon 2552.

Elevator ribbon 2552, when compressed, may apply tension to adjacent portion 2538 of broach sheath 2527 and compression to opposite portion 2540 of broach sheath 2527. One or both of the tension of adjacent portion 2538 and the compression of opposite portion 2540 may cause broach sheath 2527 to curve generally about an axis such as $L_F$.

One or both of adjacent portion 2538 and opposite portion 2540 may include stress-relief features that allow bending under tension and compression. The stress-relief features may include slots or slot patterns. The stress-relief features may be provided using laser-cutting. The stress-relief may provide an equilibrium curvature such that broach sheath 2527 is curved at rest.

The stress-relief features may include sintered particles. The particles may include metal, polymer, composite or any other suitable material.

Figure 27:
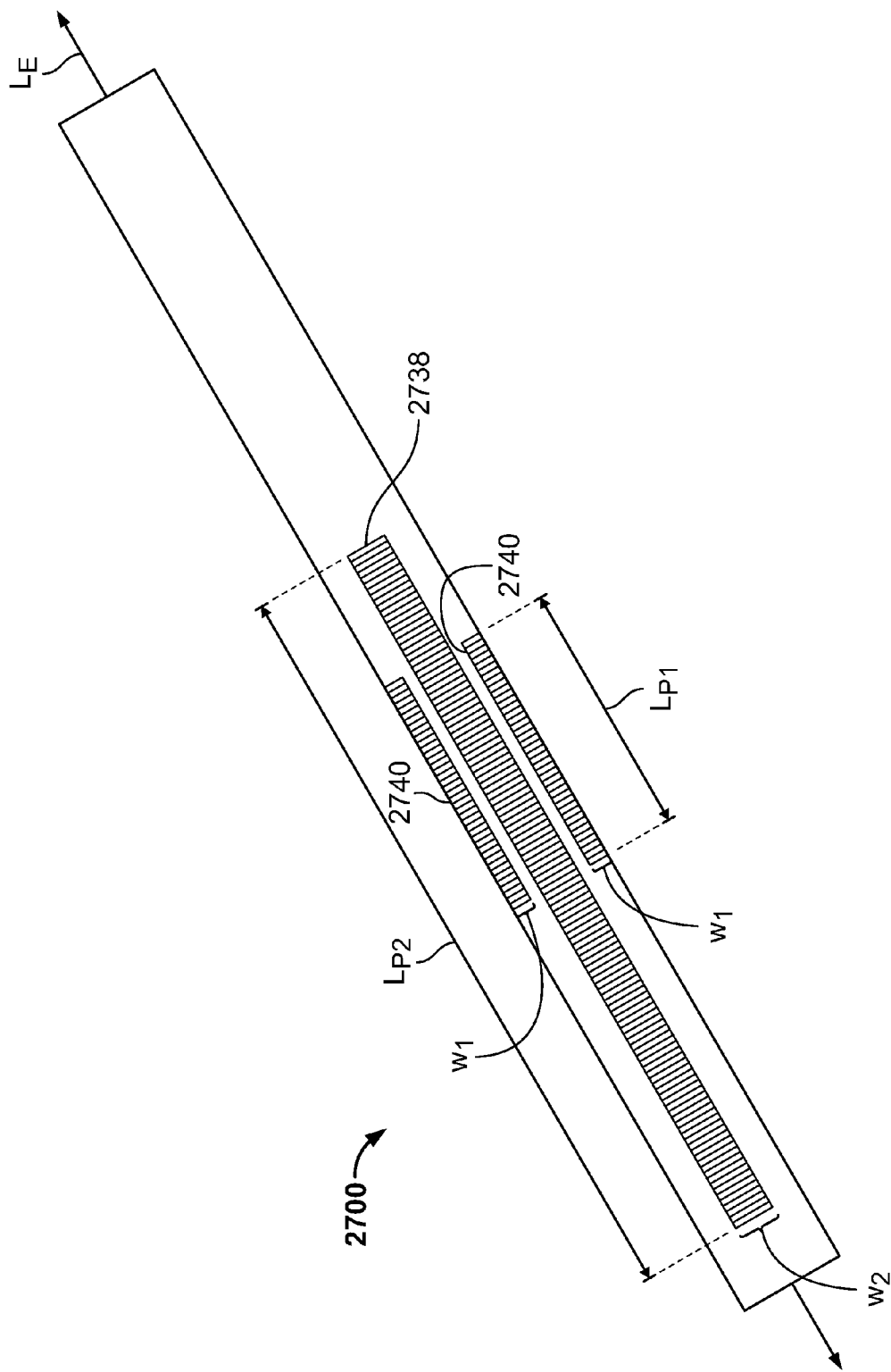
FIG. 27 shows information that may be used to manufacture apparatus in accordance with the principles of the invention.

FIG. 27 shows illustrative laser-cut pattern 2700 for a broach sheath such as 927 (shown in FIG. 9) or 2527 (shown in FIG. 26). Pattern 2700, which is shown flat for illustration, may be cut in a cylindrical tube to relieve compression on one side of the tube and relieve tension on the other side of the tube. For example, compression relief pattern 2740 may be provided along opposite portion 2540 of broach sheath 2527. Tension relief pattern 2738 may be provided along adjacent portion 2538 of broach sheath 2527. Tension and compression relief may be increased by lengthening lengths $L_{p1}$ and $L_{p2}$, respectively. Bending stiffness may be reduced by increasing pattern widths $w_1$ and $w_2$. Increasing kerf and decreasing inter-cut spacing may also decrease bending stiffness. In some embodiments, the tube may have an outer diameter of 0.108 in. In some embodiments, the tube may have an outer diameter of 0.125 in. Any suitable outer diameter may be used.

Figure 28:
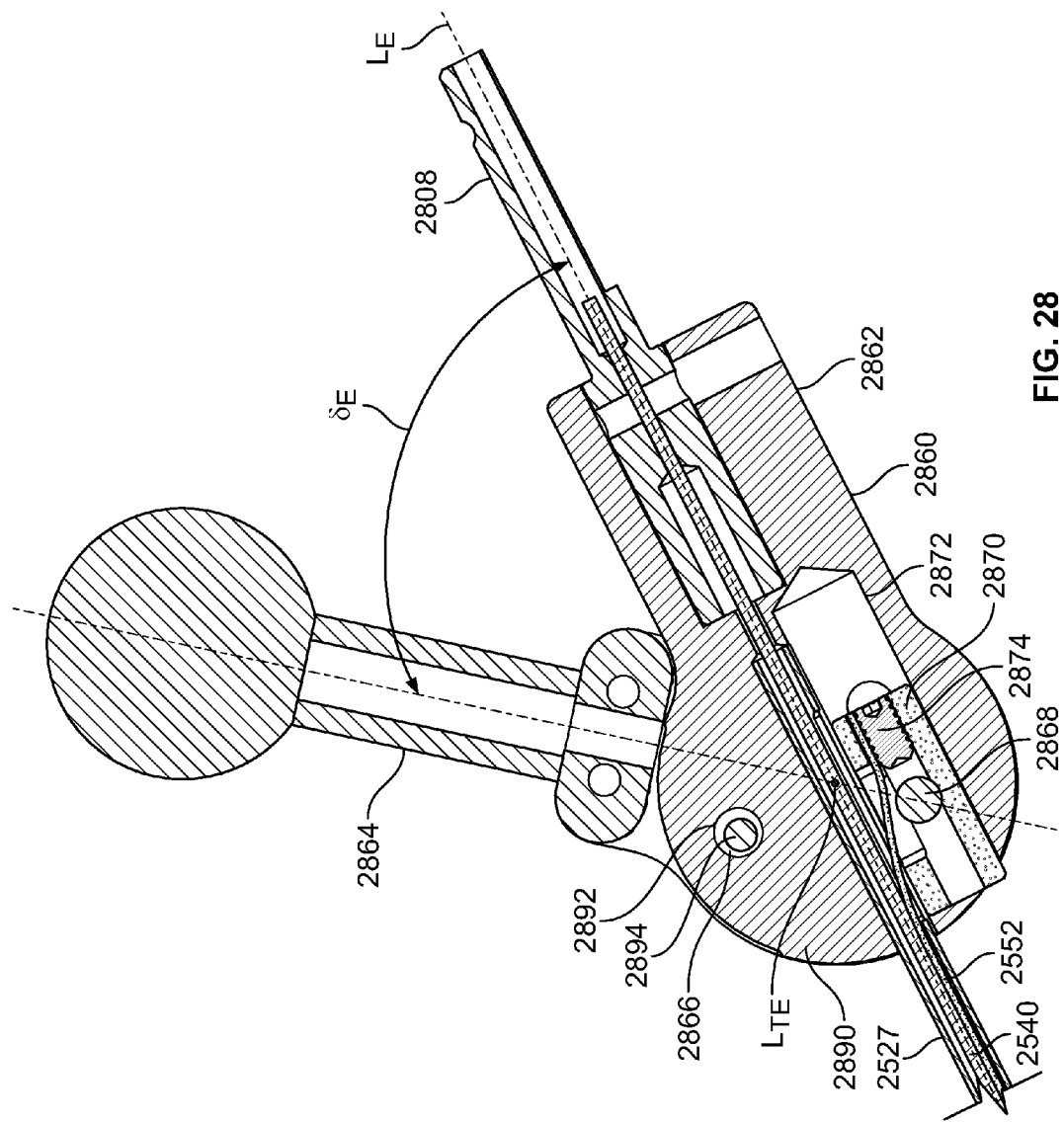
FIG. 28 shows a partial cross-sectional view, taken along lines 28-28 (shown in FIG. 25), of apparatus shown in FIG. 25.

FIG. 28 shows illustrative elevator control body 2860. Elevator control body 2860 may support the proximal end of broach sheath 2527. Drive shaft 2540 may extend through control body 2860 to torque adapter 2808. Torque adapter 2808 may be cannulated. Torque adapter 2808 may be a cannulated A-O type adapter. Torque adapter 2808 may have a "D"-shaped extension for engagement by a D-shaped chuck.

Torque adapter 2808 may be torqued by any suitable source of rotational energy.

Control body 2860 may include housing 2862 and actuator 2866. Handle 2864 may be used to rotate actuator 2866 through angle $\delta_E$ about axis LTE relative to housing 2862. When actuator moves through angle $\delta_E$, shaft 2868 may drive shuttle 2870 in slot 2872. The distal end of elevator ribbon 2552 may be fixed to the shuttle, for example, by screw 2874. When the shuttle is in a distal position, elevator ribbon 2552 is expanded (as shown in FIG. 26). When the shuttle is in a proximal position, elevator ribbon 2552 is contracted toward axis LE.

Actuator 2866 may include face member 2890. Face member 2890 may be fixed relative to housing 2862. Face member 2890 may include recess 2892. Recess 2892 may "catch" a projection such as 2894 to act as a detent. Projection 2894 may be one of several projections that provide detent positions. For example, three detent positions may be provided: forward, neutral and back. In the forward position, elevator ribbon 2552 is extended. In the back position, elevator ribbon 2552 is compressed. In the neutral position, elevator ribbon 2552 is in a partially compressed state.

Housing 2862 may be configured to house a torque limiter (not shown). The torque limiter may couple torque adapter 2808 to drive shaft 2540 and may be used to limit the torque that is applied to broach head 2525 (shown in FIG. 25). If broach head 2525 were to jam in bone B (shown in FIG. 2), the torque limiter may cap or reduce the torque on broaching head 2525 to prevent damage to broaching head 2525, other elements of apparatus 2500, other involved apparatus or bone B.

Figure 29:
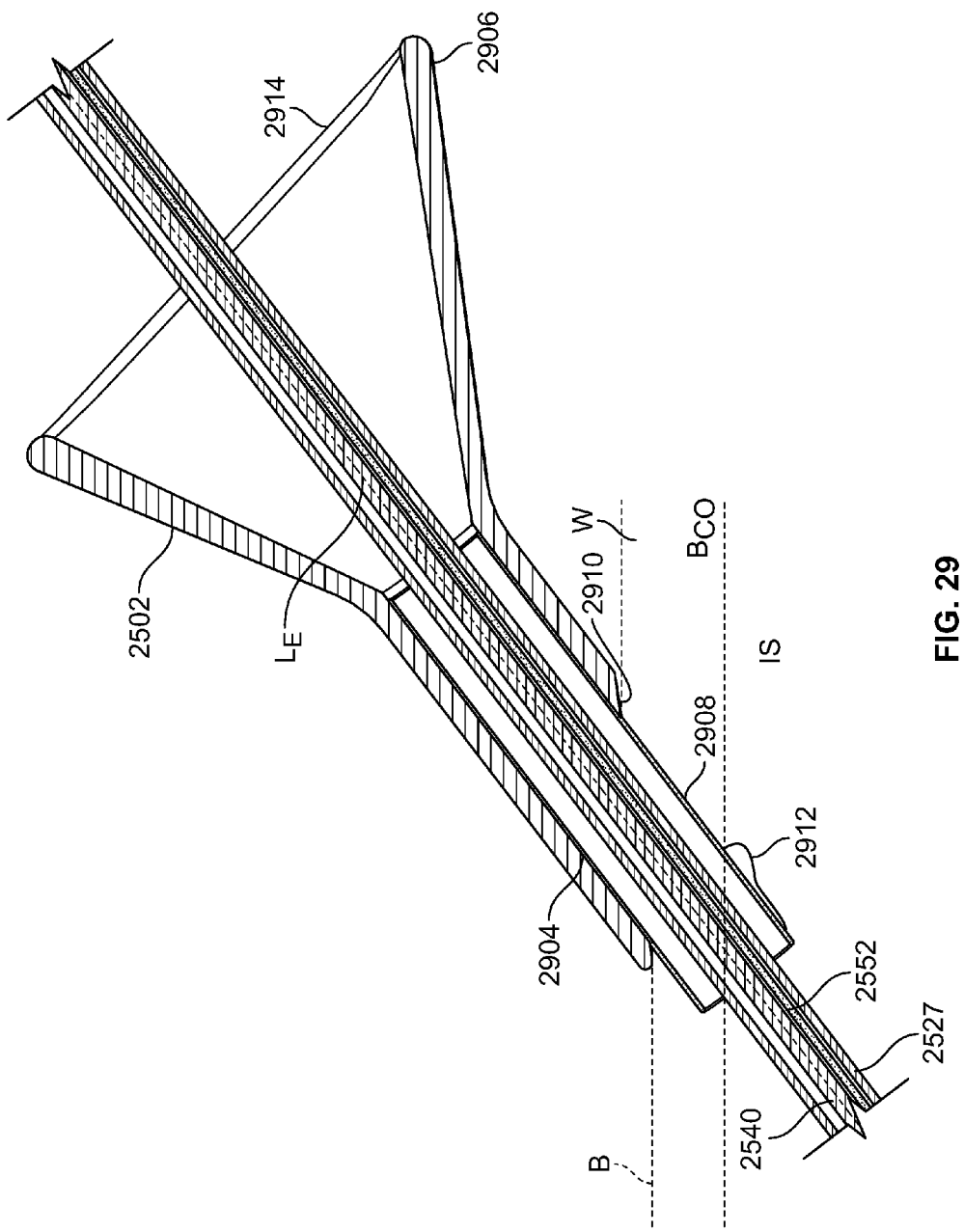
FIG. 29 shows a partial cross-sectional view, taken along lines 29-29 (shown in FIG. 25), of apparatus shown in FIG. 25.

FIG. 29 shows illustrative guide 2502. Guide 2502 may include cannula 2904 and funnel 2906. Funnel 2906 may facilitate insertion of a broach head such as 2525 (shown in FIG. 25) into a hole such as H (shown in FIG. 2).

Guide 2502 may be "preloaded" on broach sheath 2527. A practitioner may insert a broach head into hole H (shown in FIG. 2) and then position guide 2520 in hole H. Funnel 2906 may protect soft tissue outside bone B. Cannula 2904 may guide the broach head through hole H when broach head is withdrawn from hole H (for example, at the conclusion of a cavity preparation procedure).

Outer wall 2908 of cannula 2904 may be of an appropriate diameter to substantially fill hole H. Funnel 2906 may include ledge 2910. Ledge 2910 may limit the extent to which cannula 2904 may extend into intramedullary space IS.

Cannula 2904 may support detent 2912. Detent 2912 may be present to catch on the inside of cortical bone $B_{CO}$ wall W to retain cannula 2904 in position in hole H. Detent 2912 may be have a tapered profile so that it can engage walls W of different thickness. In some embodiments, detent 2912 may be passive. In passive embodiments, detent 2912 may be resilient, biased or rigid. In some embodiments, detent 2912 may be active. In active embodiments, detent 2912 may be actuated. For example, detent 2912 may be actuated by a manual control that causes detent 2912 to extend away from tube cannula 2904 a desired distance or a preset distance. Cannula 2904 may include more than one detent.

Mouth 2914 of funnel 2906 may have any suitable shape transverse to axis LE. The shape may be rectangular, triangular, elliptical, tear-drop, splayed, circular and any other suitable shape.

Funnel 2906 may include a skiving-curved section (not shown). The skiving-curved section may be at the distal end of funnel 2906.

Guides for rotatable broaches may include a body that has a cannula. The body may support a broach sheath in alignment with the cannula. A drive shaft may pass through the cannula and extend distally through the broach sheath. A rotation source may be connected to the drive shaft proximal the body. The body may be hand-held. The body may have no adaptations to mate with a hole such as H (shown in FIG. 2).

Figure 30:
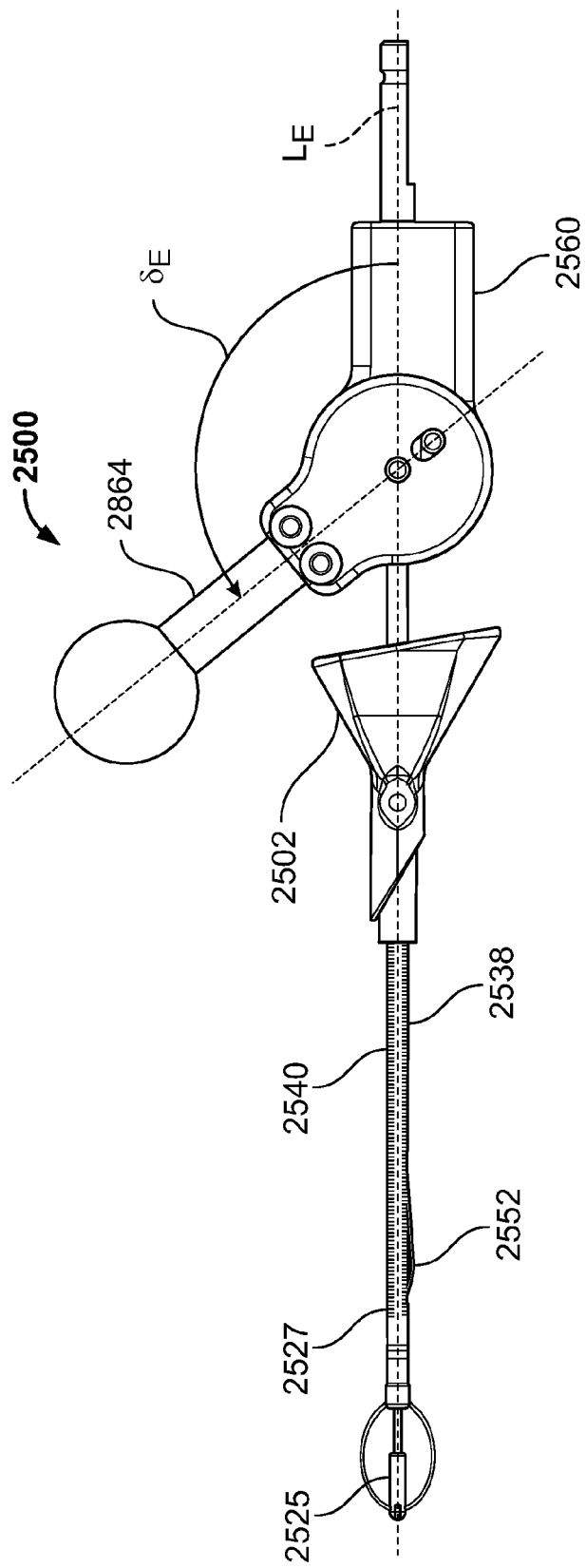
FIG. 30 shows apparatus shown in FIG. 25 in a state that is different from the state shown in FIG. 25.

FIG. 30 shows apparatus 2500 (shown in FIG. 25) with control 2864 at a larger angle $\delta_E$ and elevator ribbon 2552 in the contracted state close to broach sheath 2527. Stress-relief features such as those shown in flat model 2700 (shown in FIG. 27) are shown in portions 2538 and 2540 of broach sheath 2527.

Figure 31:
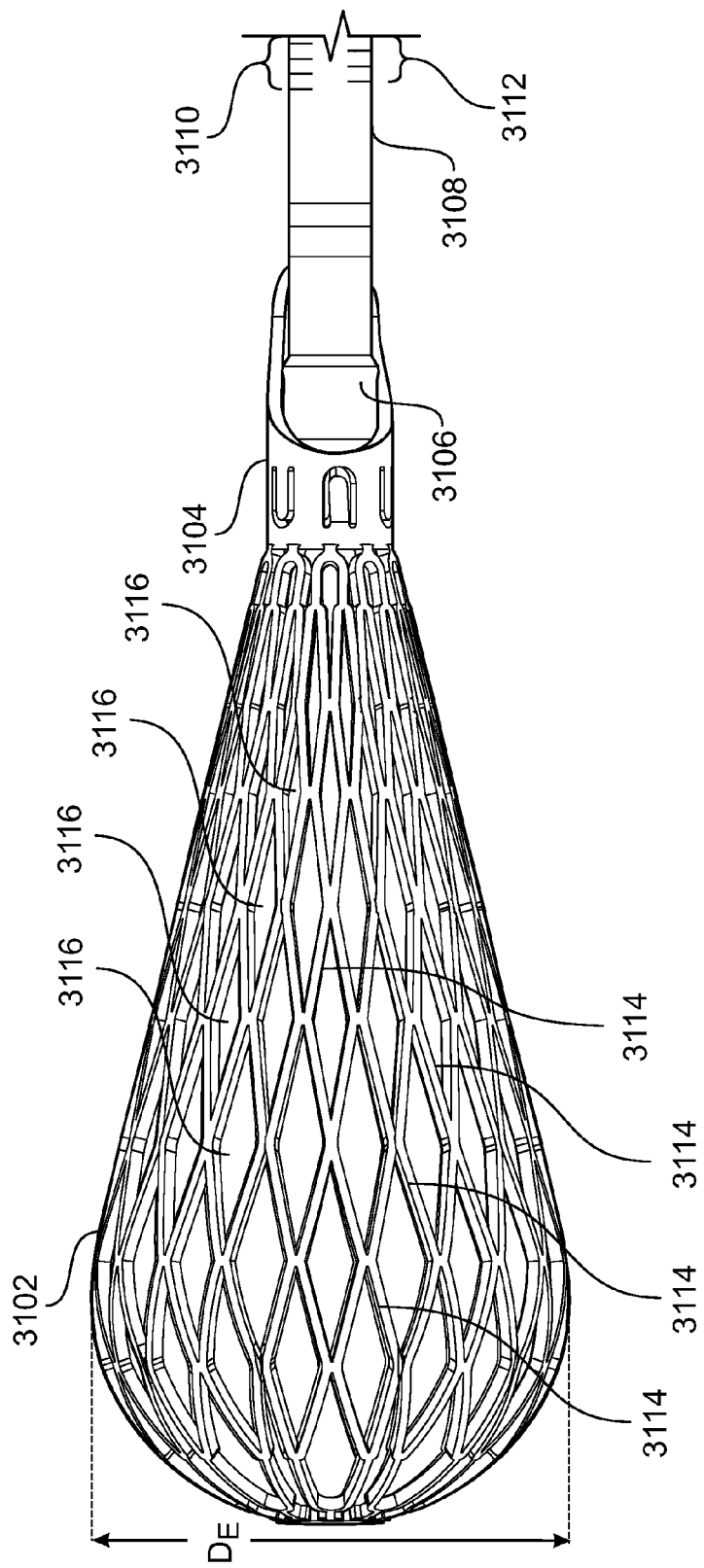
FIG. 31 shows still other apparatus in accordance with the principles of the invention.

FIG. 31 shows illustrative broaching member 3102. Broaching member 3102 may be mounted by fixture 3104 to hub 3106 at the distal end of a broach shaft 3108. Broach shaft 3108 may have one or more features in common with broach shaft 2527 (shown in FIG. 26) or any other broach shaft discussed or shown herein. For example, broach shaft 3108 may include stress-relief features 3110 and 3112.

Hub 3106 may have one or more features in common with hub 2528 (shown in FIG. 26).

Broaching member 3102 may be a self expanding structure. Broaching member 3102 may be constructed from laser-cut tube stock that is expanded into a suitable shape, such as that shown. Broaching member 3102 may include broaching members such as 3114. Broaching member 3102 may include numerous interconnected cells such as cell 3116. The cells may be defined by one or more broaching members. Some cells may be defined by structures other than broaching members. The cells may be arranged in a network. The cells may be linked such that when the structure is stressed (e.g., compressed) at a point the stress is distributed to nearby cells. Broaching member 3102 may thus rotate in a bone cavity that has an irregular shape, for example, nonround, oblong, or angular. The cavity may be smaller than a diameter of broaching member 3102, such as expanded diameter $D_E$.

Broaching member 3102 may include broaching members that included braided wire (not shown). Broaching member 3102 may include broaching members that included braided ribbon (not shown).

In some embodiments, each cell arm may be a broaching member. When a large number (i.e., when the circumferential density of broaching members is high) of broaching members are present during the rotation of a broaching head, a relatively lower torque is required to drive the broaching head.

Figure 32:
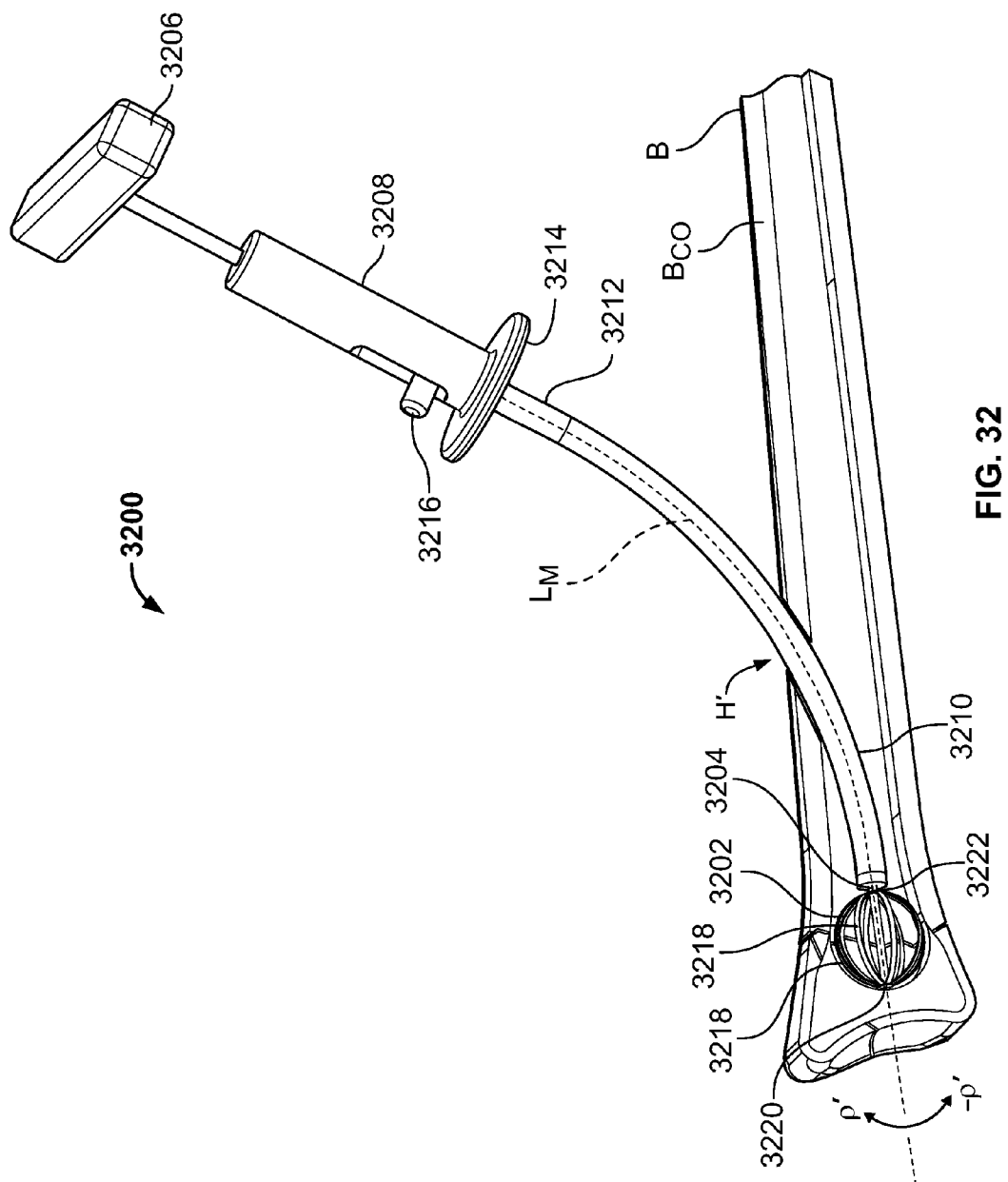
FIG. 32 shows yet other apparatus in accordance with the principles of the invention.

FIG. 32 shows illustrative broach 3200 inserted in bone B. Broach 3200 may include broaching head 3202. Flexible rotating drive shaft 3204 may drive broaching head 3202 in rotation in directions ρ' or −ρ'. Drive shaft 3204 may be driven by a rotation source such as handle 3206. In some embodiments, the rotation source may include a surgical hand drill, a dremel motor or any other suitable rotational power source.

Drive shaft 3204 may be sheathed in a flexible cannula (apart from broach sheath 3210, which is described below).

Control body 3208 may be used to insert broaching head 3202 through a hole at site H'. During insertion, broaching head 3202 may be withdrawn into flexible broach sheath 3210. Proximal end 3212 of flexible broach sheath 3210 may be fixed to distal end 3214 of control body 3208. Actuator 3216 may engage drive shaft 3204 and may slide relative to control body 3208. Actuator 3216 may thus translate drive shaft 3204 along axis LM within guide sheath 3210.

In some embodiments, broaching head 3202 may be compressible and expandable. Broaching head 3202 may be compressed within guide sheath 3210. Broaching head 3202 may be expanded outside of guide sheath 3210. In some embodiments, broaching head 3202 may self-expand in bone B after being pushed out of guide sheath 3210 by drive shaft 3204. In some embodiments, broaching head 3202 may be outside guide sheath 3210 when broaching head 3202 is delivered into bone B.

Broaching head 3202 may include one or more broaching members 3218 that have sufficient rigidity to displace cancellous bone, but sufficient resilience to deform when brought into contact with cortical bone and thus leave the cortical bone substantially in place.

Broaching members 3218 may be formed from loops. The loops may be fixed to distal hub 3220. The loops may be fixed to proximal hub 3222. One or both of distal hub 3220 and proximal hub 3222 maybe axially fixed to drive shaft 3204. One or both of distal hub 3220 and proximal hub 3222 maybe rotationally fixed to drive shaft 3204. Broaching head 3202 may include any suitable number of loops. Broaching members 3218 may have one or more features in common with broaching member 704 (shown in FIG. 7) or any other broaching member described or shown herein.

Figure 33:
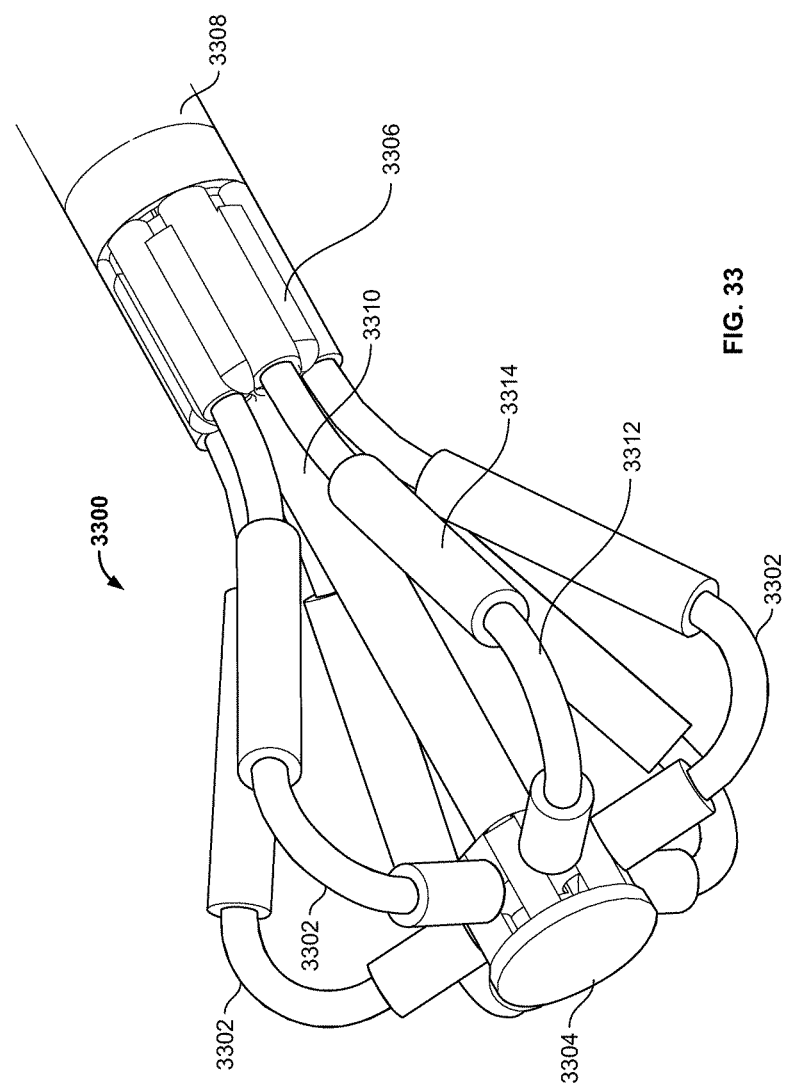
FIG. 33 shows yet other apparatus in accordance with the principles of the invention.

FIG. 33 shows illustrative broaching head 3300. Broaching head 3300 may include broaching members 3302. Each of broaching members 3302 may have one or more features in common with broaching member 704 (shown in FIG. 7) or any other broaching member shown or described herein. Broaching head 3300 may have any suitable number of broaching members 3302. For example, broaching head 3300 may have one broaching member, 2-6 broaching members, 7-20 broaching members, more than 20 broaching members or any suitable number of broaching members.

Broaching head 3300 may be contracted toward drive shaft 3310 and withdrawn into an outer sheath (not shown). The outer sheath may be inserted in a hole such as H (shown in FIG. 2). Broaching head 3300 may then be deployed by retracting the sheath. Broaching members 3302 may be sufficiently resilient to be contracted and may expand away from drive shaft 3310 when the sheath is retracted.

Broaching members 3302 may be supported by distal hub 3304. Distal hub 3304 may be absent and broaching members 3302 may have free distal ends. Broaching members with free distal ends may be supported at their proximal ends near the central axis of broaching head 3300. The broaching members may be angled radially away from the central axis of broaching head 3300.

Broaching members with free distal ends may have suitable shape at the distal ends, such as pointed, forked, rounded, blunt or truncated.

Broaching members 3302 may be supported by proximal hub 3306. Proximal hub 3306 may be supported by broach sheath 3308. Broach sheath 3308 may have one or more features in common with broach sheath 127 (shown in FIG. 1).

Drive shaft 3310 may drive broaching head 3300 in rotation. Drive shaft 3310 may extend distally to distal hub 3304. Drive shaft 3310 may extend through broach sheath 3308 to a proximal rotation source (not shown).

One or both of distal hub 3304 and proximal hub 3306 maybe axially fixed to drive shaft 3310. One or both of distal hub 3304 and proximal hub 3306 maybe rotationally fixed to drive shaft 3310.

One or more of broaching members 3302 may include a hoop segment such as 3312. Segment 3312 may support one or more reinforcements such as 3314.

Segment 3312 may be rigid. Segment 3312 may be resilient. Segment 3312 may have any suitable pre-set curvature or be substantially linear. Segment 3312 may be a closed loop. The loop may be asymmetric.

Segment 3312 may include a length of wire, ribbon, cable, stranded wire, or any other suitable form or structure. Segment 3312 may include polymer, metal, alloy or any other suitable material. Segment 3312 may be constructed of a mesh cut from metal tube.

Reinforcement 3314 may be a tube. Reinforcement 3314 may be formed from polymer, metal, alloy or any other suitable material. One or more reinforcements such as 3314 may be sized and positioned to support segment 3312 in a desired contour. One or more reinforcements such as 3314 may provide bone-broaching abrasiveness, momentum or both.

Figure 34:
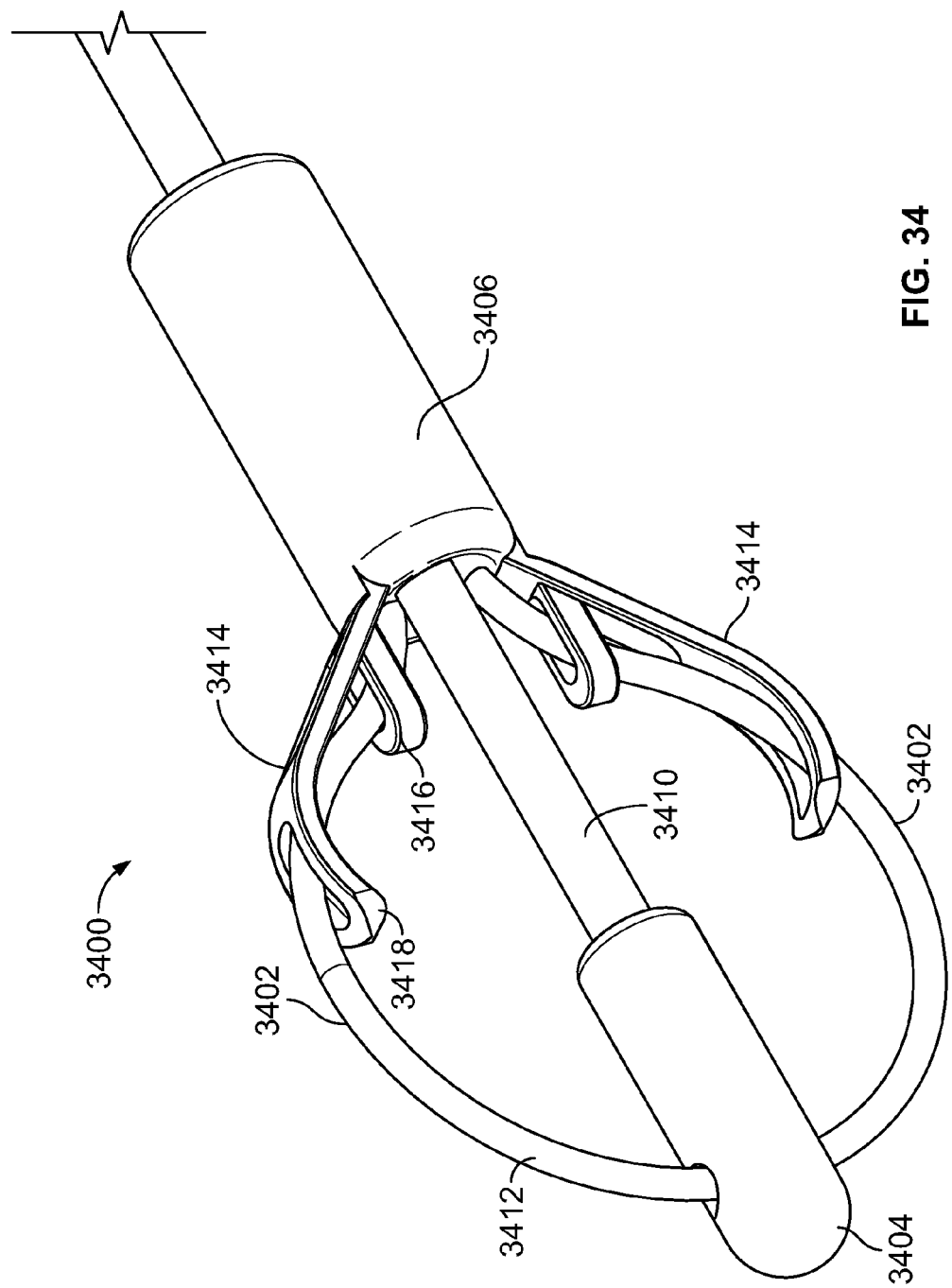
FIG. 34 shows yet other apparatus in accordance with the principles of the invention.

FIG. 34 shows illustrative broaching head 3400. Broaching head 3400 may include broaching members 3402. Each of broaching members 3402 may have one or more features in common with broaching member 704 (shown in FIG. 7) or any other broaching member shown or described herein. Broaching head 3400 may have any suitable number of broaching members 3402. For example, broaching head 3400 may have one broaching member, 2-6 broaching members, 7-20 broaching members, more than 20 broaching members or any suitable number of broaching members.

Broaching members 3402 may be supported by distal hub 3404. Broaching members 3402 may be supported by proximal hub 3406. Proximal hub 3406 may be supported by drive shaft 3410. Drive shaft 3410 may have one or more features in common with drive shaft 730 (shown in FIG. 20) or any other drive shaft that is shown or described herein.

Drive shaft 3410 may drive broaching head 3400 in rotation. Drive shaft 3410 may extend distally to distal hub 3404. Drive shaft 3410 may extend to a proximal rotation source (not shown).

One or both of distal hub 3404 and proximal hub 3406 maybe axially fixed to drive shaft 3410. One or both of distal hub 3404 and proximal hub 3406 maybe rotationally fixed to drive shaft 3410.

One or more of broaching members 3402 may include a hoop segment such as 3412. Reinforcement 3414 may support one or more segments such as 3412.

Segment 3412 may be rigid. Segment 3412 may be resilient. Segment 3412 may include a length of wire, ribbon, cable, stranded wire or any other suitable form or structure. Segment 3412 may include polymer, metal, alloy or any other suitable material.

Reinforcement 3414 may be a brace. Reinforcement 3414 may be formed from polymer, metal, alloy or any other suitable material. One or more reinforcements such as 3414 may be sized and positioned to support segment 3412 in a desired contour. One or more reinforcements such as 3414 may provide bone-broaching abrasiveness, momentum or both.

The brace may reduce material fatigue in segment 3412. The brace may help segment 3412 retain its shape under forces of rotation and broaching resistance. The brace may include loops such as 3418 and 3416. The loops may pass around the circumference of segment 3412. In some embodiments, loops 3418 and 3416 may encompass only a portion of the circumference. In some embodiments, the brace may be fixed to segment 3412, for example, by crimping, welding or press-fit.

The brace may support broaching edges for displacing bone material in bone B (shown in FIG. 2). The broaching edges may have any suitable form, such as serrated, sawtooth, knife-edge, rectilinear edge or any other suitable form.

The brace may be formed from a pattern that is cut into a metal tube.

Figure 35:
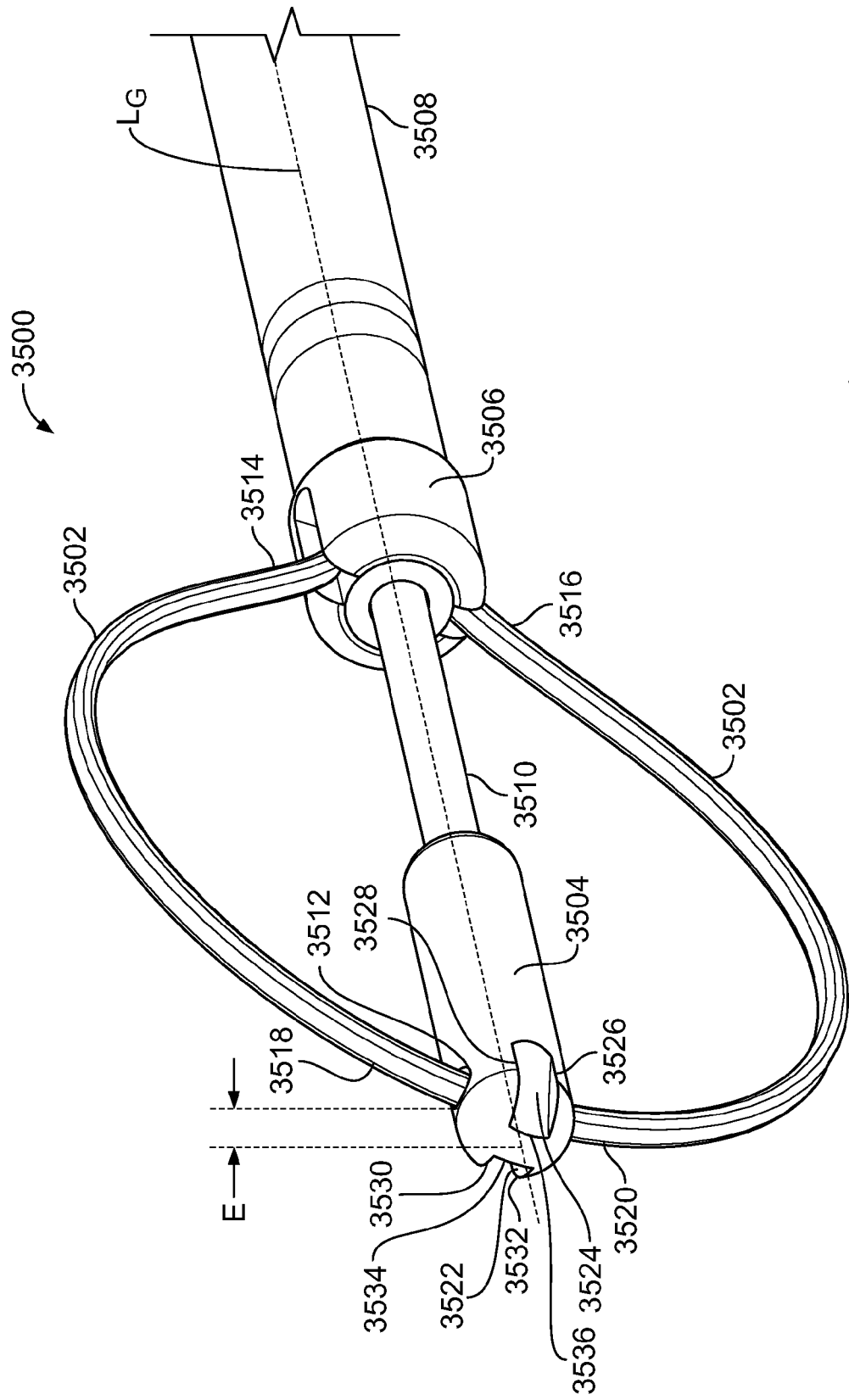
FIG. 35 shows yet other apparatus in accordance with the principles of the invention.

FIG. 35 shows illustrative broaching head 3500. Broaching head 3500 may include broaching member 3502. Broaching member 3502 may have one or more features in common with broaching member 704 (shown in FIG. 7) or any other broaching member shown or described herein.

Broaching head 3500 may have any suitable number of broaching members such as broaching member 3502. For example, broaching head 3400 may have one broaching member, 2-6 broaching members, 7-20 broaching members, more than 20 broaching members or any suitable number of broaching members. When more than one broaching member is included, the broaching members may have different sizes or other features.

Broaching member 3502 is illustrated as a single solid hoop. Broaching member 3502 may include one or more members that are stranded or braided. Broaching member 3502 may include wire, strip stock, sheet stock, strand, ribbon, polymer, composite, ceramic, sintered material or any other suitable material. Broaching member 3502 may have one or more of a variety of cross sections, such as square, rectangular, octagonal, contours with sharp edges, stranded cable, or other suitable configurations to facilitate bone displacement.

Broaching member 3502 may include stainless steel, Nitinol (shapeset, superelastic or other Nitinol) or any other suitable substance.

Broaching member 3502 may be a substantially continuous structure. Broaching member 3502 may pass through channel 3512 in distal hub 3504. Broaching member 3502 may be fastened to distal hub 3504 in channel 3512.

Broaching member 3502 may be supported by distal hub 3504. Broaching member 3502 may be supported by proximal hub 3506. Proximal hub 3506 may be supported by broach sheath 3508. Broach sheath 3508 may have one or more features in common with broach sheath 127 (shown in FIG. 1) or any other broach sheath that is shown or described herein.

Drive shaft 3510 may drive broaching head 3500 in rotation. Drive shaft 3510 may extend distally to distal hub 3504. Drive shaft 3510 may extend to a proximal rotation source (not shown).

One or both of distal hub 3504 and proximal hub 3506 maybe axially fixed to drive shaft 3510. One or both of distal hub 3504 and proximal hub 3506 maybe rotationally fixed to drive shaft 3510.

Distal hub 3504 may be constructed of metal, stainless steel, laser-cut tube, polymer, ceramic or any other suitable material.

The distal end of drive shaft 3510 may extend into a channel (not shown) in distal hub 3504. Distal hub 3504 may be free to move axially with respect to drive shaft 3510. The channel in distal hub 3504 may be keyed for receiving a complementarily keyed distal end of drive shaft 3510. Drive shaft 3510 may thus drive broaching member 3502 distal portions 3518 and 3520.

During rotation, broaching member 3502 may elongate axially, along axis $L_G$ and push distal hub 3504 distally relative to drive shaft 3510. Such motion may contract broaching member 3502. During rotation, broaching member 3502 may expand axially along axis $L_G$ and draw distal hub 3504 proximally relative to drive shaft 3510. Contraction may occur, for example, when distal hub 3504 encounters resistant material.

Distal hub 3504 may be fixed to drive shaft 3510. Broaching member 3502 may be driven rotationally by application of torque to proximal ends 3514 and 3516 of broaching member 3502. Broaching member 3502 may be driven rotationally by application of torque to distal portions 3518 and 3520 of broaching member 3502.

Proximal ends 3514 and 3516 of broaching member 3502 may be affixed to drive shaft 3510 by proximal hub 3506. Proximal hub 3506 may engage proximal ends 3514 and 3516 by crimping, welding, set-screw, snap fit or any other suitable fastening.

Proximal hub 3506 may include or rotate with respect to a bearing (not shown). The bearing may be seated in the distal end of broach sheath 3508. Thus, when drive shaft 3510 rotates broaching member 3502, broach sheath 3508 and the bearing do not rotate. The orientation at which proximal ends 3514 and 3516 of broaching member 3502 are fixed to proximal hub 3506 may provide or retain a shape of broaching member 3502.

Distal hub 3504 may extend a distance E in the distal direction away from distal portions 3518 and 3520 of broaching member 3502. Distal hub 3504 may thus contact bone material inside bone B (shown in FIG. 2) before distal portions 3518 and 3520 contact the material. If the material is dense, such as cortical bone, the material may resist distal advancement of distal hub 3504. Broaching member 3502 may thus be prevented from broaching or interacting with the material.

Distal hub 3504 may include flutes 3522 and 3524. Broaching edges 3526, 3528, 3530, 3532, 3534 and 3536 may displace material inside bone B. Flutes 3522 and 3524 may intersect with each other at the distal end of distal hub 3504.

Distal hub 3504 may have a blunt distal end without flutes. This may prevent broaching member 3502 from interacting with material that resists distal advancement of distal hub 3504. The distal end of distal hub 3504 may be any suitable shape.

Distal hub 3504 may be absent from broaching head 3500.

Figure 36:
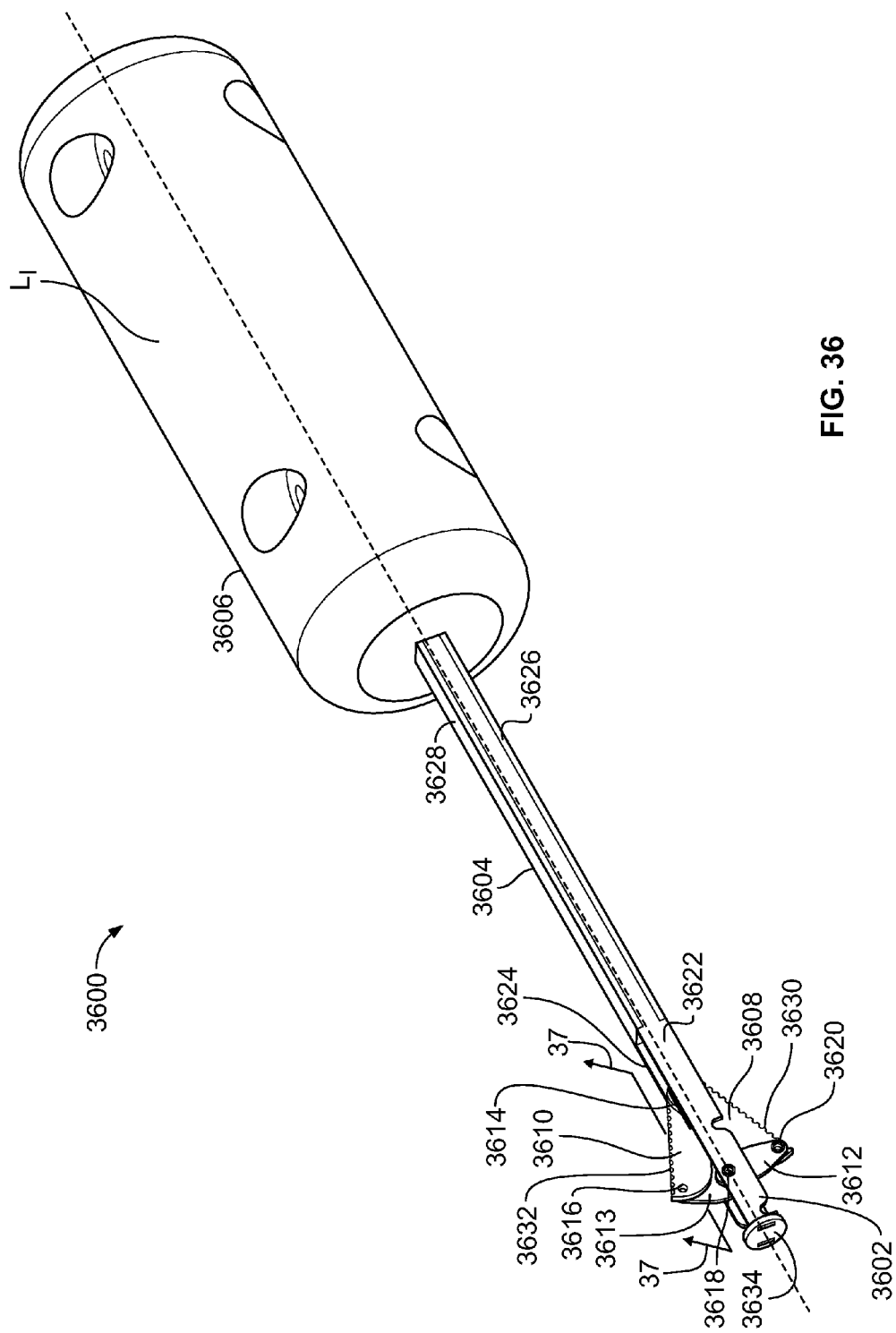
FIG. 36 shows yet other apparatus in accordance with the principles of the invention.

FIG. 36 shows illustrative broach 3600. Broach 3600 may include broaching head 3602, control shaft assembly 3604 and actuator 3606.

Broaching head 3602 may include linked blades 3608, 3610, 3612 and 3613. Linked blades 3608 and 3610 may have broaching edges 3630 and 3632, respectively. The broaching edges may broach bone inside bone B (shown in FIG. 2) when broach head 3602 is rotated about axis $L_I$.

The blades may positioned radially by a locking mechanism. The blades may be positioned radially by a resilient mechanism such that the blades may interact with bone tissue with sufficient pressure to displace bone tissue of certain densities, but insufficient pressure to substantially displace bones of a higher density.

Linked blades 3608, 3610, 3612 and 3613 may be linked by one or more linkages such as linkages 3614, 3616, 3618 and 3620. Linkage 3618 (and corresponding linkage 3619, not shown) may be supported by elongated members such as fixed struts 3622 and 3624. Fixed struts 3622 and 3624 may be fixed with respect to axis $L_I$. Fixed struts 3622 and 3624 may be joined by distal tip 3634.

Linkage 3614 may be supported by one or more elongated members, such as pull struts (not shown) that extend axially within control shaft assembly 3604. The pull struts may cause radial extension and contraction of the blades by changing the axial distance between (a) linkage 3614 and (b) linkages 3618 and 3619 (not shown).

Control shaft assembly 3604 may include fixed struts 3622 and 3624, the one or more pull struts (not shown), housing members 3626 and 3628, one or more filler members (not shown) and other suitable members (not shown).

Actuator 3606 may include elements for creating an offset between elongated members such as the fixed struts and the puller struts. Actuator 3606 may include elements for rotating broaching head 3602 about axis $L_I$.

Figure 37:
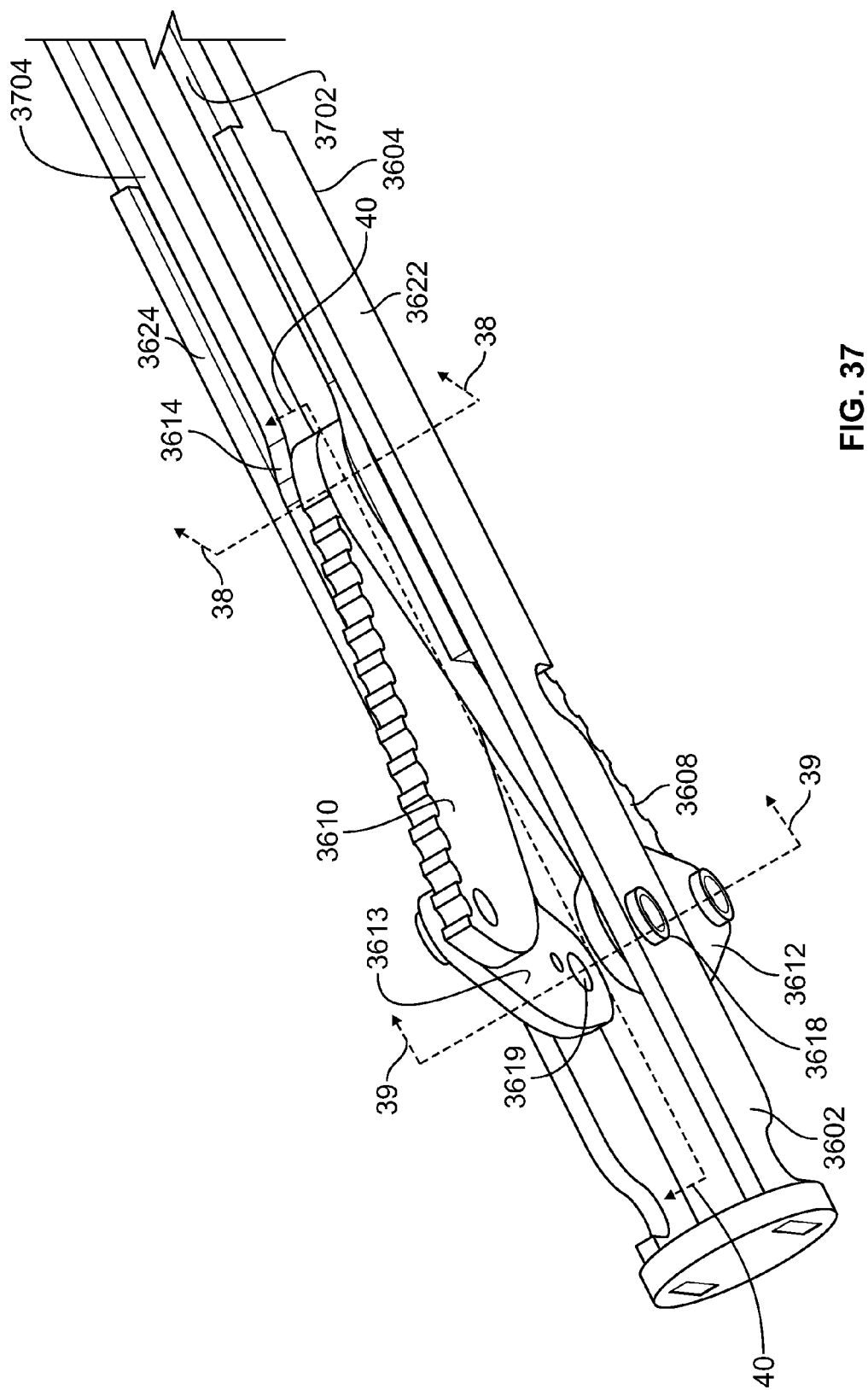
FIG. 37 shows a portion of the apparatus shown in FIG. 36.

FIG. 37 shows broaching head 3602 and a portion of control shaft assembly 3604 with housing members 3626 and 3628 removed. Pullers 3702 and 3704 may be present in control shaft assembly 3604 to move linkage 3614 axially relative to linkages 3618 and 3619.

Figure 38:
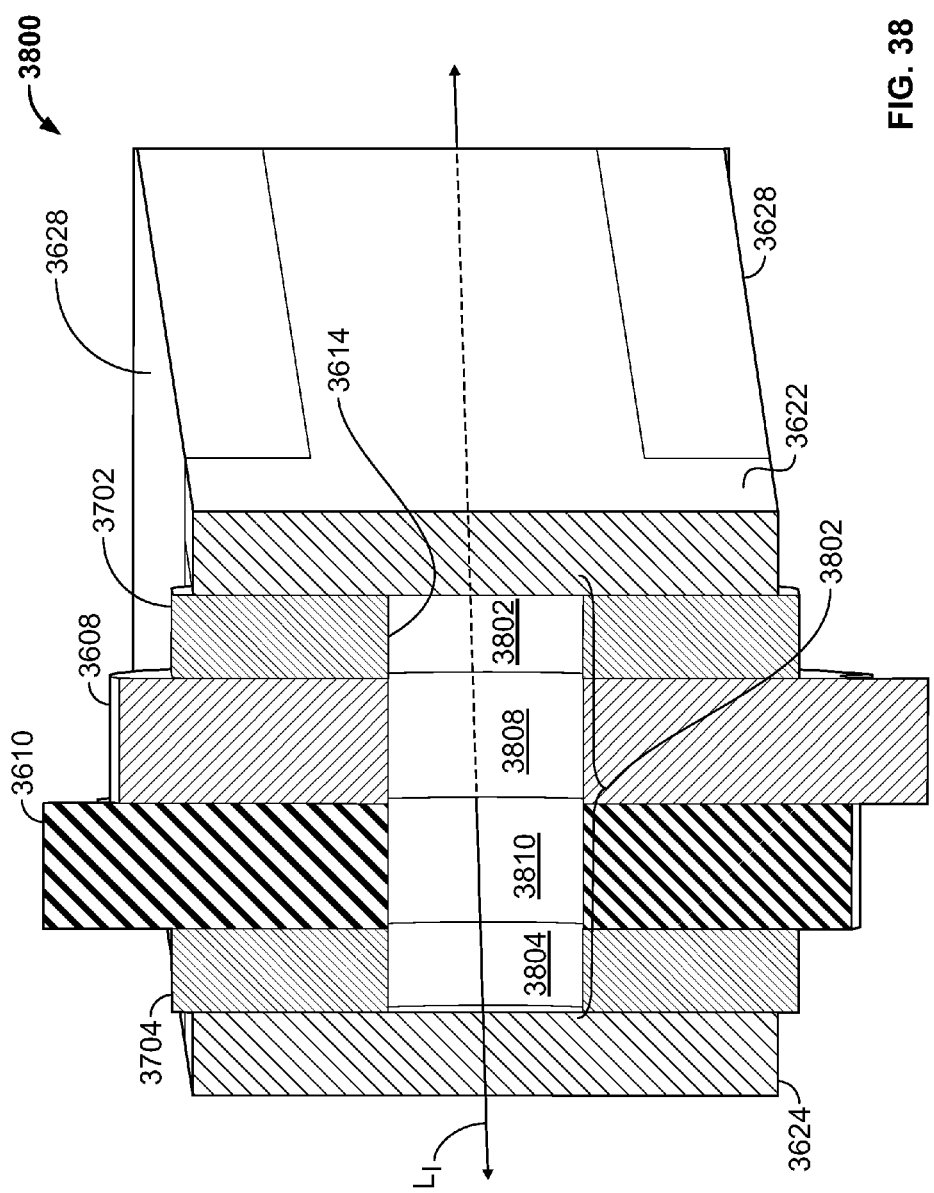
FIG. 38 shows a partial cross-sectional view, taken along lines 38-38 (shown in FIG. 37), of the apparatus shown in FIG. 37.

FIG. 38 shows illustrative portion 3800 of linkage 3614. Portion 3800 may be a pin channel that spans pull struts 3702 and 3704 and blades 3608 and 3610. A pin (not shown) may traverse the pin channel to axially align holes 3802, 3804, 3808 and 3810, of strut pull 3702, strut 3704, blade 3608 and blade 3610, respectively.

Figure 39:
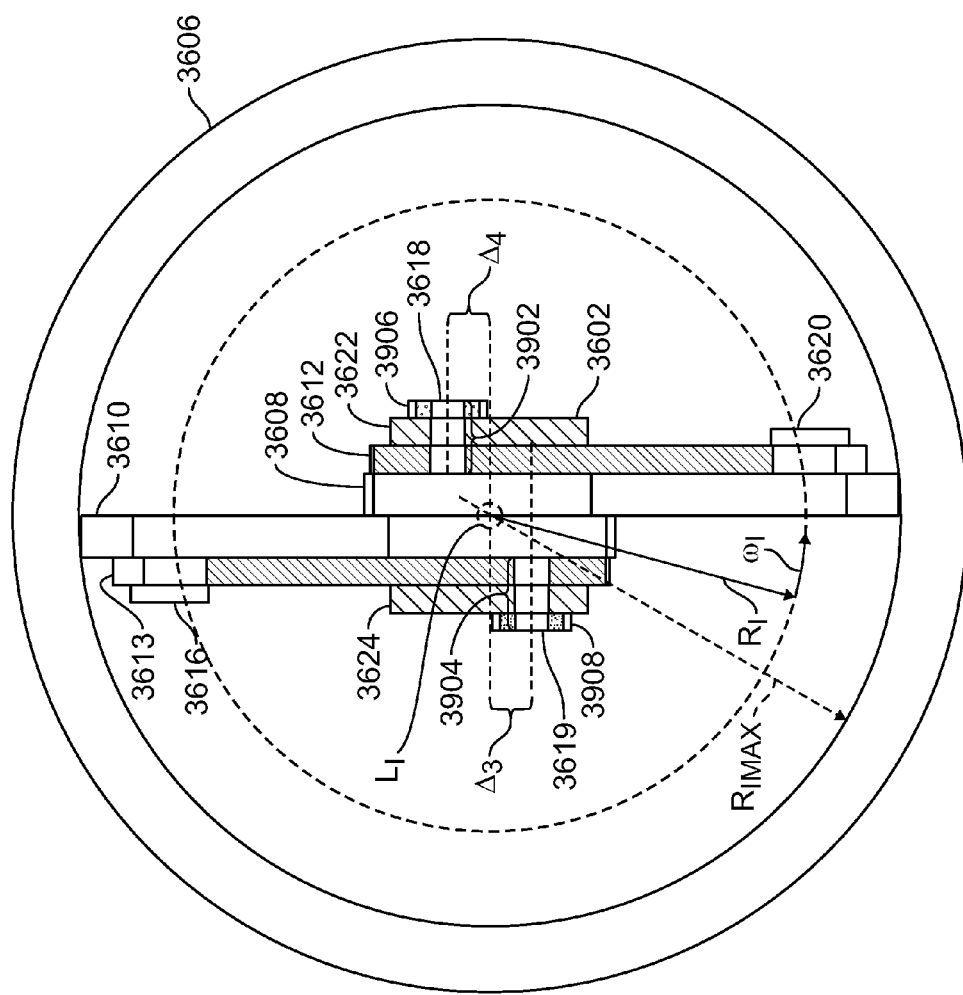
FIG. 39 shows a partial cross-sectional view, taken along lines 39-39 (shown in FIG. 37), of the apparatus shown in FIG. 37.

FIG. 39 shows pin channel 3902 of linkage 3618 and pin channel 3904 of linkage 3619. Pin channel 3902 traverses blade 3612, housing member 3622 and pin fastener 3906. Pin channel 3904 traverses blade 3613, housing member 3624 and pin fastener 3908.

A pin (not shown) may be present in channel 3902 to axially fix linkage 3618 to housing member 3622. A pin (not shown) may be present in channel 3904 to axially fix linkage 3619 to housing member 3624. Linkages 3619 and 3618 may be offset from axis $L_I$ by offsets $\Delta_3$ and $\Delta_4$.

When broach head 3602 is rotated in bone B (shown in FIG. 2) in direction $\omega_I$ or $-\omega_I$, with blades 3608 and 3610 positioned as shown, broaching edges 3630 and 3632 (shown in FIG. 36) will sweep out a space of radius $R_{IMAX}$, which is the maximum radius for broach head 3602. If linkage 3614 (shown in FIG. 36) were moved from the axial position shown, broaching edges 3630 and 3632 would sweep out a space of $R_I$.

Figure 40:
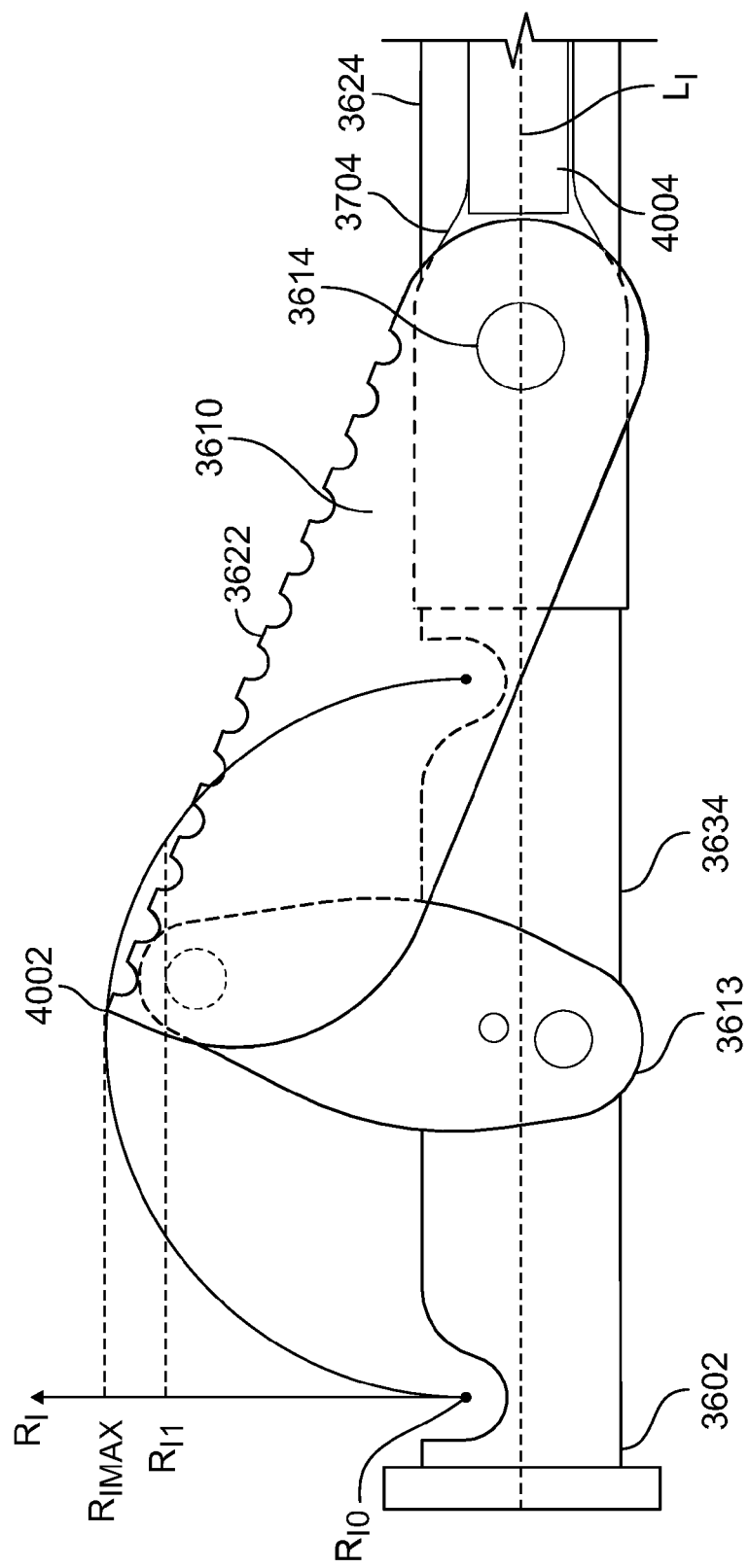
FIG. 40 shows a partial cross-sectional view, taken along lines 40-40 (shown in FIG. 37), of the apparatus shown in FIG. 37.

FIG. 40 shows the radial extent of tip 4002 of blade 3610 for different axial positions of linkage 3614.

When linkage 3614 is in a most-proximal position, tip 4002 may be at $R_I=R_{I0}$. At $R_{I0}$, broaching edge 3622 may be disengaged from bone B (shown in FIG. 2). When linkage 3614 is in an intermediate axial position, tip 4002 may be at $R_I=R_{I1}$. At $R_{I1}$, broaching edge 3622 may be engaged with bone B. At $R_I=R_{IMAX}$, broaching edge 3622 may be engaged with bone B at a maximum radius from axis $L_I$.

Filler members such as filler 4004 may be placed in spaces between pull struts. The filler members may be placed proximate blades that are actuated by the pull struts. The filler members may provide lateral stability to the pull struts.

Figure 41:
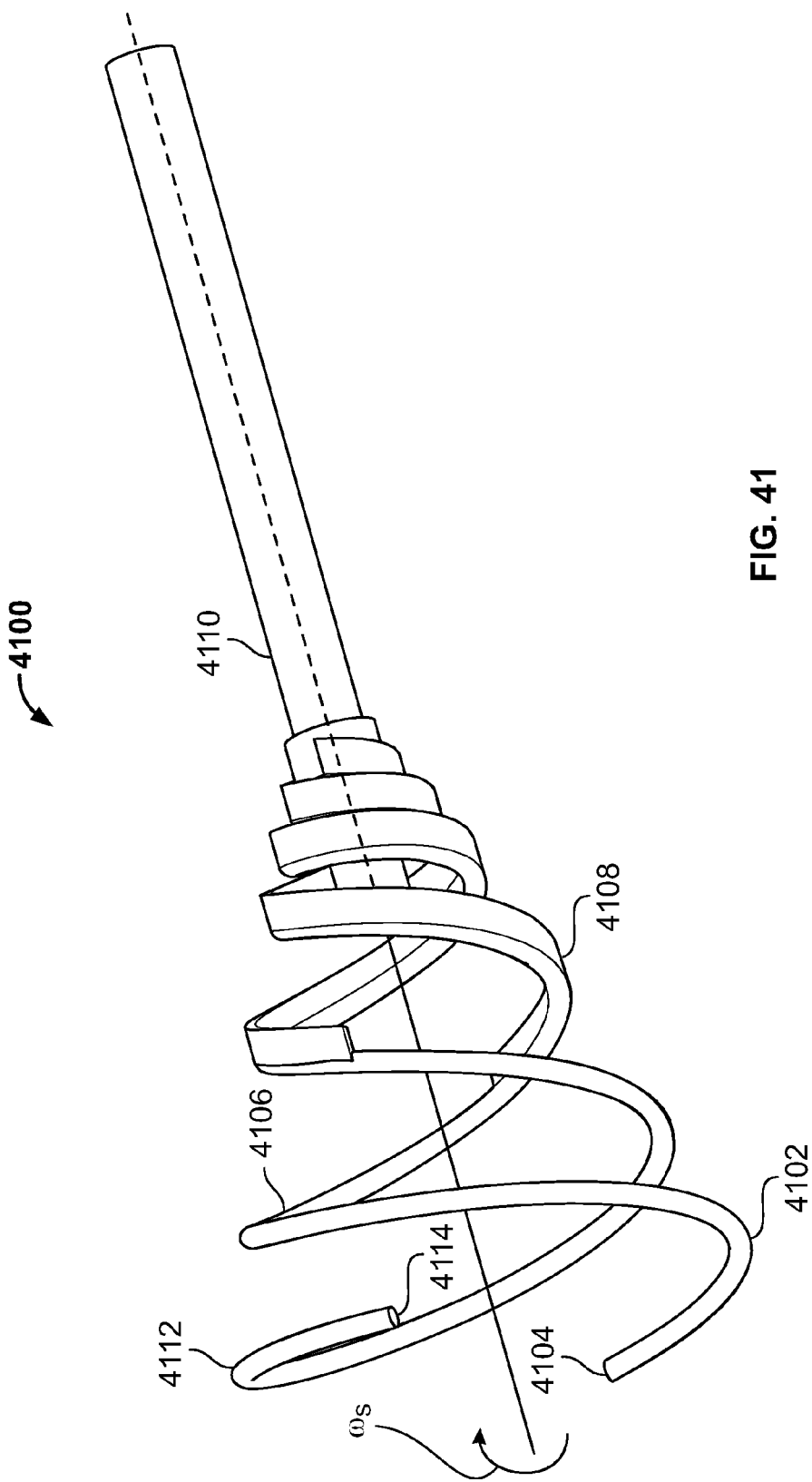
FIG. 41 shows yet other apparatus in accordance with the principles of the invention.

FIG. 41 shows illustrative broaching head 4100. Broaching head 4100 may include broaching members 4102. Each of broaching members 4102 may have one or more features in common with broaching member 704 (shown in FIG. 7) or any other broaching member shown or described herein. Broaching head 4100 may have any suitable number of broaching members 4102. For example, broaching head 4100 may have one broaching member, 2-6 broaching members, 7-20 broaching members, more than 20 broaching members or any suitable number of broaching members.

Broaching head 4100 may be contracted toward drive shaft 4110 and withdrawn into a broach sheath (not shown). The broach sheath may be inserted in a hole such as H (shown in FIG. 2). Broaching head 4100 may then be deployed by retracting the broach sheath. Broaching members 4102 may be sufficiently resilient to be contracted and may expand away from drive shaft 4110 when the broach sheath is retracted.

Broaching members 4102 may include free distal ends such as distal end 4104. Broaching members with free distal ends may be supported at their proximal ends near the central axis of broaching head 4100.

Distal end 4104 may have any suitable shape, such as pointed, forked, rounded, blunt or truncated.

Broaching members 4102 may be supported proximally by one or more of drive shaft 4110, a proximal hub (not shown), and a broach sheath. The broach sheath may have one or more features in common with broach sheath 127 (shown in FIG. 1).

Drive shaft 4110 may drive broaching head 4100 in rotation. The rotation may be in direction $\omega_s$. The rotation may be in direction $-\omega_s$. Drive shaft 4110 may extend through the broach sheath (not shown) to a proximal rotation source (not shown).

Broaching members 4102 may be rotated at high angular speed to break up cancellous bone, such as bone $B_{CA}$ (shown in FIG. 2). One or both of stiffness of broaching members 4102 and angular speed may be chosen to select a bone density threshold above which broaching members 4102 will have reduced or substantially no effect and below which broaching members 4102 will break up the cancellous bone.

One or more of broaching members 4102 may include a spiral segment such as 4106. Segment 4106 may be supported by one or more reinforcements such as 4108.

Segment 4106 may be rigid. Segment 4106 may be resilient. Segment 4106 may have any suitable pre-set curvature. Segment 4106 may include a substantially linear portion (not shown).

Segment 4106 may include a length of wire, ribbon, cable, stranded wire, or any other suitable form or structure. Segment 4106 may include polymer, metal, alloy or any other suitable material. Segment 4106 may be constructed of a mesh cut from metal tube.

Reinforcement 4108 may be a tube. A reinforcement 4108 may be formed from polymer, metal, alloy or any other suitable material. One or more reinforcements such as 4108 may be sized and positioned to support segment 4106 in a desired contour. One or more reinforcements such as 4108 may provide bone-broaching abrasiveness, momentum or both.

Reinforcement 4108 may be a brace.

Spiral segment 4112 may "spiral" in the same direction as spiral segment 4106. Spiral segment 4112 may "spiral" in the opposite direction from spiral segment 4106 such that distal tips 4104 and 4114 "face" in opposite circumferential directions.

Broaching members 4102 may be absent from broaching head 4100. Reinforcements such as 4108 may be present in broaching head 4100 to perform as broaching members.

Figure 42:
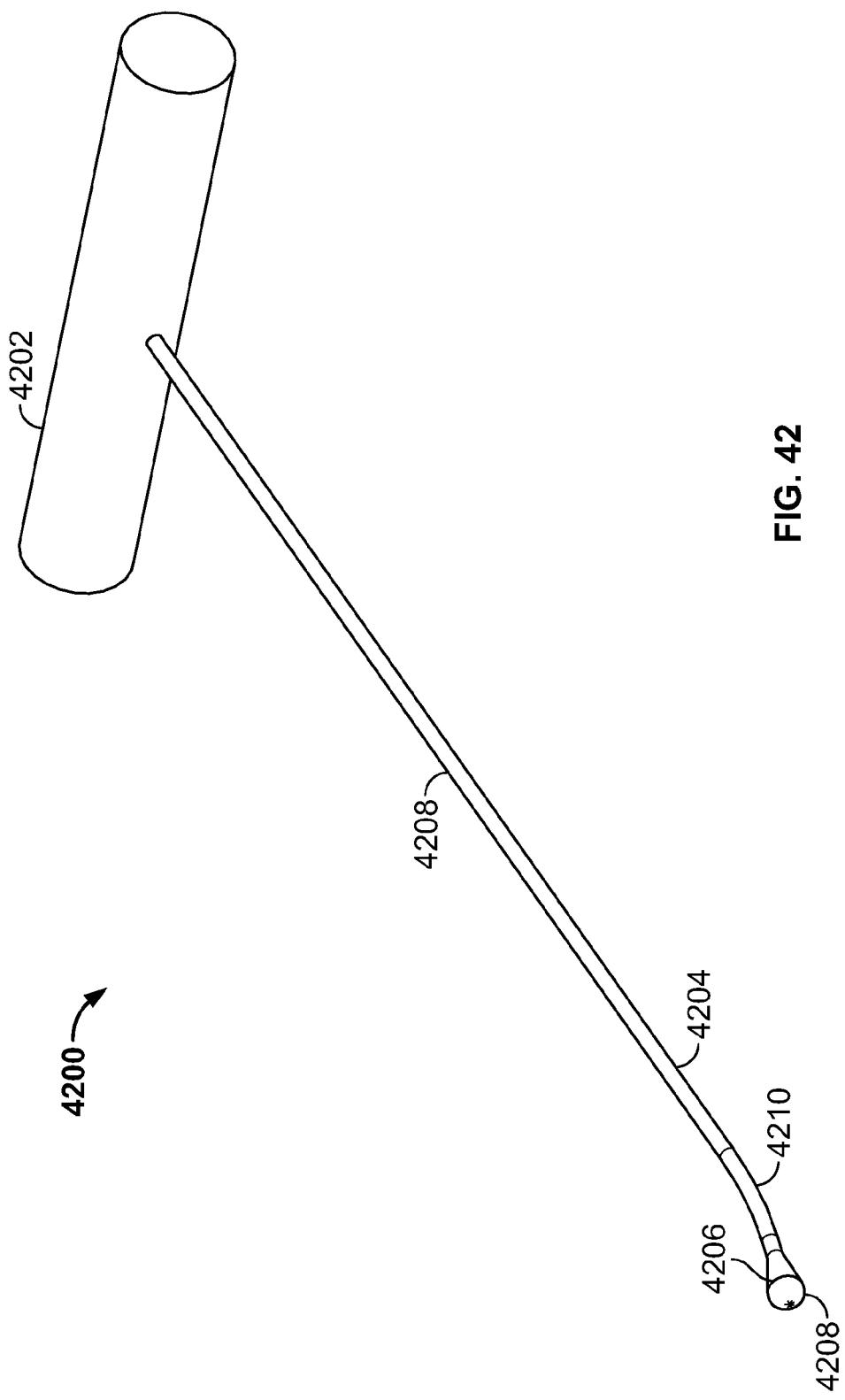
FIG. 42 shows yet other apparatus in accordance with the principles of the invention.

FIG. 42 shows illustrative intramedullary tool 4200. Tool 4200 may include handle 4202, elongated support 4204 and probe 4206.

A practitioner may use handle 4202 to insert probe 4206 into intramedullary space IS of bone B (shown in FIG. 2). Probe 4206 may be used to determine the spatial distribution of cancellous bone $B_{CA}$ (shown in FIG. 2) in intramedullary space IS. Probe 4206 may be used to apply force to a bone fragment such as fragments $P_h$ and $P_a$ (shown in FIG. 2) to position the bone fragment for provisional reduction of a fracture such as $F_h$ and $F_a$ (shown in FIG. 2). Probe 4206 may be viewed in situ via fluoroscopic imagery or any other suitable type of imagery during operation of tool 4200.

Probe 4206 may include distal face 4208. Distal face 4208 may be rounded, conical, faceted or any other suitable shape. Probe 4206 may include a wire loop.

Probe 4206 may include polymer, alloy or any other suitable material.

Elongated support 4204 may include one or more straight portions such as portion 4208. Elongated support 4204 may include one or more curved portions such as portion 4210. Elongated support 4204 may be shaped such that probe 4206 may be inserted into an angled access hole such as H or I (shown in FIG. 2) and advanced substantially along bone axis LB toward distal end D of bone B (shown in FIG. 2).

Elongated support 4204 may include one or more rigid sections. Elongated support 4204 may include one or more flexible sections. A flexible section may help probe 4206 negotiate a turn from the angled access hole into the intramedullary space. A flexible section may help probe 4206 deflect away from high density bone, such as high density cancellous bone or cortical bone, during advancement substantially along bone axis LB (shown in FIG. 2).

Elongated support 4204 may have one or more solid sections. Elongated support 4204 may have one or more cannulated sections.

Elongated support 4204 may include polymer, alloy or any other suitable material.

Thus, apparatus and methods for fracture repair have been provided. Persons skilled in the art will appreciate that the present invention can be practiced by other than the described embodiments, which are presented for purposes of illustration rather than of limitation. The present invention is limited only by the claims that follow.

What is claimed is:

1. Apparatus for preparing a bone cavity for implantation of an implant, the apparatus comprising:
    a drive shaft defining a radial direction and a longitudinal direction;
    a plurality of broaching members, each broaching member having a proximal end and a distal end; and
    a hub fixed to a terminal end of the drive shaft, the hub including a hub proximal end and a plurality of faces extending away from a flat, disc-shaped cap positioned at a hub distal end toward the hub proximal end, the faces defining a plurality of openings; wherein:
        operationally, a distal end, and not a proximal end, of each of the broaching members, aligns with the radial direction through one of the openings;
        each opening is positioned between a first of the faces and a second of the faces; and
        each of the faces follows a constant radius along the longitudinal direction.

2. The apparatus of claim 1 wherein each broaching member includes a cutting edge.

3. The apparatus of claim 1 further comprising, when the hub is a distal hub, a proximal hub fixed to a proximal end of the drive shaft, wherein the proximal ends of the broaching members are supported by the proximal hub.

4. The apparatus of claim 1 wherein the hub is constructed of laser-cut tube.

5. The apparatus of claim 1 wherein the cap borders the openings.

6. Apparatus for preparing a bone cavity for implantation of an implant, the apparatus comprising:
    a drive shaft defining a radial direction and a longitudinal direction;
    a hub fixed to a terminal end of the drive shaft, the hub including a hub proximal end and a plurality of faces extending away from a flat, disc-shaped cap positioned at a hub distal end toward the hub proximal end, the faces defining a plurality of openings;
    a plurality of bone broaching members; and
    a plurality of supporting members, each of the supporting members supporting one of the bone broaching members and having a proximal end and a distal end, wherein each of the proximal ends is coupled to one of the bone broaching members;
    wherein:
        in operation, a distal end, and not a proximal end, of each of the supporting members aligns with the radial direction through one of the openings;
        each opening is positioned between a first of the faces and a second of the faces; and
        each of the faces follows a constant radius along the longitudinal direction.

7. The apparatus of claim 6 wherein each bone broaching member includes a cutting edge.

8. The apparatus of claim 6 wherein the drive shaft is configured to drive the bone broaching members and the supporting members in rotation.

9. The apparatus of claim 6, when the hub is a distal hub, further comprising a proximal hub fixed to a proximal end of the drive shaft, the bone broaching members being coupled to the proximal hub.

10. The apparatus of claim 6, when the proximal end is a supporting member proximal end and the distal end is a supporting member distal end, further comprising a proximal hub wherein:
    each bone broaching member includes a bone broaching member distal end and a bone broaching member proximal end;
    each bone broaching member distal end is coupled to one of the supporting member proximal ends; and
    each bone broaching member proximal end is coupled to the proximal hub.

11. The apparatus of claim 6 wherein the supporting members are formed from a pattern that is cut into a metal tube.

12. The apparatus of claim 6 wherein the hub is constructed of laser-cut tube.

13. The apparatus of claim 6 wherein the cap borders the openings.

* * * * *

UNITED STATES PATENT AND TRADEMARK OFFICE
CERTIFICATE OF CORRECTION

PATENT NO. : 9,848,889 B2
APPLICATION NO. : 14/929757
DATED : December 26, 2017
INVENTOR(S) : Kyle Taylor et al.

Page 1 of 1

It is certified that error appears in the above-identified patent and that said Letters Patent is hereby corrected as shown below:

In the Specification
Column 8, Line 36, replace "50" with --5°--.
Column 17, Line 51, replace "a" with --α--.
Column 17, Line 52, replace "a" with --α--.
Column 25, Line 63, replace "L;" with --Lc--.

Signed and Sealed this
Twenty-fourth Day of July, 2018

Andrei Iancu
*Director of the United States Patent and Trademark Office*